(12) United States Patent
Lee et al.

(10) Patent No.: US 8,394,799 B2
(45) Date of Patent: Mar. 12, 2013

(54) COMPOUNDS THAT INHIBIT HIF-1 ACTIVITY, THE METHOD FOR PREPARATION THEREOF AND THE PHARMACEUTICAL COMPOSITION CONTAINING THEM AS AN EFFECTIVE COMPONENT

(75) Inventors: Jung Joon Lee, Taejeon-si (KR); Jeong-Hyung Lee, Taejeon-si (KR); Kyeong Lee, Taejeon-si (KR); Young-Soo Hong, Taejeon-si (KR); B. K. Shanthaveerappa, Taejeon-si (KR); Yinlan Jin, Taejeon-si (KR); Jin Hwan Kim, Taejeon-si (KR); Xuejun Jin, Taejeon-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 648 days.

(21) Appl. No.: 12/306,319

(22) PCT Filed: Jul. 3, 2007

(86) PCT No.: PCT/KR2007/003216
§ 371 (c)(1),
(2), (4) Date: Dec. 23, 2008

(87) PCT Pub. No.: WO2008/004798
PCT Pub. Date: Jan. 10, 2008

(65) Prior Publication Data
US 2009/0306078 A1 Dec. 10, 2009

(30) Foreign Application Priority Data
Jul. 4, 2006 (KR) .................. 10-2006-0062722

(51) Int. Cl.
*A61K 31/5377* (2006.01)
*A61K 31/167* (2006.01)
*A61K 31/41* (2006.01)
*A61K 31/423* (2006.01)
*A61P 19/02* (2006.01)
*C07C 233/33* (2006.01)
*C07D 257/04* (2006.01)
*C07D 263/57* (2006.01)
*C07D 295/15* (2006.01)

(52) U.S. Cl. .................. 514/237.8; 514/375; 514/381; 514/622; 544/155; 548/217; 548/253; 56/172

(58) Field of Classification Search .................. None
See application file for complete search history.

(56) References Cited

U.S. PATENT DOCUMENTS
3,182,070 A  5/1965  Moyle et al.
6,444,849 B1  9/2002  Ando et al.

FOREIGN PATENT DOCUMENTS
WO   89/01488   2/1989
WO   03/037328  5/2003
WO   2004/009533  1/2004

OTHER PUBLICATIONS

Minton, T. H. & Stephen, H., Coumaranone series. II. The preparation of 4- and 6-chlorocoumaran-2-ones and their conversion into 2- and 4-chloroflavanols and some derivatives of o- and p-chlorophenoxyacetic acids, 121, J. Chem. Soc., Trans. 1598-603 (1922).*
Tozer, B.T., & Smiles, S., Rearrangement of o-carbamyl derivatives of diphenylether, J. Chem. Soc. 2052-6 (1938).*
Newman et al., New compounds as plant growth regulators, 69 J. Am. Chem. Soc. 718-23 (1947).*
Nametkin et al., Some derivatives of hydroxybiphenyl, 19 Zhurnal Obshchei Khimii 1151-7 (1949).*
Kyeong Lee et al., (Aryloxyacetylamino)benzoic Acid Analogues: A New Class of Hypoxia-Inducible Factor-1 Inhibitors, 50(7) J. Med. Chem. 1675-84 (2007).*
Gobec, S., et al., Nonsteroidal anti-inflammatory drugs and their analogues as inhibitors of aldo-keto reductase AKR1C3: New lead compounds for the development of anticancer agents, Bioorganic & Medicinal Chemistry Letters, vol. 15(23), pp. 5170-5175, 2005.
Caballero, J., et al., Linear and nonlinear modeling of antifungal activity of some heterocyclic ring derivatives using multiple linear regression and Bayesian-regularized neural networks, J. Mol. Model., vol. 12(2), pp. 168-181, 2006.
Yalcin, I., et al., QSARs of some novel isosteric heterocyclics with antifungal activity, Acta Biochimica Polonica, vol. 47(2), pp. 481-486, 2000.

* cited by examiner

*Primary Examiner* — Janet Andres
*Assistant Examiner* — Timothy R Rozof
(74) *Attorney, Agent, or Firm* — Lucas & Mercanti, LLP

(57) ABSTRACT

Disclosed herein are an HIF-1 inhibitor, a method for the preparation thereof, and a pharmaceutical composition comprising the same as an active ingredient. The HIF-1 inhibitor shows anticancer activity thanks to the inhibition activity against HIF-1, a transcription factor which plays an important role in the growth and metastasis of cancer, but not to general cytotoxicity. Thus, the HIF-inhibitor and a pharmaceutically acceptable salt thereof can be used as a therapeutic for various cancers such as liver cancer; stomach cancer and breast cancer. Also, the compound having inhibition activity against HIF-1 is useful in the treatment of diabetic retinopathy and arthritis, which are aggravated by HIF-1-mediated VEGF expression.

8 Claims, 5 Drawing Sheets

COMPOUNDS THAT INHIBIT HIF-1 ACTIVITY, THE METHOD FOR PREPARATION THEREOF AND THE PHARMACEUTICAL COMPOSITION CONTAINING THEM AS AN EFFECTIVE COMPONENT

CROSS-REFERENCE TO RELATED APPLICATIONS

This application is a 371 of PCT/KR2007/003216, filed Jul. 3, 2007, which claims the benefit of Korean Patent Application No. 10-2006-0062722, filed Jul. 4, 2006, the contents of each of which are incorporated herein by reference.

TECHNICAL FIELD

The present invention relates to compounds that inhibit HIF-1 activity, the method for preparation thereof, and a pharmaceutical composition containing the same as an active ingredient.

BACKGROUND ART

In spite of extensive efforts conducted for decades all over the world, cancer still remains one of the most incurable diseases. Recently, with great and brilliant advances in all sorts of sciences comprising cancer biology and medicinal chemistry, anticancer agents such as Gleevec, which have innovative mechanisms, have been developed. Since the completion of the Human Genome Project) new molecules that are targets of anticancer agents have been discovered. HIF-1(Hypoxia Inducible Factor-1) is a heterodimeric transcription factor composed of two subunits: HIF-1α subunit an oxygen-dependent decomposition domain; and HIF-1β subunit, a constitutively expressed domain [Cancer Metastasis Rev., 17, 187-195, 1998; Trends Mol. Med., 7, 345350, 2001].

Under normal oxygen concentrations, the HIF-1α protein is hydroxylated depending on the oxygen at proline residues 402 and 564, thereby it will be ubiquitinated by interacting the tumor suppressor pVHL (von Hippel-Lindau) and decomposed by proteasome. In hypoxia, however, these consecutive reactions are inhibited, so that the HIF-1α protein is accumulated and translocated as a dimeric complex associated with the preexisting HIF-1β protein into the nucleus [Science 292, 468-472, 2001; Science 292, 468-472, 2001]. The stability of HIF-1α depends not only on partial oxygen pressure but also on factors involved in an oxygen sensing pathway, including transition metal ions, iron chelators, and antioxidants. In addition, the HIF-1α protein can accumulate irrespective of oxygen concentrations by activation of growth factors, such as epidermal growth factor, heregulin, insulin-like growth factor-L insulin-like growth factor-II, etc., or of oncogenes, such as ErbB2, etc. When these growth factors bind to respective receptors, it is increase that HIF-1α protein is synthesized by activating the PI3K-AKT or MAPK signal transduction pathway, with the result that the HIF-1α protein accumulates.

Within a nucleus, HIF is associated with an HRE (Hypoxia Responsive Element; 5'-ACGTG-3') on the promoter of a target gene to induce the expression of the gene. There are about 60 genes that have been known to be regulated by HIF, including a vascular endothelial growth factor (VEGF) gene [*Nat. Rev. Cancer* 2, 38-47, 2002; *J. Biol. Chem.* 278, 19575-19578, 2003; *Nat, Med.* 9, 677-684, 2003; *Biochem. Pharmacol.* 64, 993-998, 2002].

Hypoxia is usual in cancer, in particular solid cancer. Because solid cancer cells are adapted to a low oxygen condition after being subjected to various genetic alterations, they become more malignant and resistant to anticancer agents. In fact, hypoxia is known to play an important role in malignant cancer in over 70% of all cancer types [Nature 386, 403, 1997; Hockel M and Vaupel P, Semin. Oncol. 28, 36-41, 2001, Nature Med. 6, 1335, 2000; Bos et al. Cancer 2003, 97, 1573-1581]. HIF-1 is one of the most important molecules regulating the adaptation of cancer cells to hypoxia, and the amount of HIF-1α protein is closely correlated with poor prognosis of cancer patients. Whether attributed to the hypoxia, or above-mentioned the stimulation of growth factors or the activation of oncogenes, or the inactivation of tumor suppressors, such as pVHL, the cancer cells are activated, HIF-1 induces the expression of various genes encoding, for example, hexokinase 2, glucose transporter 1, erythropoietin, IGF-2, endoglin, VEGF, MMP-2, uPAR, MDR1, etc., leading to improvement in apoptosis resistance, angiogenesis, cell proliferation, and invasiveness, thereby resulting in the malignant transformation of cancer cells. Because it plays a pivotal role in the growth, proliferation and malignant transformation of cancer, in particular, solid cancer, HIF has become a major target of many anticancer agents, and active and extensive research has been conducted thereon [Cancer Res. 62, 4316, 2002; Nat Rev Drug Discovery 2, 1, 2003; Semenza et al. Nature Reviews Cancer 2003, 3, 721-732]. Recently, a significant number of preexisting anticancer agents, such as taxol, rafamycin and 17-AAG (17-allylaminogeldanamycin), or small molecular compound YC-1 (3-(5-hydroxymethyl-2'-1-bend azole) a undergoing various clinical demonstrations for use as HIF-1 inhibitors [Johnson et al Nature Reviews Drug Discovery 2003, 2, 1-9; Semenza et al. Nature Reviews Cancer 2003, 3, 721-732; JNCI 95, 516, 2003], and cell based reporter assays for screening HIF-1 inhibitors of new structures are being actively conducted by taking advantage of HRE [Cancer Res 65, 4918, 2005; Cancer Cell 6, 33, 2004; Cancer Res. 62, 4316, 2002). However, these are in the early stage of drug discovery.

HIF-1 can be used as a valid target for novel anticancer therapeutics. Angiogenesis factors which are derived by an activated HIF-1 in hypoxia condition, such as VEGF, are associated with the progress of diabetic retinopathy and arthritis as well as cancer. Accordingly, the compounds that inhibit an activated HIF-1 from hypoxia condition can also be used as novel therapeutics for the diseases comprising diabetic retinopathy and rheumatoid arthritis [Eiji Ikeda, Pathology International, 2005, Vol 55, 603-610]. However, this field is still in its infancy.

DISCLOSURE

Technical Problem

An object of the present invention is to provide a compound having inhibition activity against the transcription factor HIF-1.

Another object of the present invention is to provide a method for preparing an inhibitor of HIF-1 activity.

Further object of the present invention is to provide a pharmaceutical composition for the treatment of various cancers, comprising the compound as an active ingredient useful in the suppression of the growth and metastasis of cancer.

Still a further object of the present invention is to provide a pharmaceutical composition for the treatment of diabetic retinopathy and arthritis.

Technical Solution

In accordance with an object, the above objects of the present invention could be accomplished by the provision of a compound represented by Chemical Formula 1A or 1B as defined below.

The compound functions to selectively suppress the growth and metastasis of tumor cells, thereby showing potent anticancer activity with little or no side effects. Also, the compound is useful in the treatment of diabetic retinopathy and arthritis through the inhibitory mechanism against HIF-1 activity.

In accordance with another object: provided are a method for preparing the compound and a pharmaceutical composition containing the compound.

Advantageous Effect

The compound of the present invention shows anticancer activity not through general cytotoxicity, but through inhibition activity of HIF-1 activity, particularly through dose-dependent inhibition activity against HIF-1α accumulation in hypoxia. Having selective inhibition activity, the compound of the present invention is effective for suppressing the expression of the genes involved in the malignant transformation of cancer, thereby preventing the growth and metastasis of cancer.

Therefore, the compound of the present invention, serving as an HIF-1 inhibitor, is useful in the treatment of various cancers, including liver cancer, stomach cancer, breast cancer, colon cancer, bone cancer, pancreatic cancer, head or neck cancer, uterine cancer, ovarian cancer, rectal cancer, esophageal cancer, small intestine cancer, periproctic cancer, oviduct cancer, endometrial cancer, cervical cancer, vulva cancer, vaginal cancer, Hodgkin's disease, prostate cancer, bladder cancer, kidney cancer, ureter cancer, renal cell carcinoma, renal pelvis cancer, and CNS tumors.

In addition, the compound of the present invention has selective inhibition activity against VEGF, a target gene of HIF-1, and thus can be used as an ingredient of therapeutics for diabetic retinopathy and arthritis, which are aggravated upon HIF-1-mediated VEGF expression in hypoxia.

BEST MODE

Figure 1:
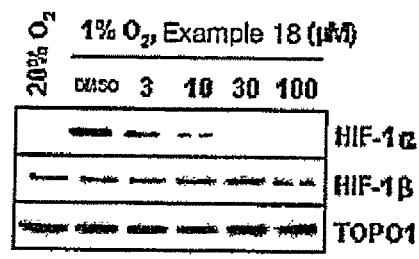
FIG. 1 shows the inhibition activity of the compounds of the invention against HIF-1a accumulation in hypoxia at each concentration.
Figure 1:
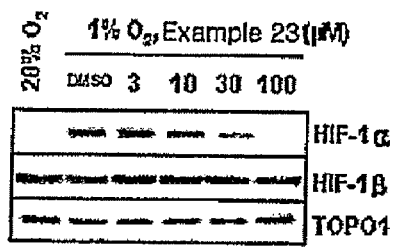
Figure 1:
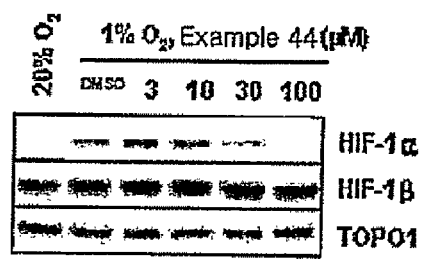
Figure 1:
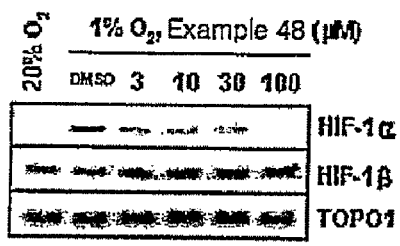
Figure 1:
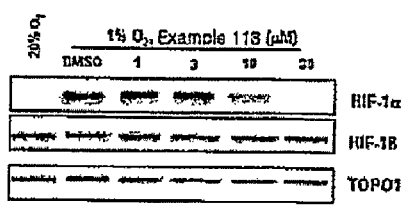
Figure 1:
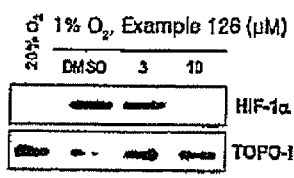

In accordance with an embodiment of the present invention, provided is a compound represented by the following Chemical Formula 1A or 1B, or a pharmaceutically available salt thereof.

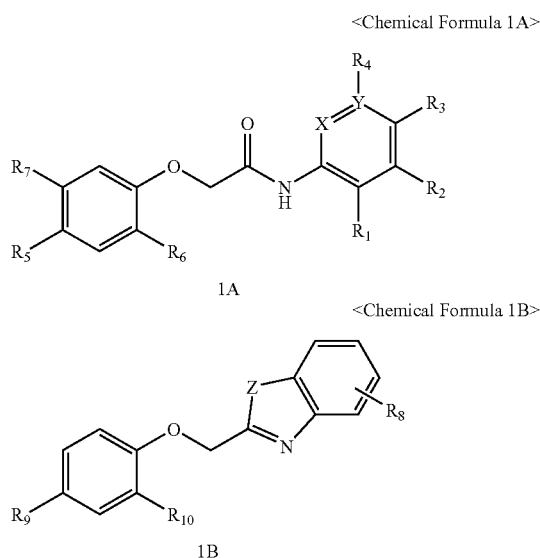

<Chemical Formula 1A>

<Chemical Formula 1B>

(wherein,

X and Y are each C or N, preferably with the proviso that when X is C, Y is C or N and when Y is N, X is C or N;

Z is O or NE $R_1$ is selected from a group consisting of H OH and COORa where Ra is H or $C_1$~$C_2$ alkyl;

$R_2$ is selected from a group consisting of H, OH, CN, $CF_3$, $C_1$~$C_2$ alkyl, COORa, $CH_2$COORa, CONRbRc, $SO_2NH_2$, $SO_2CH_3$, $SO_2CH_2OH$, O(C=O)$NH_2$, $OSO_2NH_2$, tetrazole, $C_1$~$C_3$ allyl-substituted tetrazole, and benzoyl, the Ra being H or $C_1$~$C_2$ alkyl the Rb and the Rc being independently selected from a group consisting of $C_3$~$C_5$ heteroaryl containing N, O and/or S; $C_1$~$C_5$ alkyl substituted with a $C_3$~$C_5$ heteroaryl or heterocyclic group containing N, O and/or S; $C_1$~$C_3$ alkyl substituted with OH and/or phenyl; phenyl substituted with halogen and/or trihalomethyl; naphthyl; H; and $C_1$~$C_3$ alkyl;

$R_3$ is selected from a group consisting of H, COORa and $SO_2NH_2$, the Ra being H or $C_1$~$C_2$ alkyl;

$R_4$ is selected from a group consisting of H, COORa and CONRbRc, the Ra being H or $C_1$~$C_2$ alkyl, the Rb and the Rc being independently selected from a group consisting of $C_1$~$C_3$ alkyl substituted with a $C_3$~$C_5$ heteroaryl or heterocyclic group containing N, O and/or S; $C_1$~$C_3$ alkyl substituted with an amino group or a $C_1$~$C_2$alkyl-substituted amino group; H; and $C_1$~$C_2$ alkyl;

$R_5$ is selected from a group consisting of H $C_1$~$C_{10}$ alkyl, phenyl, halogen, nitro and acetyl;

$R_6$, $R_7$ are $R_{10}$ are independently selected from a group consisting of H and halogen;

$R_8$ is a substituent located at the $C_5$ or $C_6$ position on the benzooxazole or benzoimidazole, selected from a group consisting of H, COORa, CONRbRc and $SO_2NH_2$, the Ra being selected from H and $C_1$~$C_2$ alkyl, the Rb and the Rc being independently selected from $C_1$~$C_5$ alkyl substituted with a $C_3$~$C_5$ heteroaryl or heterocyclic group containing N, O and/or S; $C_1$~$C_5$ alkyl substituted with an amino group or with a $C_1$~$C_3$ alkyl-substituted amino group; amino; H; and $C_1$~$C_3$ alkyl; and $R_9$ is selected from a group consisting of $C_1$~$C_{10}$ alkyl, halogen and nitro group.)

Concrete examples of the compounds represented by Chemical Formula 1A and 1B, according to the present invention, are given in Table 1, below.

TABLE 1

|  | R₁ | R₂ | R₃ | R₄ |
|---|---|---|---|---|
| Example 1 | H | SO₂CH₃ | H | H |
| Example 2 | H | COOCH₃ | H | H |
| Example 3 | H | COOCH₂CH₃ | H | H |
| Example 4 | H | CH₂COOCH₃ | H | H |
| Example 5 | H | H | COOCH₃ | H |
| Example 6 | COOCH₃ | H | H | H |
| Example 7 | H | COOCH₃ | H | COOCH₃ |
| Example 8 | H | COOCH₃ | H | H |
| Example 9 | H | COOCH₃ | H | H |
| Example 10 | H | COOCH₃ | H | H |
| Example 11 | H | COOCH₃ | H | H |
| Example 12 | COOCH₃ | H | H | H |
| Example 13 | H | H | COOCH₃ | H |
| Example 14 | H | COOCH₃ | H | H |
| Example 15 | H | COOCH₃ | H | H |
| Example 16 | H | COOCH₃ | H | H |
| Example 17 | H | COOCH₃ | H | H |
| Example 18 | OH | H | H | COOCH₃ |
| Example 19 | OH | H | H | COOCH₃ |
| Example 20 | H | COOCH₃ | H | H |
| Example 21 | COOCH₃ | H | COOCH₃ | H |
| Example 22 | H | COOCH₃ | H | H |
| Example 23 | H | CONH₂ | H | H |
| Example 24 | H | CONH₂ | H | H |
| Example 25 | H | CONH₂ | H | H |
| Example 26 | H | CONH₂ | H | H |
| Example 27 | H | CONH₂ | H | H |
| Example 28 | H | CONH₂ | H | H |
| Example 29 | H | CONH₂ | H | H |
| Example 30 | H | CONH₂ | H | H |
| Example 31 | H | CONH₂ | H | H |
| Example 32 | H | CONH₂ | H | H |
| Example 33 | H | SO₂NH₂ | H | H |
| Example 34 | H | H | SO₂NH₂ | H |
| Example 35 | H | CN | H | H |
| Example 36 | H | CN | H | H |
| Example 37 | H | CF₃ | H | H |
| Example 38 | H | OH | H | H |
| Example 39 | H | OH | H | H |
| Example 40 | H | 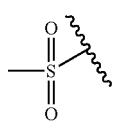 | H | H |
| Example 41 | H | 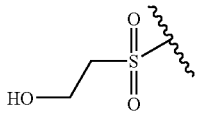 | H | H |

TABLE 1-continued

| | | | | |
|---|---|---|---|---|
| Example 42 | H | 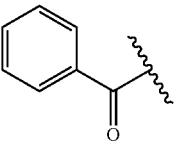 [SMILES: *C(=O)c1ccccc1] | H | H |
| Example 43 | COOH | H | H | H |
| Example 44 | H | COOH | H | H |
| Example 45 | H | CH$_2$COOH | H | H |
| Example 46 | H | H | COOH | H |
| Example 47 | H | COOH | H | H |
| Example 48 | OH | H | H | COOH |
| Example 49 | OH | H | H | COOH |
| Example 50 | H | COOH | H | COOH |
| Example 51 | H | COOH | H | H |
| Example 52 | H | COOH | H | H |
| Example 53 | H | COOH | H | H |
| Example 54 | COOH | H | H | H |
| Example 55 | H | H | COOH | H |
| Example 56 | H | COOH | H | H |
| Example 57 | H | COOH | H | H |
| Example 58 | H | COOH | H | H |
| Example 59 | H | COOH | H | H |
| Example 60 | H | COOH | H | H |
| Example 61 | H | 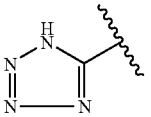 [SMILES: *c1nnn[nH]1] | H | H |
| Example 62 | H | 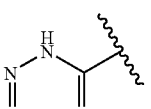 | H | H |
| Example 63 | H | 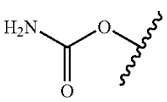 | H | H |
| Example 64 | H | 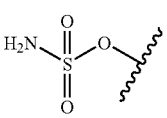 [SMILES: *OS(N)(=O)=O] | H | H |
| Example 65 | OH | H | H | CONH$_2$ |
| Example 66 | OH | H | H | 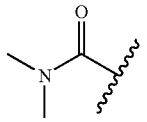 |
| Example 67 | OH | H | H | 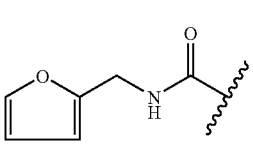 [SMILES: *C(=O)NCc1ccco1] |

TABLE 1-continued
| | | | | |
|---|---|---|---|---|
| Example 68 | OH | H | H | 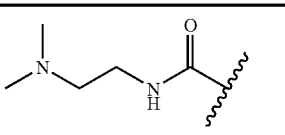 |
| Example 69 | OH | H | H | 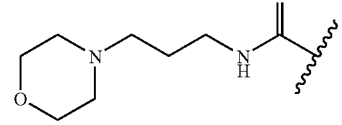 |
| Example 70 | H | 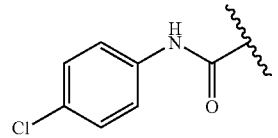 [SMILES: *C(=O)Nc1ccc(Cl)cc1] | H | H |
| Example 71 | H | 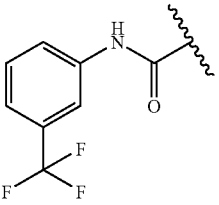 [SMILES: *C(=O)Nc1cccc(C(F)(F)F)c1] | H | H |
| Example 72 | H | 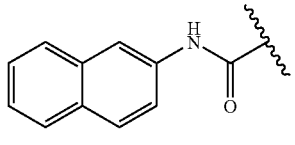 [SMILES: *C(=O)Nc1ccc2ccccc2c1] | H | H |
| Example 73 | H | 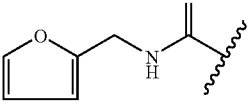 | H | H |
| Example 74 | H | 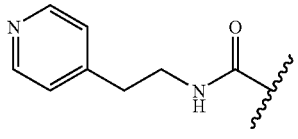 [SMILES: *C(=O)NCCc1ccncc1] | H | H |
| Example 75 | H | 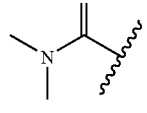 | H | H |
| Example 76 | H | 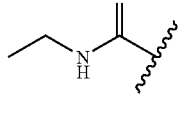 | H | H |
| Example 77 | H | 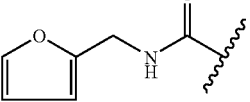 | H | H |
| Example 78 | OH | H | H | 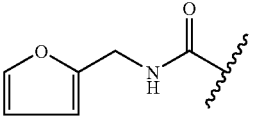 [SMILES: *C(=O)NCc1ccco1] |

TABLE 1-continued

| | | | | |
|---|---|---|---|---|
| Example 79 | H | benzyl-NHC(O)- | H | H |
| Example 80 | H | (pyridin-4-yl)methyl-NHC(O)- | H | H |
| Example 81 | H | (pyridin-3-yl)methyl-NHC(O)- | H | H |
| Example 82 | H | 2-(piperidin-1-yl)ethyl-NHC(O)- | H | H |
| Example 83 | H | 2-(morpholin-4-yl)ethyl-NHC(O)- | H | H |
| Example 84 | H | 2-hydroxyethyl-NHC(O)- | H | H |
| Example 85 | H | 3-(morpholin-4-yl)propyl-NHC(O)- | H | H |
| Example 86 | H | COOCH$_3$ | H | H |
| Example 87 | H | COOCH$_3$ | H | H |
| Example 88 | H | COOCH$_3$ | H | H |
| Example 89 | H | CH$_3$ | H | H |
| Example 90 | H | CH$_3$ | H | H |
| Example 91 | H | COOCH$_3$ | H | H |
| Example 92 | H | COOCH$_3$ | H | H |
| Example 93 | H | COOCH$_3$ | H | H |
| Example 94 | H | COOCH$_3$ | H | H |
| Example 95 | H | COOH | H | H |
| Example 96 | H | COOH | H | H |
| Example 97 | H | COOH | H | H |
| Example 98 | H | COOH | H | H |
| Example 99 | H | COOH | H | H |
| Example 100 | H | COOH | H | H |

TABLE 1-continued
| Example 101 | H | 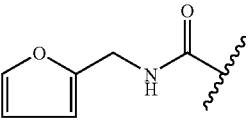 [SMILES: *C(=O)NCc1ccco1] | H | H |
| Example 102 | H | 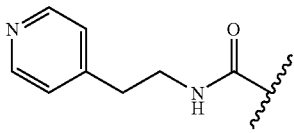 [SMILES: *C(=O)NCCc1ccncc1] | H | H |
| Example 103 | H | 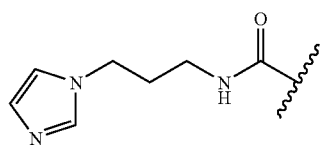 [SMILES: *C(=O)NCCCn1ccnc1] | H | H |
| Example 104 | H | 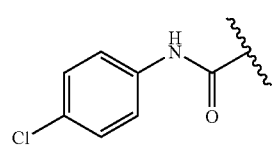 [SMILES: *C(=O)Nc1ccc(Cl)cc1] | H | H |
| Example 105 | H | 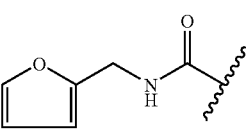 [SMILES: *C(=O)NCc1ccco1] | H | H |
| Example 106 | H | 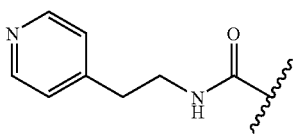 [SMILES: *C(=O)NCCc1ccncc1] | H | H |
| Example 107 | H | 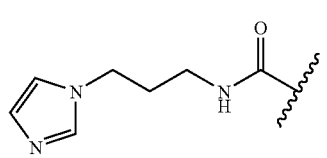 [SMILES: *C(=O)NCCCn1ccnc1] | H | H |
| Example 108 | H | 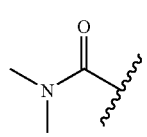 [SMILES: *C(=O)N(C)C] | H | H |
| Example 109 | H | 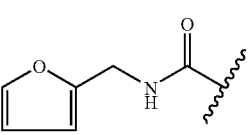 [SMILES: *C(=O)NCc1ccco1] | H | H |
| Example 110 | H | 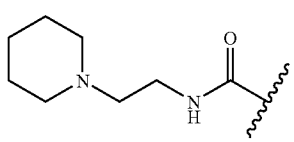 [SMILES: *C(=O)NCCN1CCCCC1] | H | H |
| Example 111 | H | 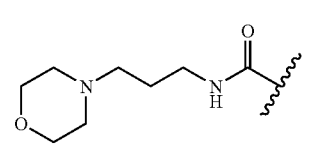 [SMILES: *C(=O)NCCCN1CCOCC1] | H | H |
| Example 112 | H | $CONH_2$ | H | H |

TABLE 1-continued

| | | | | | |
|---|---|---|---|---|---|
| Example 113 | H | CONH$_2$ | | H | H |
| Example 114 | H | CONH$_2$ | | H | H |
| Example 115 | H | CONH$_2$ | | H | H |
| Example 116 | H | CONH$_2$ | | H | H |
| Example 117 | H | CONH$_2$ | | H | H |
| Example 118 | H | CONH$_2$ | | H | H |
| Example 119 | H | CONH$_2$ | | H | H |
| Example 120 | H | CONH$_2$ | | H | H |
| Example 121 | H | CONH$_2$ | | H | H |
| Example 122 | H | CONH$_2$ | | H | H |
| YC-1 | | | | | |

| | | $R_5$ | $R_6$ | $R_7$ | X | Y | HepG2 % HIF (10 μmol) | AGS % HIF (10 μmol) | Hep3B IC$_{50}$ (μM) | AGS IC$_{50}$ (μM) |
|---|---|---|---|---|---|---|---|---|---|---|
| | Example 1 | adamantyl | H | H | C | C | 35.50 | 14.2 | — | — |
| | Example 2 | adamantyl | H | H | C | C | −0.50 | 42.7 | 9.9 | 7.4 |
| | Example 3 | adamantyl | H | H | C | C | 7.39 | 32.3 | — | — |
| | Example 4 | adamantyl | H | H | C | C | 71.30 | 61.3 | — | — |
| | Example 5 | adamantyl | H | H | C | C | 110.30 | 6.5 | — | — |
| | Example 6 | adamantyl | H | H | C | C | 64.90 | 79.9 | — | — |
| | Example 7 | adamantyl | H | H | C | C | 48.00 | 72.7 | — | — |
| | Example 8 | tert-butyl | H | H | C | C | 83.00 | 43.3 | — | — |
| | Example 9 | F | H | H | C | C | — | 109.8 | — | — |
| | Example 10 | Cl | H | H | C | C | 40.80 | 22.0 | — | — |
| | Example 11 | Cl | Cl | H | C | C | −23.20 | 71.0 | — | — |
| | Example 12 | Cl | Cl | H | C | C | −39.90 | 63.0 | — | — |
| | Example 13 | Cl | Cl | H | C | C | 76.20 | 133.0 | — | — |

TABLE 1-continued

| | | | | | | | | | |
|---|---|---|---|---|---|---|---|---|---|
| Example 14 | Cl | Cl | Cl | C | C | −21.90 | 32.0 | — | — |
| Example 15 | Br | H | H | C | C | 35.95 | 52.0 | — | — |
| Example 16 | I | H | H | C | C | 72.03 | 45.0 | — | — |
| Example 17 | H₃C-C(=O)- | H | H | C | C | 116.80 | 74.0 | — | — |
| Example 18 | adamantyl | H | H | C | C | 27.11 | −5.6 | 2.6 | 0.7 |
| Example 19 | tert-butyl | H | H | C | C | −32.00 | 3.0 | — | — |
| Example 20 | phenyl | H | H | C | C | 69.90 | 40.4 | — | — |
| Example 21 | adamantyl | H | H | C | C | 87.20 | 43.5 | — | — |
| Example 22 | NO₂ | H | H | C | C | 144.50 | 76.0 | — | — |
| Example 23 | adamantyl | H | H | C | C | 20.20 | −9.6 | 4.3 | 1.0 |
| Example 24 | Cl | Cl | H | C | C | −15.70 | 14.0 | — | — |
| Example 25 | Cl | Cl | Cl | C | C | −8.50 | 10.0 | — | — |
| Example 26 | Br | H | H | C | C | −16.60 | 8.8 | — | — |
| Example 27 | Br | Cl | H | C | C | −29.80 | 12.0 | — | — |
| Example 28 | I | H | H | C | C | — | 65.0 | — | — |
| Example 29 | H | H | H | C | C | 123.00 | 100.0 | — | — |
| Example 30 | tert-butyl | H | H | C | C | 115.00 | 133.0 | >30 | >30 |
| Example 31 | CH₃ | H | H | C | C | — | 127.0 | >30 | >30 |
| Example 32 | NO₂ | H | H | C | C | 102.00 | 103.0 | >30 | >30 |
| Example 33 | adamantyl | H | H | C | C | 14.90 | −11.2 | — | — |
| Example 34 | adamantyl | H | H | C | C | 121.70 | 14.3 | — | — |
| Example 35 | adamantyl | H | H | C | C | 94.50 | 66.0 | — | — |

TABLE 1-continued

| | | | | | | | | | |
|---|---|---|---|---|---|---|---|---|---|
| Example 36 | Cl | Cl | H | C | C | −30.40 | 34.0 | — | — |
| Example 37 | adamantyl | H | H | C | C | 55.80 | 71.0 | — | — |
| Example 38 | adamantyl | H | H | C | C | −21.30 | −10.4 | — | — |
| Example 39 | Cl | Cl | H | C | C | 4.30 | 28.5 | — | — |
| Example 40 | Cl | Cl | H | C | C | 18.30 | 121.0 | — | — |
| Example 41 | Cl | Cl | H | C | C | 30.20 | 109.0 | — | — |
| Example 42 | adamantyl | H | H | C | C | 59.30 | 57.0 | — | — |
| Example 43 | adamantyl | H | H | C | C | 79.80 | −4.0 | — | — |
| Example 44 | adamantyl | H | H | C | C | −3.40 | −3.0 | 5 | 2.5 |
| Example 45 | adamantyl | H | H | C | C | 50.80 | 97.3 | — | — |
| Example 46 | adamantyl | H | H | C | C | 28.20 | −6.0 | — | — |
| Example 47 | t-butyl | H | H | C | C | 37.80 | 43.0 | 29 | 9.5 |
| Example 48 | adamantyl | H | H | C | C | — | −8.3 | 0.4 | 0.35 |
| Example 49 | t-butyl | H | H | C | C | −32.30 | NA | — | — |

TABLE 1-continued

| | | | | | | | | | |
|---|---|---|---|---|---|---|---|---|---|
| Example 50 | adamantyl | H | H | C | C | 39.30 | 56.0 | — | — |
| Example 51 | F | H | H | C | C | 95.50 | 37.3 | >30 | >30 |
| Example 52 | Cl | H | H | C | C | 42.80 | 48.4 | >30 | 10 |
| Example 53 | Cl | Cl | H | C | C | — | 4.3 | — | — |
| Example 54 | Cl | Cl | H | C | C | −38.10 | 55.0 | — | — |
| Example 55 | Cl | Cl | H | C | C | 31.10 | 57.4 | — | — |
| Example 56 | Cl | Cl | Cl | C | C | −23.90 | 71.0 | — | — |
| Example 57 | Br | H | H | C | C | 18.70 | 16.2 | >30 | 1.6 |
| Example 58 | I | H | H | C | C | 50.30 | 31.6 | 7.2 | 3.5 |
| Example 59 | phenyl | H | H | C | C | 27.20 | 54.0 | — | — |
| Example 60 | H₃C-C(=O)- | H | H | C | C | 66.20 | 77.0 | >30 | >30 |
| Example 61 | adamantyl | H | H | C | C | 113.30 | 103.0 | — | — |
| Example 62 | Cl | Cl | H | C | C | 51.08 | 114.0 | — | — |
| Example 63 | Cl | Cl | H | C | C | −23.40 | 62.0 | — | — |
| Example 64 | Cl | Cl | H | C | C | −22.50 | 82.0 | — | — |
| Example 65 | adamantyl | H | H | C | C | 88.90 | 140.0 | >30 | 1.5 |
| Example 66 | adamantyl | H | H | C | C | 54.70 | — | >30 | >30 |
| Example 67 | adamantyl | H | H | C | C | 86.90 | 40.0 | 12.6 | 5.9 |
| Example 68 | adamantyl | H | H | C | C | — | — | 51.7 | 3.0 |
| Example 69 | adamantyl | H | H | C | C | — | — | >30 | >30 |

TABLE 1-continued

| | | | | | | | | | |
|---|---|---|---|---|---|---|---|---|---|
| Example 70 | adamantyl | H | H | C | C | 74.30 | 49.0 | >30 | 9.5 |
| Example 71 | adamantyl | H | H | C | C | 8.20 | 57.0 | — | — |
| Example 72 | adamantyl | H | H | C | C | 113.30 | 46.0 | >30 | >30 |
| Example 73 | adamantyl | H | H | C | C | 21.20 | 4.4 | 14.06 | 2.0 |
| Example 74 | adamantyl | H | H | C | C | 5.96 | 8.1 | 8.2 | 3.1 |
| Example 75 | Cl | Cl | H | C | C | 151.30 | 136.0 | — | — |
| Example 76 | Cl | Cl | H | C | C | 80.00 | 90.0 | — | — |
| Example 77 | Cl | Cl | H | C | C | −11.80 | 19.0 | >30 | 35 |
| Example 78 | Cl | Cl | H | C | C | 47.20 | 73.0 | 23.2 | >30 |
| Example 79 | Cl | Cl | H | C | C | 28.70 | 19.0 | — | — |
| Example 80 | Cl | Cl | H | C | C | 46.40 | 44.0 | — | — |
| Example 81 | Cl | Cl | H | C | C | 49.40 | 110.0 | — | — |
| Example 82 | Cl | Cl | H | C | C | 74.50 | 46.0 | — | — |
| Example 83 | Cl | Cl | H | C | C | 51.80 | 42.0 | — | — |
| Example 84 | Cl | Cl | H | C | C | 65.10 | 139.0 | — | — |
| Example 85 | Cl | Cl | H | C | C | 110.50 | 110.0 | — | — |
| Example 86 | adamantyl | H | H | N | C | −24.50 | 3.8 | 1.2 | 2 |
| Example 87 | adamantyl | H | H | C | N | 100.60 | 33.0 | 5.9 | 5 |
| Example 88 | Cl | Cl | H | C | N | — | 88.0 | — | — |
| Example 89 | adamantyl | H | H | N | C | 55.70 | 52.0 | — | — |

TABLE 1-continued

| | | | | | | | | | |
|---|---|---|---|---|---|---|---|---|---|
| Example 90 | Cl | Cl | H | N | C | — | -17.7 | — | — |
| Example 91 | Cl | Cl | H | N | C | — | 2.3 | — | — |
| Example 92 | Cl | Cl | Cl | N | C | -22.97 | 17.0 | — | — |
| Example 93 | Br | Cl | H | N | C | -36.00 | 5.7 | — | — |
| Example 94 | *tBu* | | H | H | N | C | 5.40 | 9.6 | — | — |
| Example 95 | Cl | Cl | H | N | C | -30.90 | -2.0 | — | — |
| Example 96 | *adamantyl* | | H | H | C | N | 62.70 | 73.0 | — | — |
| Example 97 | Cl | Cl | H | C | N | 78.90 | 60.0 | — | — |
| Example 98 | *adamantyl* | | H | H | N | C | -24.50 | 13.0 | 1.03 | — |
| Example 99 | Br | Cl | H | N | C | -32.30 | -6.0 | — | — |
| Example 100 | *tBu* | | H | H | N | C | 4.20 | 2.0 | — | — |
| Example 101 | *adamantyl* | | H | H | C | N | 68.40 | 108.0 | — | — |
| Example 102 | *adamantyl* | | H | H | C | N | 65.98 | 5.4 | >10 | 1.3 |
| Example 103 | *adamantyl* | | H | H | C | N | -7.70 | -2.3 | — | >10 |
| Example 104 | *adamantyl* | | H | H | C | N | 32.30 | 59.0 | — | 18.6 |
| Example 105 | *adamantyl* | | H | H | N | C | 31.70 | 130.0 | >10 | >10 |
| Example 106 | *adamantyl* | | H | H | N | C | 71.90 | 33.0 | — | 2.1 |

TABLE 1-continued

| | | | | | | | | | | |
|---|---|---|---|---|---|---|---|---|---|---|
| Example 107 | adamantyl | H | H | N | C | 10.20 | 48.0 | — | 11 |
| Example 108 | Cl | Cl | H | N | C | 17.60 | 92.0 | — | — |
| Example 109 | Cl | Cl | H | N | C | −30.00 | 9.0 | — | — |
| Example 110 | Cl | Cl | H | N | C | −22.90 | 28.4 | — | — |
| Example 111 | Cl | Cl | H | N | C | 7.10 | 93.0 | — | — |
| Example 112 | adamantyl | H | H | C | N | 67.10 | −35.9 | — | 0.9 |
| Example 113 | adamantyl | H | H | N | C | −24.10 | 34.0 | 3.1 | 3.0 |
| Example 114 | F | H | H | N | C | 107.00 | 103.0 | — | — |
| Example 115 | Cl | Cl | H | N | C | −45.20 | −2.0 | — | — |
| Example 116 | Cl | Cl | Cl | N | C | −36.40 | −5.5 | — | — |
| Example 117 | Br | H | H | N | C | −24.00 | 3.4 | — | — |
| Example 118 | Br | Cl | H | N | C | −39.00 | −6.0 | — | — |
| Example 119 | tert-butyl | H | H | N | C | −30.00 | 7.6 | — | — |
| Example 120 | CH$_3$ | H | H | N | C | −24.80 | 25.0 | — | — |
| Example 121 | H | H | H | N | C | 122.00 | 87.3 | — | — |
| Example 122 | NO$_2$ | H | H | N | C | 103.00 | 136.0 | — | — |
| YC-1 | | | | | | −0.21 | 22.4 | 13.8 | 2.0 |

| | R$_8$ (5-position) | R$_8$ (6-position) | R$_9$ | R$_{10}$ | Z | Hep3B % HIF (30 μmol) | AGS % HIF (10 μmol) |
|---|---|---|---|---|---|---|---|
| Example 123 | COOCH$_3$ | H | Cl | Cl | O | −7.9 | 43.4 |
| Example 124 | COOCH$_3$ | H | adamantyl | H | O | 2.2 | 87.0 |
| Example 125 | H | COOCH$_3$ | adamantyl | H | O | 21.6 | 93.0 |
| Example 126 | H | COOCH$_3$ | adamantyl | H | NH | 2.9 | 91.0 |
| Example 127 | H | COOCH$_3$ | Cl | Cl | O | 68.5 | 20.4 |
| Example 128 | H | COOCH$_3$ | Cl | Cl | NH | 81.4 | 43.3 |
| Example 129 | H | COOCH$_3$ | tert-butyl | H | O | | |

TABLE 1-continued

| Example | | | | | | | |
|---|---|---|---|---|---|---|---|
| Example 130 | H | COOCH₃ | (tert-butyl) | H | NH | −59.3 | 28.1 |
| Example 131 | H | COOCH₃ | NO₂ | H | NH | 98.0 | −2.5 |
| Example 132 | H₂N-SO₂- | H | Cl | Cl | O | −0.9 | 120.0 |
| Example 133 | COOH | H | Cl | Cl | O | 33.4 | 67.3 |
| Example 134 | COOH | H | (adamantyl) | H | O | 58.7 | 82.0 |
| Example 135 | H | COOH | (adamantyl) | H | O | −49.5 | 39.2 |
| Example 136 | H | COOH | (adamantyl) | H | NH | 76.4 | 116.0 |
| Example 137 | H | COOH | Cl | Cl | O | 13.7 | 31.0 |
| Example 138 | H | COOH | Cl | Cl | NH | 95.7 | 121.0 |
| Example 139 | H | COOH | (tert-butyl) | H | O | 118.0 | 45.0 |
| Example 140 | H | COOH | (tert-butyl) | H | NH | 89.7 | 95.7 |
| Example 141 | H | COOH | NO₂ | H | NH | 89.7 | 91.3 |
| Example 142 | CONH₂ | H | (adamantyl) | H | O | 78.0 | 71.8 |
| Example 143 | (CH₃)₂N-C(O)- | H | (adamantyl) | H | O | 11.2 | 64.0 |
| Example 144 | (furan-2-yl-CH₂-NH-C(O)-) | H | (adamantyl) | H | O | 69.9 | 79.0 |
| Example 145 | ((CH₃)₂N-CH₂CH₂-NH-C(O)-) | H | (adamantyl) | H | O | −78.0 | −2.3 |

TABLE 1-continued

| | | | | | | | |
|---|---|---|---|---|---|---|---|
| Example 146 | piperidinyl-CH2CH2-NHC(O)-~ | H | adamantyl-~ | H | O | −78.0 | −2.8 |
| Example 147 | morpholinyl-CH2CH2CH2-NHC(O)-~ | H | adamantyl-~ | H | O | −77.2 | −2.8 |
| Example 148 | furan-2-yl-CH2-NHC(O)-~ | H | | Cl | Cl | O | −1.4 | 106.0 |
| Example 149 | H | furan-2-yl-CH2-NHC(O)-~ | adamantyl-~ | H | O | −38.0 | 52.0 |
| Example 150 | H | furan-2-yl-CH2-NHC(O)-~ | Cl | Cl | O | 4.2 | 143.0 |
| Example 151 | H | CONH2 | adamantyl-~ | H | NH | −69.1 | 70.0 |
| Example 152 | H | (CH3)2N-C(O)-~ | adamantyl-~ | H | NH | −6.3 | ND |
| Example 153 | H | furan-2-yl-CH2-NHC(O)-~ | adamantyl-~ | H | NH | 12.9 | 73.0 |
| Example 154 | H | (CH3)2N-CH2CH2-NHC(O)-~ | adamantyl-~ | H | NH | −78.0 | −3.4 |
| Example 155 | H | imidazol-1-yl-CH2CH2CH2-NHC(O)-~ | adamantyl-~ | H | NH | 77.5 | 120.7 |
| Example 156 | H | CONHNH2 | Cl | Cl | NH | 113.0 | 85.0 |
| Example 157 | H | furan-2-yl-CH2-NHC(O)-~ | Cl | Cl | NH | −4.6 | 108.0 |
| YC-1 | | | | | | 102.6 | 22.4 |

In another embodiment, the present invention pertains to a method for preparing the compounds of Chemical Formula 1A and 1B.

Representative compounds of the present invention can be synthesized according to Reaction Schemes 1 to 6, which are the mother models from which all of the compounds of the present invention can be derived by modifying reaction conditions, including reagents, solvents, the order of the reaction steps, and the like.

The synthesis of compounds of Chemical Formula 1A can be achieved through the coupling reaction shown in Reaction Scheme 1.

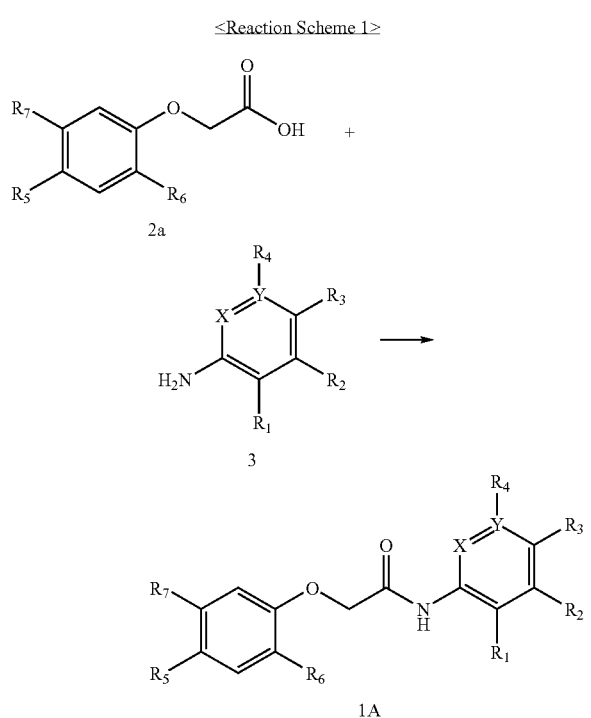

(wherein $R_1$~$R_7$, X and Y are each as defined in Chemical Formula 1A.)

In more detail, the coupling reaction starts with phenoxyacetic acid (2a) and an amine compound (3). These starting materials are condensed into the compound of Chemical Formula 1A in the presence of a Hunig base with the aid of a coupling agent in an organic solvent. Diisopropylamine (DIPEA) or triethylamine (TEA) may be used as a Hunig base for this reaction. The coupling agent useful in the present invention is selected from a group consisting of 1-[3(dimethylamino)propyl]-3-ethylcarbodiimide hydrochloride (EDC), O-benzotriazole-N,N,N',N'-tetramethyl-uronium-hexafluoro-phosphate (HBTU), 1-hydroxybenzotriazole (HOBt), benzotriazol-1-yl-oxy-tris-pyrrolidino-phosphonium hexafluorophosphate (PyBOP), 1-hydroxy-7-azabenzotriazole (HOAt) and combinations thereof. A preferable organic solvent is dimethylformamide (DMF) or methylenechloride ($CH_2Cl_2$).

When the $R_4$ moiety of Chemical Formula 1A is COORa in Reaction Scheme 1, it can be further modified, as seen in Reaction Scheme 2.

In Reaction Scheme 2, compounds of Chemical Formula 1Aa, 1Ab and 1Ac all correspond to those of Chemical Formula 1A.

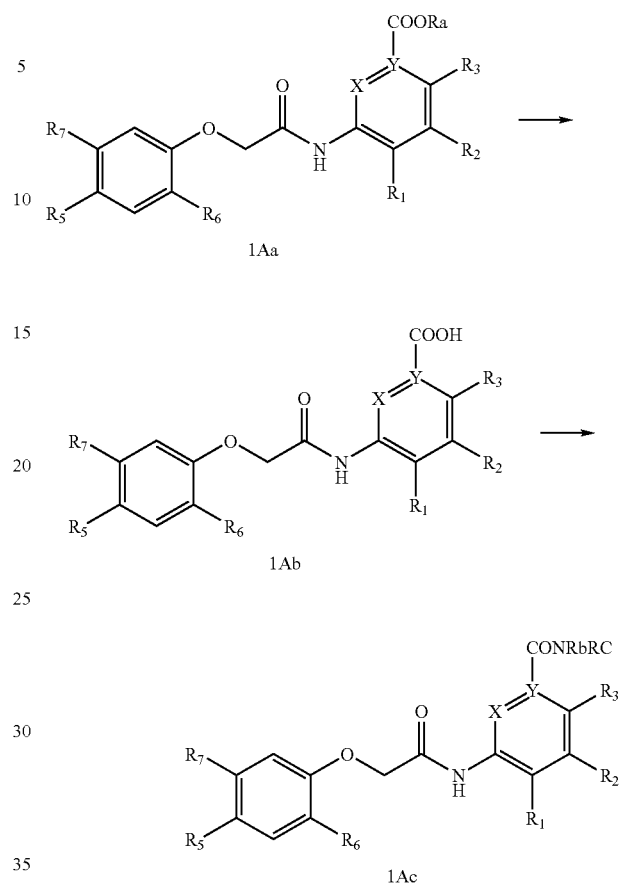

(wherein $R_1$~$R_3$, $R_5$~$R_7$, X, Y, Ra, Rb and Rc are each as defined in Chemical Formula 1A.)

Below, a more detailed description is given of the reactions of Reaction Scheme 2.

1) The compound of Chemical Formula 1Aa can be reacted with an inorganic base in a mixture of an organic solvent and water to synthesize the corresponding carboxylic acid compound of Chemical Formula 1Ab. The organic solvent useful for this reaction may be tetrahydrofuran, dioxane, methanol or ethanol, and the inorganic base may be selected from among sodium lithianide? and sodium hydroxide. This reaction is preferably conducted at 25~50° C.

2) The compound of Chemical Formula 1Ab can be converted into a corresponding amide compound of Chemical Formula 1Ac through reaction with ammonium chloride or alkyl amine in the presence of a Hunig base and a coupling agent in an organic solvent at room temperature (25° C.) or under a flux condition. The coupling agent useful for this reaction is selected from among EDC, HOBt; PyBOP and combinations thereof DIPEA or TEA is useful as the Hunig base. The organic solvent is preferably DMF.

When the $R_2$ moiety of Chemical Formula 1A is COORa or CONRbRc in Reaction Scheme 1, it can be synthesized according to Reaction Scheme 3, below.

In Reaction Scheme 3, the compounds of Chemical Formula 1Ad, 1Ae and 1Af all correspond to those of Chemical Formula 1A.

<Reaction Scheme 3>

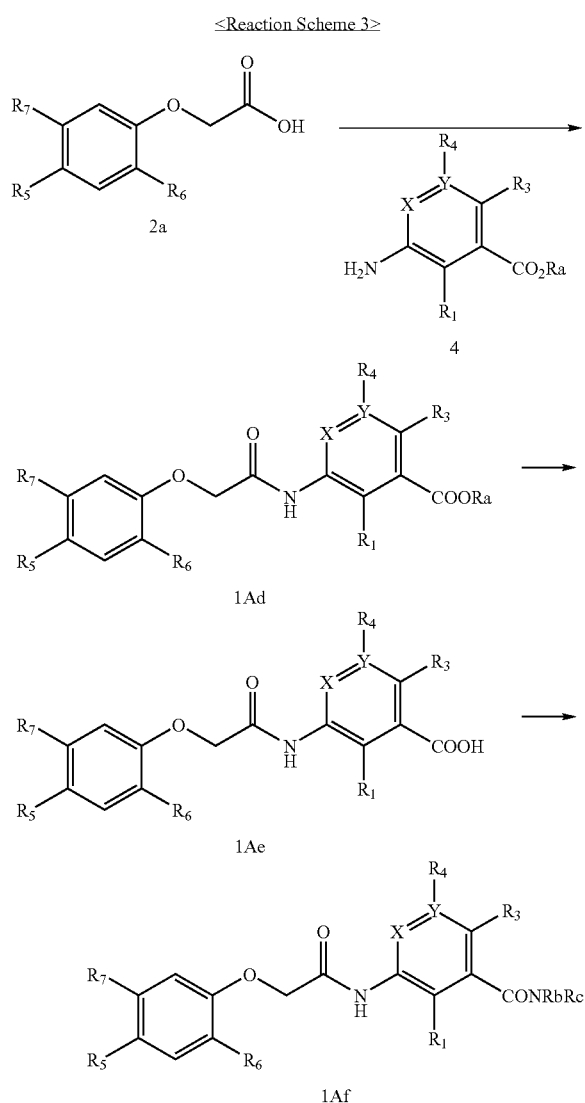

(wherein, $R_1$, $R_3\sim R_7$, X, Y, Ra, Rb and Rc are each as defined in Chemical Formula 1A.)

Detailed reaction steps are described as follows.

1) A phenoxy acetic acid (2a) is reacted with an amine compound (4) in the presence of a coupling agent in an organic solvent to yield a carboxylic acid ester compound (1Ad). Suitable is a coupling agent selected from among PyBOP, EDC, HOBt, 4-dimethylaminopyridine (DMAP), and combinations thereof. This reaction is preferably conducted at 25° C., with DMF serving as an organic solvent.

2) The carboxylic acid ester compound (1Ad) is converted into a corresponding carboxylic acid compound (1Ae) in the presence of lithium iodide in an organic solvent, such as pyridine, $CH_2Cl_2$ or DMF, under reflux.

3) The compound (1Ae) is reacted with ammonium chloride or alkyl amine using a coupling agent in DMF at room temperature (25° C.) or under reflux, thereby producing an amide compound (1Af). Useful is a coupling agent selected from among DMAP, PyBOP, EDC, HOBt and combinations thereof.

In the case that the $R_2$ moiety of Chemical Formula 1A is $CONH_2$, synthesis thereof can be achieved via the route shown in Reaction Scheme 4, below.

The compound of Chemical Formula 1Ag falls into the range of compounds of Chemical Formula 1A.

<Reaction Scheme 4>

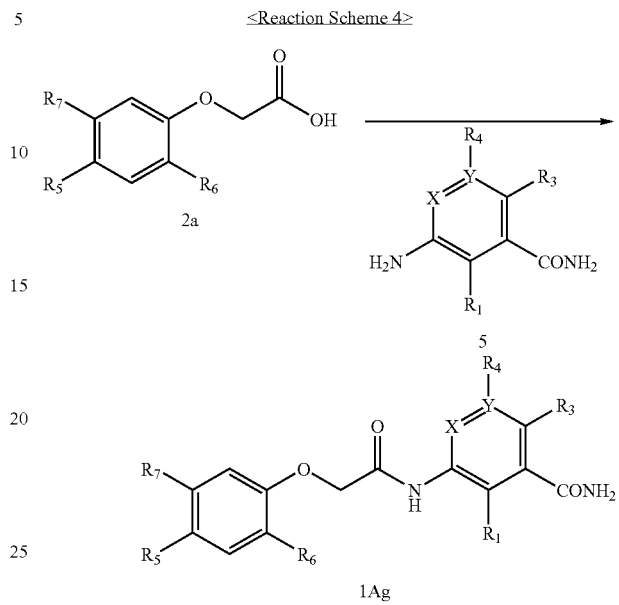

(wherein $R_1$, $R_3\sim R_7$, X and Y are each as defined in Chemical Formula 1A.)

In more detail, a phenoxy acetic acid (2a) is reacted with an amine compound (5) in the presence of a coupling agent in an organic solvent to yield a compound (1Ag). PyBOP or DMAP is preferably used as the coupling agent. DMF is a preferable solvent for this reaction, and a temperature of 25° C. may be set to elicit the desired reaction result.

The compound of Chemical Formula 1B can be synthesized according to Reaction Scheme 5, below.

<Reaction Scheme 5>

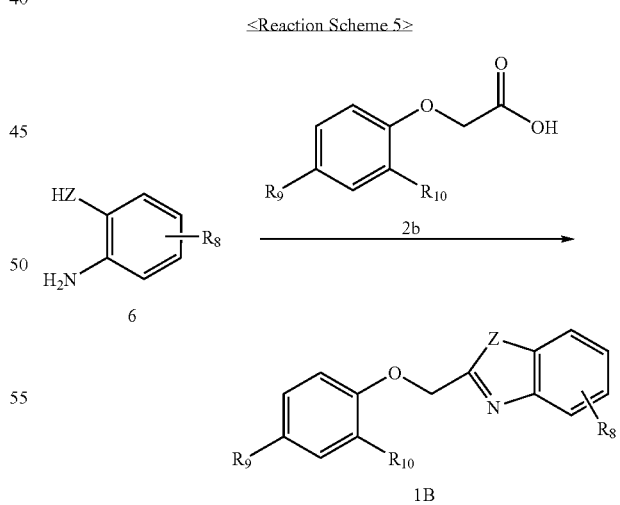

(wherein, Z, $R_8$, $R_9$ and $R_{10}$ are each as defined in Chemical Formula 1B.)

In more detail, the compound of Chemical Formula 1B can be prepared by reacting the phenoxy acetic acid (2b), which is commercially available or can be readily prepared using a well know method, with a compound (6), which can be synthesized using a known method, at an equivalent ratio in the presence of triethylsilyl polyphosphate (PPSE). This reaction is preferably conducted at 140~160° C. for 2-4 hours.

$R_8$ of COORa in Reaction Scheme 5 could be obtained via the route of Reaction Scheme 6, below.

Compounds 1Ba, 1Bb and 1Bc of Reaction Scheme 6 are within the range of Chemical Formula 1B.

As used herein, the term "inhibition activity against HIF-1" or a phrase equivalent thereto means inhibiting all of the transcription of an HIF-1 gene, the expression of HIF-1 protein, and the accumulation of HIF-1 protein.

The compounds of the present invention were found to have excellent inhibition activity against HIF-1 transcription

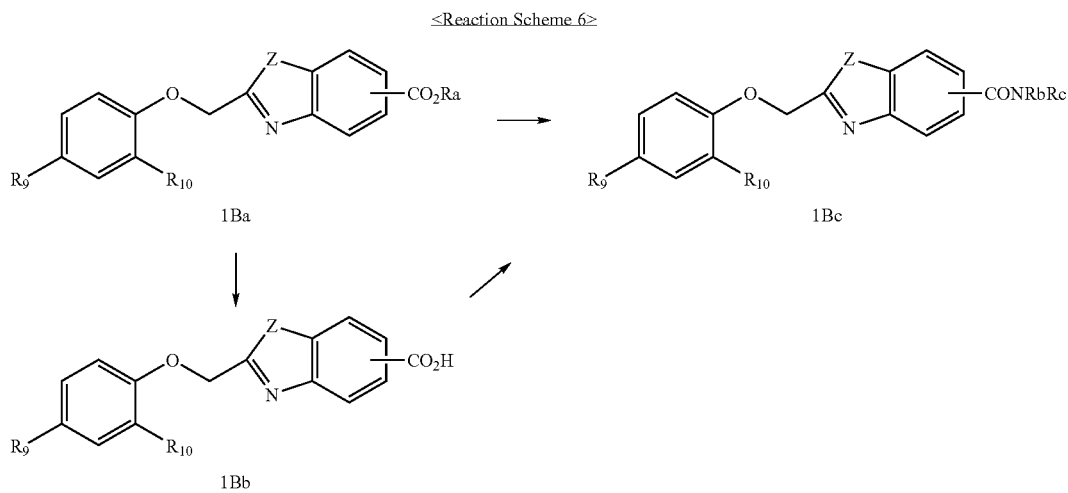

<Reaction Scheme 6>

(wherein, Z, $R_9$, $R_{10}$, Ra, Rb and Rc are each as defined in Chemical Formula 1B.)

A detailed description is given of Reaction Scheme 6, below.

1) An ester compound (1Ba) is hydrolyzed into a corresponding carboxylic acid compound (1Bb) in the presence of aluminum bromide and dimethyl sulfide, with $CH_2Cl_2$ serving as a solvent. This hydrolysis is preferably carried out at 25° C. for 2~3 hours. Alternatively, the conversion of the ester compound (1Ba) into the acid compound (1Bb) may be achieved in the presence of an acid under flux.

2) Either of the ester compound (1Ba) and the carboxylic acid compound (1Bb) can be used to prepare a corresponding amide compound (1Bc). A solution of commercially available alkyl amine in anhydrous toluene is stirred in the presence of triethyl aluminum (2M Hexane solution) at room temperature, preferably for approximately 30 min. To this mixture is added a solution of the compound (1Ba) in toluene, followed by fluxing at 80° C. to yield the compound (1Bc). The reaction time is preferably set at 1 to 2 hours. Alternatively, the compound (1Bc) may be synthesized through the reaction of the compound (1Bb) with an amine compound selected from among ammonium chloride, hydrazine and alkyl amine at room temperature (25° C.) in the presence of a coupling agent and a Hunig base in DMF. The coupling agent is selected from among EDC, HOBt, HATU, HBTU, and combinations thereof, and the Hunig base is DIPEA.

In accordance with a further embodiment, the present invention pertains to an anticancer pharmaceutical composition comprising the compound of Chemical Formula 1A or 1B, or a pharmaceutically acceptable salt as an active ingredient for the inhibition of HIF-1 activity.

The compound of Chemical Formula 1A or 1B, or a related pharmaceutical composition, exhibits anticancer activity no through general cytotoxicity, but through selective cytotoxicity characterized by inhibition activity against the transcription factor HIF-1, which plays a pivotal role in the growth and metastasis of cancer cells.

as measured in assays for HIF-1-mediated transcription in hypoxia. Therefore the compounds of the present invention can also have an inhibitory effect on the HIF-1 related expression of the genes involved in the malignant transformation of cancer, thereby suppressing the growth and metastasis of cancer. Consequently, the compounds of the invention can be used as active ingredients useful in the treatment and prevention of cancer.

As will be understood in Experimental Example 2, below, the compounds of the present invention can inhibit the expression of the HIF-1α protein in a dose-dependent manner in hypoxia without influencing the production of topoisomerase-1 (TOPO-1). In other words, the compounds of the present invention do not function through general cytotoxicity for anticancer activity, but show dose-dependent inhibition of the accumulation of HIF-1α protein, thereby suppressing the growth and metastasis of cancer with the minimal concomitant production of side effects.

In addition, as will be understood in Experimental Example 3, below, the compounds of the present invention can inhibit the expression of VEGF in a dose-dependent manner in hypoxia with no effect on the expression of the control gene GAPDH. Accordingly, the compounds of the present invention can be used for cancer therapy thanks to the ability thereof to suppress the growth and metastasis of cancer through selective inhibition activity against VEGF, a target gene of HIF-1, as well.

Having inhibition activity against HIF-1, therefore, the pharmaceutical composition of the present invention comprising the compound of Chemical Formula 1A and 1B or a pharmaceutically acceptable salt thereof can be used as a therapeutic for various cancerous disorders, including liver cancer, stomach cancer, breast cancer, colon cancer, bone cancer, pancreatic cancer, head or neck cancer, uterine cancer, ovarian cancer, rectal cancer, esophageal cancer, small intestine cancer, periproctic cancer; oviduct cancer; endometrial cancer; cervical cancer, vulva cancer, vagina cancer, Hodgkin's disease, prostate cancer, bladder cancer, kidney cancer, ureter cancer, renal cell carcinoma, renal pelvis cancer, and CNS tumors.

Also, the ability of the compound of Chemical Formula 1A or 1B, or a pharmaceutically acceptable salt thereof for inhibiting HIF-1 activity, ensures that the pharmaceutical composition can be effectively used in the treatment of diabetic retinopathy and arthritis.

As used herein, the term "inhibition of HIF-1 activity" or a phrase equivalent thereto means inhibiting all of the transcription of an HIF-1 gene, the expression of HIF-1 protein, and the accumulation of HIF-1 protein.

HIF-1 can be a target of drugs for the treatment of disorders which develop through angiogenesis. Particularly, the angiogenesis factors, such as VEGF, stimulated by HIF-1, which is activated in hypoxia, are implicated in the development of diabetic retinopathy or arthritis, such as rheumatoid arthritis. Diabetic retinopathy or arthritis can be aggravated as the expression of VEGF increases with the activation of HIF-1 in hypoxia. Accordingly, compounds capable of inhibiting the activity of HIF-1, which is activated in hypoxia, can be used as therapeutics for diabetic retinopathy or arthritis ((Eiji Ikeda, Pathology International, 2005, Vol 55, 603-610).

As will be shown in Experimental Example 3, the compounds of the present invention can inhibit the expression of VEGF in a dose-dependent manner in hypoxia without influencing the expression of the control gene GAPDH. Accordingly, the compounds of the present invention are useful as active ingredients for the treatment of diabetic retinopathy or arthritis, which is aggravated upon the expression of VEGF because they can selectively inhibit HIF-1, which plays a pivotal role in the expression of VEGF in hypoxia.

The pharmaceutical composition of the present invention may be formulated into oral or non-oral dosage forms. Examples of oral dosage forms include tablets, pills, hard/soft capsules, liquids, suspensions, emulsions, syrups, granules, elixirs, etc. These forms may include diluents (for example, lactose, dextrose, sucrose, mannitol, sorbitol, cellulose, and/or glycine), and/or lubricants (for example, silica, talc, stearic acid or magnesium or calcium salts thereof, and/or polyethylene glycol) in addition to the active ingredient. Tablets may also include binders, such as magnesium aluminum silicate, starch paste, gelatin, methyl cellulose, sodium carboxymethylcellulose and/or polyvinylpyrrolidone, and optionally disintegrants, such as starch, agar, alginic acid or sodium salt thereof, a boiling mixture, and/or absorbents, colorants, flavoring agents, and sweeteners.

Also, the pharmaceutical composition comprising the compound of Chemical Formula 1A or 1B or a pharmaceutically acceptable salt thereof in accordance with the present invention may be administered via non-oral routes. For this, the composition may be formulated into subcutaneous, intravenous, intramuscular, or intrathoracic injections. In order to obtain such non-oral dosage forms, the compound of Chemical Formula 1A or 1B or a pharmaceutically acceptable salt thereof may be mixed with a stabilizer or a buffer in water so as to afford a solution or a suspension which is then packaged into ampule or vial units.

Further, the composition is sterilized and/or may contain an auxiliary agent such as a preservative, a stabilizer, a wettable agent, an emulsifier, an osmotic pressure-controlling salt and a buffer, and/or other therapeutically effective materials. They may be mixed, granulized, or coated according to a method well known in the art. As an active ingredient) the compound of Chemical Formula 1A or 11 may be administered once or many times to mammals including humans, at a dose of 0.1 to 500 mg/g (body weight) a day, and preferably at a dose of 0.5 to 100 mg/g (body weight), via an oral or non-oral route.

MODE FOR INVENTION

A better understanding of the present invention may be obtained through the following examples which are set forth to illustrate, but are not to be construed as the limit of the present invention.

EXAMPLE 1

2-(4-Adamantan-1-yl-phenoxy)-N-3-methane-Sulfonyl-phenyl)-acetamide

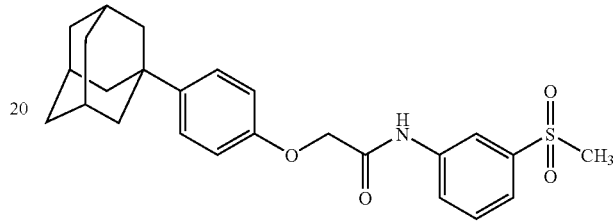

To a solution of (4-adamantan-1-yl-phenoxy)-acetic acid (50 mg, 0.17 mmol), 3-methanesulfonyl-phenylamine hydrochloride (54.39 mg, 0.26 mmol) and DIPEA (33.85 mg, 0.26 mmol) in DMF (2 mL) was added EDC (50.2 mg, 0.26 mmol) and HOBt (35.39 mg, 0.26 mmol) at room temperature. The reaction mixture was stirred at room temperature until completion and then poured into water (100 mL). The resulting solid was extracted with ethyl acetate, washed with brine, aqueous sodium bicarbonate and water, dried over anhydrous MgSO4, filtered and concentrated under reduced pressure. The resulting crude product was purified by flash chromatography on silica gel (Ethyl acetate:hexanes=2:8 to 4:6) to afford 2-(4-adamantan-1-yl-phenoxy)-N-(3-methanesulfonyl-phenyl)-acetamide as a colorless solid (0.61 g, 80% yield).

$^1$H NMR (CDCl$_3$, 300 MHz) 8.59 (1H, s, CONH), 8.09 (1H, m, aromatic), 8.05 (1H, d, J=7.8 Hz, aromatic), 7.7 (1H, d, J=8.1 Hz, aromatic), 7.54 (1H, m, aromatic), 7.33 (2H, m, aromatic), 6.94 (2H, m, aromatic), 4.61 (2H, s, —OCH$_2$), 3.05 (3H, s, —SO$_2$CH$_3$), 2.09 (3H, brs, adamantyl), 1.88 (6H, d, 2 J=2.4 Hz, adamantyl), 1.76 (6H, m, adamantyl).

EXAMPLE 2

3-[2-(4-Adaman-1-yl-phenoxy)-acetylamino]-benzoic acid methyl ester

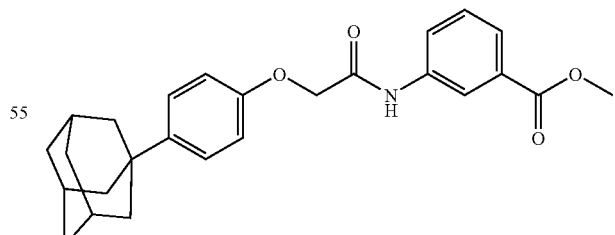

To a solution of the (4-adamantan-1-yl-phenoxy)-acetic acid (140 mg, 0.5 mmol) and 3-aminobenzoic acid methyl ester (110 mg, 0.75 mmol) in DMF (5.0 mL) were added 1-[3-(dimethylamino)propyl]-3-ethylcarbodiimide hydrochloride (EDC) (144.0 mg, 0.75 mmol), 1-hydroxybenzotriazole hydrate (HOBT) (101 mg, 0.75 mmol), and N,N-diisopropylethylamine (DIPEA) (0.13 mL, 0.75 mmol). The reaction mixture was stirred at room temperature overnight, and then partitioned between ethyl acetate and brine. The organic phase was dried (MgSO4 anh), and concentrated. Purification by silica gel column chromatography (n-Hexane:Ethyl acetate:MeOH=15:3:1) gave 3-[2-(4-Adamant-1-yl-phenoxy)-acetylamino]-benzoic acid methyl ester as a white solid (160 mg, 76% yield).

¹H-NMR (DMSO-d₆, 300 Hz) 10.31 (1H, s, NH), 8.34 (1H, m, aromatic), 7.89 (1H, m, aromatic), 7.67 (1H, m, aromatic), 7.47 (1H, ps t, J=7.8H aromatic), 7.28 (2H, m, aromatic), 6.93 (2H, m, aromatic), 4.62 (2H, s, OCH₂CO), 3.85 (3H, s, OCH₃), 2.03 (3H, m, adamantyl), 1.81-1.82 (6H, m, adamantyl), 1.71 (6H, m, adamantyl).

EXAMPLE 3

3-[2-(4-adamantan-1-yl-phenoxy)-acetylamino]-benzoic acid ethyl ester

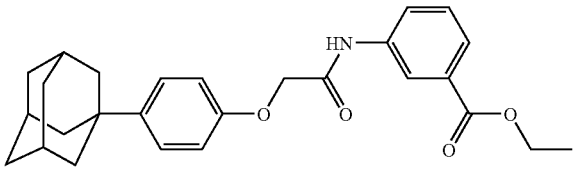 [SMILES: CCOC(=O)c1cccc(NC(=O)COc2ccc(C34CC5CC(CC(C5)C3)C4)cc2)c1]

To a mixture of [4-(1-adamantyl)phenoxy]acetic acid (143.2 mg, 0.5 mmol), 3-aminobenzoic acid ethyl ester (123.9 mg, 0.5 mmol), N-(3-dimethylaminopropyl)-N'-ethyl carbodiimide HCl (EDC) (143.8 mg, 0.75 mmol) and 1-hydroxybenzotriazole (HOBt) (101.4 mg, 0.75 mmol) in DMF (6 mL) was added N,N-diisopropylethylamine, redistilled (DIPEA) (97.0 mg, 0.13 mL, 0.75 mmol). The mixture was stirred overnight, and then partitioned between ethyl acetate and 10% HCl. The organic phase was washed with brine, dried (MgSO4 anh), and concentrated. The residue was purified by silica gel flash column chromatography (n-Hexane:Ethyl acetate:MeOH=6:3:1) to give 3-[2-(4-adamantan-1-yl-phenoxy)-acetylamino]-benzoic acid ethyl ester as a white solid (194.4 mg, 89.7% yield).

¹H-NMR (CDCl3, 300 Hz) 8.42 (1H, s, NH), 8.02-8.06 (2H, m, aromatic), 7.82-7.85 (1H, m, aromatic), 7.44 (1H, ps-t, J=8.1 Hz, aromatic), 7.32-7.37 (2H, m, aromatic), 6.93-6.98 (2H, m, aromatic), 4.59 (2H, s, CH₂), 4.37 (2H, q, J=7.2 Hz, aromatic), 2.08 (3H, m, adamantyl), 1.88 (6H, m, adamantyl), 1.70-1.80 (6H, m, adamantyl), 1.39 (3H, t, J=7.5 Hz, CH₃).

EXAMPLE 4

{3-[2-(4-Adamantan-1-yl-phenoxy)-acetylamino]-phenyl}-acetic acid methyl ester

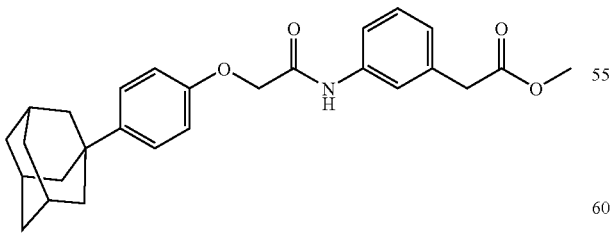

To a solution of the (4-adamantan-1-yl-phenoxy)-acetic acid (143 mg, 0.5 mmol) and (3-amino-phenyl)-acetic acid methyl ester (LMJ-I-57) (124 mg, 0.75 mmol) in DMF (5.0 mL) were added 1-[3-(dimethylamino)propyl]-3-ethylcarbodiimide hydrochloride (EDC) (144 mg, 0.75 mmol), 1-hydroxybenzotriazole hydrate (HOBT) (101 mg, 0.75 mmol), and N,N-disopropylethylamine (DIPEA) (0.13 mL, 0.75 mmol). The reaction mixture was stirred at room temperature overnight, and then partitioned between ethyl acetate and brine. The organic phase was dried (MgSO₄ anh), and concentrated. Purification by silica gel column chromatography (CH₂Cl₂:MeOH=40:1) gave {3-[4-adamantan-1-yl-phenoxy)-acetylamino]-phenyl}-acetic acid methyl ester as a white solid (208.8 mg, 99.9% yield).

¹H-NMR (CDCl₃, 300 Hz) 8.27 (1H, s, NH), 7.51 (2H, m, aromatic), 7.23-7.35 (3H, m, aromatic), 7.04 (1H, d, J=7.2 Hz aromatic), 6.91 (2H, m, aromatic), 4.55 (2H, s, OCH₂CO), 3.66 (3H, s, COCH₃), 3.60 (2H, s, CH₂COOCH₃), 2.06 (3H, m, adamantyl), 1.86 (6H, m, adamantyl), 1.68-1.78 (6H, m, adamantyl).

EXAMPLE 5

4-[2-(4-Adamantan-1-yl-phenoxy)-acetylamino]-benzoic acid methyl ester

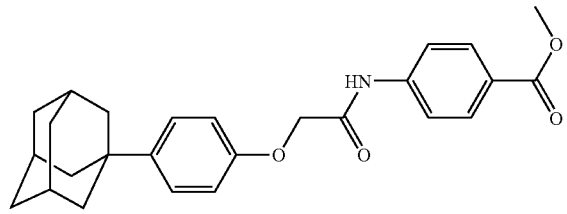 [SMILES: COC(=O)c1ccc(NC(=O)COc2ccc(C34CC5CC(CC(C5)C3)C4)cc2)cc1]

To a mixture of [4-(1-adamantyl)phenoxy]acetic acid (143.2 mg, 0.5 mmol), 4-aminobenzoic acid methyl ester (113.4 mg, 0.5 mmol), N-3-dimethylaminopropyl)-N'-ethyl carbodiimide HCl (EDC) (143.8 mg, 0.75 mmol) and 1-hydroxybenzothiazole (HOBt) (101.4 mg, 0.75 mmol) in DMF (6 mL) was added N,N-diisopropylethylamine, redistilled (DIPEA) (97.0 mg, 0.13 mL, 0.75 mmol). The mixture was stirred overnight, and then partitioned between ethyl acetate and 10% HCl. The organic phase was washed with brine, dried (MgSO₄ anh), and concentrated. The residue was purified by silica gel flash column chromatography (n-Hexane:Ethyl acetate:MeOH=6:3:1) to give 4-[2-(4-Adamantan-1-yl-phenoxy)-acetylamino]-benzoic acid methyl ester as a white solid (108.3 mg, 51.7% yield).

¹HNMR (CDCl₃, 300 Hz) 8.46 (1H, s, NH), 8.04 (2H, d, J=21.3 Hz, aromatic-H), 7.69 (2H, d, J=9.3 Hz, aromatic-H), 7.34 (2H, d, J=8.7 Hz, aromatic-H), 6.94 (2H, d, J=8.7 Hz, aromatic-H), 4.61 (2H, s, CH₂), 3.90 (3H, s, CH₃), 1.75-2.09 (15H, m, adamantly-H).

EXAMPLE 6

2-[2-(4-adamantan-1-yl-phenoxy)-acetylamino]-benzoic acid methyl ester

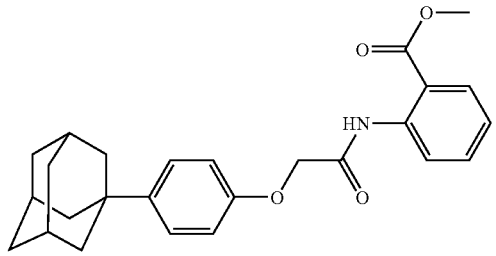 [SMILES: COC(=O)c1ccccc1NC(=O)COc1ccc(C23CC4CC(CC(C4)C2)C3)cc1]

To a mixture of [4-(1-adamantyl)phenoxy]acetic acid (85.9 mg, 0.30 mmol), 2-amino-benzoic acid methyl ester (0.07 mL, 0.54 mmol), N-(3-dimethylaminopropyl)-N'-ethyl carbodiimide HCl (EDC) (103.5 mg, 0.54 mmol) and 1-hydroxybenzotriazole (HOBt) (73.0 mg, 0.54 mmol) in DMF (3.6 mL) was added N,N-diisopropylethylamine, redistill (DIPEA) (69.8 mg, 0.10 mL, 0.54 mmol). The mixture was stirred overnight, and then partitioned between ethyl acetate and 10% HCl. The organic phase was washed with brine, dried (MgSO$_4$ anh), and concentrated. The residue was purified by silica gel flash column chromatography (n-Hexane:Ethyl acetate:MeEOH=12:3:1) to give 2-[2-(4-adamantan-1-yl-phenoxy)-acetylamino]-benzoic acid methyl ester as a white solid (46.4 mg, 3.69% yield).

$^1$HNMR (CDCl$_3$, 300 Hz) 12.1 (1H, s, N), 8.79 (1H, d, J=8.7, aromatic-H), 8.05 (1H, dd, J=7.8 & 1.8 Hz, aromatic-H), 7.54-7.60 (1H, m, aromatic-H), 7.31-7.35 (2H, m, aromatic-H), 7.12-7.16 (2H, m, aromatic-H), 7.03-7.07 (2H, m, aromatic-H), 4.62 (2H, s, CH$_2$), 3.93 (3H, s, CH$_3$), 2.08 (3H, m, adamantly-H), 1.88 (6H, m, adamantly-H), 1.70 1.80 (6H, m, adamantly-H).

EXAMPLE 7

5-[2-(4-Adamantan-1-yl-phenoxy)-acetylamino]-isophthalic acid dimethyl ester

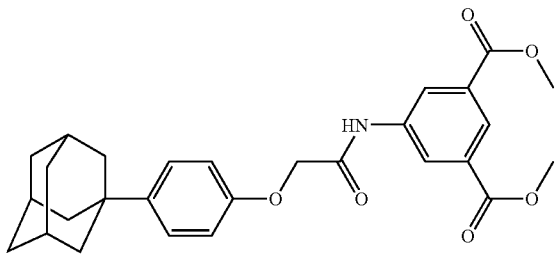 [SMILES: COC(=O)c1cc(NC(=O)COc2ccc(C34CC5CC(CC(C5)C3)C4)cc2)cc(C(=O)OC)c1]

To a mixture of (4-adamantan-1-yl-phenoxy)-acetic acid (143.2 mg, 0.50 mmol), 5-aminoisophthalic acid dimethyl ester (156.9 mg, 0.75 mmol), N-3-dimethylaminopropyl)-N'-ethyl carbodiimide HCl (EDC) (143.8 mg, 0.75 mmol) and 1-hydroxybenzotriazole (HOBt) (101.4 mg, 0.75 mmol) in DMF (5 mL) was added N,N-disopropylethylamine, redistilled (DIPEA) (0.13 mL, 0.75 mmol). The mixture was stirred overnight, and then partitioned between ethyl acetate and 10% HCl. The organic phase washed with brine, dried (MgSO$_4$ anh), and concentrated. The residue was purified by silica gel flash column chromatography (n-Hexane:Ethyl acetate:MeOH=9:3:1) to give 5-[2-(4-Adamantan-1-yl-phenoxy)-acetylamino]-isophthalic acid dimethyl ester as a light yellow solid (195.6 mg, 81.92% yield).

$^1$H-NMR (CDCl$_3$, 300 Hz) 8.47-8.48 (4H, m, aromatic-H, NH), 7.34-7.36 (2H, m, aromatic-H), 6.94-6.97 (2H, m, aromatic-H), 4.63 (2H, s, CH$_2$), 3.96 (6H, s, CH$_3$), 2.10 (3H, m, adamantly-H), 1.90 (6H, m, adamantly-H), 1.77 (6H, m, adamantly-H).

EXAMPLE 8

3-[2-(4-tert-butyl phenoxy)-acetyl-amino]-benzoic acid methyl ester

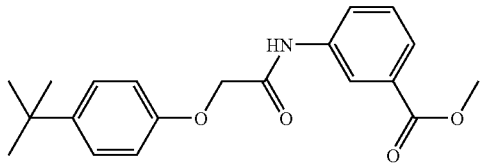 [SMILES: COC(=O)c1cccc(NC(=O)COc2ccc(C(C)(C)C)cc2)c1]

The present example was performed in the same manner to give 3-[2-(4-tert-butyl-phenoxy)acetylamino]-benzoic acid methyl ester as a light yellow solid (185 mg, 100% yield).

$^1$HNMR (CDCl$_3$, 300 Hz) 8.40 (1H, s, NH), 7.99-8.08 (2H, m, aromatic-H), 7.82-7.84 (1H, m, aromatic-H), 7.45 (1H, ps-t, J=7.8 Hz, aromatic-H), 7.34-7.38 2H, m, aromatic-H), 6.91-6.96 (2H, m, aromatic-H), 4.61 (2H, s, CH$_2$), 3.93 (3H, s, CH$_3$), 1.32 (9H, s, CH$_3$).

EXAMPLE 9

3-[2-(4-Fluoro-phenoxy)-acetylamino]-benzoic acid methyl ester

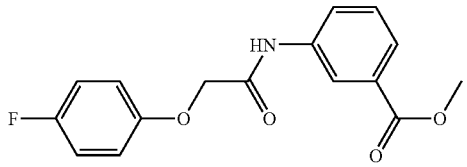

To 4-Fluoro-acetic acid (150.1 mg, 0.88 mmol), the amine 5 (199.6 mg, 1.32 mmol), EDCHCl (253.1 mg, 1.32 mmol) and HOBt (179.7 mg, 1.32 mmol) in DMF (8 mL) was added DIPEA (0.23 mL, 1.32 mmol). The mixture was stirred overnight, and then partitioned between Ethyl acetate and 10% HCl. The organic phase was washed with brine, dried (anhydrous MgSO$_4$), and concentrated. The residue was purified by silica gel flash column chromatography (n-Hexane:Ethyl acetate:MeOH=6:3:1) to give 3-[2-(4-Fluoro-phenoxy) acetylamino]-benzoic acid methyl ester as a white solid (236.1 mg, 88.5% yield).

$^1$H-NMR (CDCl$_3$) 8.37 (1H, s, NH), 8.07 (1H, nm, aromatic-H), 7.99 8.02 (1H, m, aromatic-H), 7.83 (1H, d, J=7.8 Hz, aromatic-H), 7.44 (1H, ps-t, J=7.8, aromatic-H), 7.02 7.08 (2H, m, aromatic-H), 6.93 6.97 (2H, m, aromatic-H), 4.59 (2H, s, CH$_2$), 3.92 (3H, s, CH$_3$).

EXAMPLE 10

3-[2-(4-Chloro-phenoxy)-acetylamino]-benzoic acid methyl ester

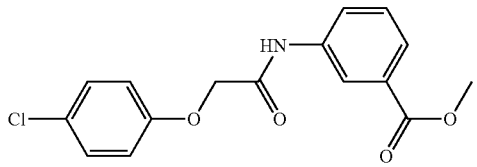

The present example was performed in the same manner to give 3-[2-(4-Chloro-phenoxy)-acetylamino]-benzoic acid methyl ester as a white solid (135.2 mg, 84.5% yield).

¹H-NMR (CDCl₃) 8.321H, s, NH), 8.06 (1H, s, aromatic-H), 8.00 (1H, d, J=8.4 Hz, aromatic-H), 7.83 (1H, d, J=8.2 Hz, aromatic-H), 7.45 (1H, ps-t, J=7.8 Hz, aromatic-H), 7.29-7.34 (2H, m, aromatic-H), 6.91-6.97 (2H, m, aromatic-H), 4.60 (2H, s, CH₂), 3.92 (3H, s, CH₃).

EXAMPLE 11

3-[2-(2,4-dichloro-phenoxy)-acetylamino]-benzoic acid methyl ester

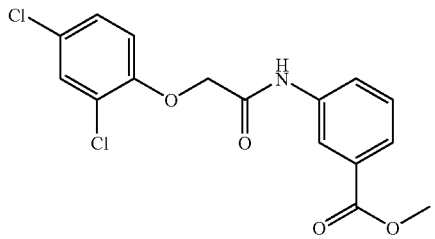 [SMILES: COC(=O)c1cccc(NC(=O)COc2ccc(Cl)cc2Cl)c1]

To (2,4-dichloro-phenoxy)-acetic acid (442.0 mg, 2.0 mmol), the amine (604.6 mg, 2.0 mmol), and benzotriazole-1-yl-oxy-tris-pyrrolidino-phosphonium hexafluorophosphate (PyBop) (2.05 g, 2.0 mmol) in DMF (1.5 mL) was added DIPEA (0.35 mL, 2.0 mmol). The mixture was stirred overnight and then partitioned between ethyl acetate and 10% HCl. The organic phase was washed with brine, dried (MgSO₄ anh), and concentrated. The residue was purified by silica gel flash column chromatography (n-Hexane:Ethyl acetate:MeOH=6:3:1) to give 3-[2-(2,4-dichloro-phenoxy)-acetylamino]-benzoic acid methyl ester as a white solid (701.2 mg, 99.0% yield).

¹H-NMR (CDCl₃) 8.63 (1H, s, NH), 8.14 (1H, m, aromatic-H), 7.93-7.96 (1H, m, aromatic-H), 7.84-7.86 (1H, m, aromatic-H), 7.43-7.48 (2H, m, aromatic-H), 7.25-7.29 (1H, m, aromatic-H), 6.91 (1H, d, J=9.0 Hz, aromatic-H), 4.66 (2H, s, CH₂), 3.93 (3H, s, CH₃).

EXAMPLE 12

2-[2-(2,4-Chloro-phenoxy)-acetylamino]-benzoic acid methyl ester

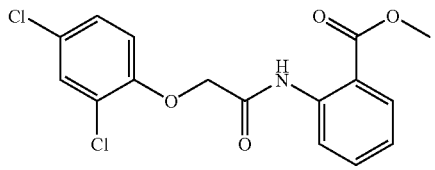 [SMILES: COC(=O)c1ccccc1NC(=O)COc1ccc(Cl)cc1Cl]

To (2,4-dichloro-phenoxy)-acetic acid (110.6 mg, 0.5 mmol), 2-aminobenzoic acid methyl ester (151.2 mg, 1.0 mmol), and benzotriazole-1-yl-oxy-tris-pyrrolidino-phosphonium hexafluorophosphate (pybop) (520.3 g, 1.0 mmol) in DMF (5 mL) was added N,N-diisopropylethylamine, redistilled (DIPEA) (0.17 mL, 1.0 mmol). The mixture was stirred overnight and then partitioned between ethyl acetate and 10% HCl. The organic phase was washed with brine, dried (MgSO₄ anh), and concentrated. The residue was purified by silica gel flash column chromatography (n-Hexane: Ethyl acetate:MeOH=6:3:1) to give 2-[2-(2,4-dichloro-phenoxy)-acetylamino]-benzoic acid methyl ester as a white solid (118.0 mg, 66.6% yield).

¹H-NMR (CDCl₃, 300 Hz) 11.84 (1H, s, NH), 8.73 (1H, d, J=8.1 Hz, aromatic-H), 8.05 (1H, dd, J=8.1 & 1.8 Hz, aromatic-H), 7.57 (1H, m, aromatic-H), 7.44 (1H, d, J=2.4 Hz, aromatic-H), 7.13 7.22 (2H, m, aromatic-H), 6.92 (1H, d, J=8.4 Hz, aromatic-H), 4.69 (2H, s, CH₂), 3.90 (3H, s, CH₃).

EXAMPLE 13

4-[2-(2,4-dichloro-phenoxy)-acetylamino]-benzoic acid methyl ester

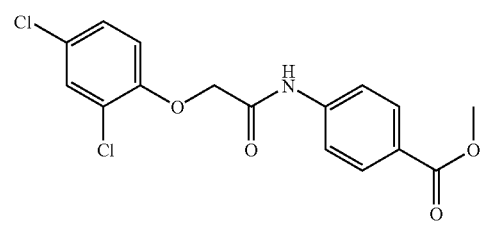 [SMILES: COC(=O)c1ccc(NC(=O)COc2ccc(Cl)cc2Cl)cc1]

The mixture of (2,4-dichloro-phenoxy)-acetic acid (110.5 mg, 0.5 mmol), 4-aminobenzoic acid methyl ester (151.2 mg, 1.0 mmol), 4-dimethylaminopyridine (122.7 mg, 1.0 mmol) and benzotriazole-1-yl-oxy-tris-pyrrolidino-phosphonium hexafluorophosphate (pybop) (520.3 mg, 1.0 mmol) in DMF (8.0 mL) was stirred overnight and then partitioned between ethyl acetate and 10% HCl. The organic phase was washed with brine, dried (MgSO₄ anh), and concentrated. The residue was purified by silica gel flash column chromatography (n-Hexane:Ethyl acetate:MeOH=6:3:1) to give 4-[2-(2,4-dichloro-phenoxy)-acetylamino]-benzoic acid methyl ester as a white solid (169.6 mg, 95.8% yield).

¹H-NMR (CD₃OD) 7.96 7.99 (2H, m, aromatic-H), 7.64 7.71 (2H, m, aromatic-H), 7.41 (1H, d, J=2.4 Hz, aromatic-H), 7.21 7.25 (1H, m, aromatic-H), 7.01 (1H, d, J=8.4 Hz, aromatic-H), 4.71 (2H, s, CH₂), 3.87 (3H, s, CH₃).

EXAMPLE 14

3-[2-(2,4,5-trichloro-phenoxy)-acetylamino]-benzoic acid methyl ester

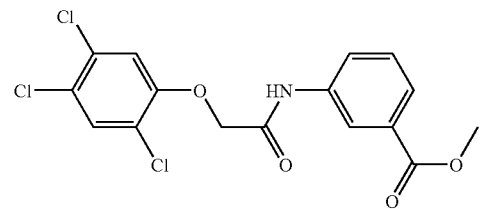 [SMILES: COC(=O)c1cccc(NC(=O)COc2cc(Cl)c(Cl)cc2Cl)c1]

The mixture of (2,4,5-trichloro-phenoxyacetic acid (127.8 mg, 0.5 mmol), 3-aminobenzoic acid methyl ester (151.2 mg, 1.0 mmol), 4-dimethylaminopyridine (122.2 mg, 1.0 mmol) and benzotriazole-1-yl-oxy-tris-pyrrolidino-phosphonium hexafluorophosphate (pybop) (520.3 g, 1.0 mmol) in DMF (5.0 mL) was stirred overnight and then partitioned between ethyl acetate and 10% HCl. The organic phase was washed with brine, dried (MgSO₄ anh), and concentrated. The residue was purified by silica gel flash column chromatography (n-Hexane:Ethyl acetate:MeOH=6:3:1) to give 3-[2-(2,4,5-trichloro-phenoxy)-acetylamino]-benzoic acid methyl ester as a white solid (166.4 mg, 85.6% yield).

¹H-NMR (CDCl₃) 8.55 (1H, s, NH), 8.13 (1H, s, aromatic-H), 7.95 (1H, d, J=7.8 Hz, aromatic-H), 7.85 (1H, d, J=7.2 Hz, aromatic-H), 7.56 (1H, s, aromatic-H), 7.46 (1H, ps-t, J=7.8 Hz, aromatic-H), 7.08 (1H, s, aromatic-H), 4.65 (2H, s, CH$_2$), 3.93 (3H, s, CH$_3$).

EXAMPLE 15

3-[2-(4-bromo-phenoxy)-acetylamino]-benzoic acid methyl ester

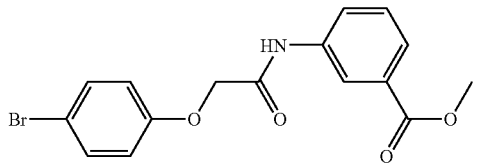 [SMILES: COC(=O)c1cccc(NC(=O)COc2ccc(Br)cc2)c1]

To a solution of the 4-bromophenoxy acetic acid (139 mg, 0.6 mmol) and amine (76 mg, 0.5 mmol) in DMF (5.0 mL) were added EDCHCl (144 mg, 0.75 mmol), HOBT (101 mg, 0.75 mmol), and DIPEA (0.13 mL, 0.75 mmol). The reaction mixture was stirred at room temperature overnight and then partitioned between Ethyl acetate and brine. The organic phase was dried (anhydrous MgSO$_4$), and concentrated. Purification by silica gel column chromatography (n-Hexane:Ethyl acetate:MeOH=12:3:1) gave 3-[2-(4-bromo-phenoxy)-acetylamino]-benzoic acid methyl ester as a white solid (138 mg, 76% yield).

$^1$H-NMR (CDCl$_3$, 300 Hz) 8.32 (1H, s, NH), 8.06 (1H, m, aromatic), 7.99 (1H, m, aromatic), 7.84 (1H, m, aromatic), 7.42-7.47 (3H, m, aromatic), 6.89 (2H, m, aromatic), 4.59 (2H, s, OCH$_2$CO), 3.92 (3H, s, OCH$_3$).

EXAMPLE 16

3-[2-(4-iodo-phenoxy)-acetylamino]-benzoic acid methyl ester

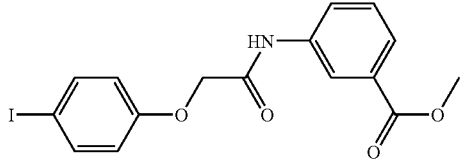 [SMILES: COC(=O)c1cccc(NC(=O)COc2ccc(I)cc2)c1]

The present example was performed in the same manner to give 3-[2-(4-iodo-phenoxy)-acetylamino]-benzoic acid methyl ester as a white solid (199.0 mg, 97.0% yield).

$^1$H-NMR (CDCl$_3$) 8.31 (1H, s, NH), 8.06 (1H, s, aromatic-H), 8.00 (1H, d, J=8.1 Hz, aromatic-H), 7.83 (1H, d, J=7.8 Hz, aromatic-H), 7.61-7.66 (2H, m, aromatic-H), 7.44 (1H, ps-t, J=7.8 Hz, aromatic-H), 6.76-6.81 (2H, m, aromatic-H), 4.59 (2H, s, CH$_2$), 3.92 (3H, s, CH$_3$).

EXAMPLE 17

3-[2-(4-acetyl-phenoxy-acetylamino]-benzoic acid methyl ester

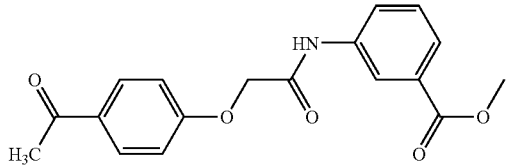 [SMILES: COC(=O)c1cccc(NC(=O)COc2ccc(C(C)=O)cc2)c1]

To a solution of the 4-acetylphenoxy acetic acid (97 mg, 0.5 mmol) and 3-amino benzoic acid methyl ester (113 mg, 0.75 mmol) in DMF (5.0 mL) were added EDCHCl (144 mg, 0.75 mmol), HOBT (101 mg, 0.75 mmol), and DIPEA (0.13 mL, 0.75 mmol). The reaction mixture was stirred at room temperature overnight, and then partitioned between Ethyl acetate and brine. The organic phase was dried (anhydrous MgSO$_4$), and concentrated. Purification by silica gel column chromatography (n-Hexane:Ethyl acetate:MeOH=6:3:1) gave 3-[2-(4-acetyl-phenoxy)acetylamino]-benzoic acid methyl ester as a white solid (158 mg, 97% yield).

$^1$H-NMR (CDCl$_3$, 300 Hz) 8.32 (1H, s, NH), 8.07 (1H, m, aromatic), 7.97-8.01 (3H, m, aromatic), 7.83 (1H, d, J=7.8 Hz, aromatic), 7.45 (1H, ps, t, J=7.8 Hz, aromatic), 7.05 (2H, m, aromatic), 4.69 (2H, s, OCH$_2$CO), 3.92 (3H, s, OCH$_3$), 2.58 (3H, s, COCH$_3$).

EXAMPLE 18

3-[2-(4-Adamantan-1-yl-phenoxy)acetyl-amino]-4-hydroxy benzoic acid methyl ester

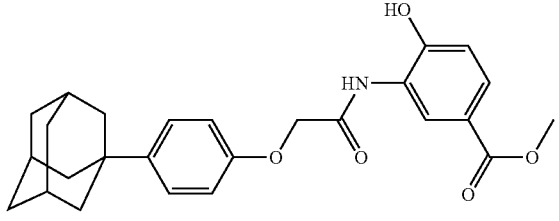 [SMILES: COC(=O)c1ccc(O)c(NC(=O)COc2ccc(C34CC5CC(CC(C5)C3)C4)cc2)c1]

(4-Adamantan-1-yl-phenoxy)-acetic acid (143.2 mg, 0.5-mmol) was dissolved in THF (5 mL), and oxalyl chloride (178.5 mg, 0.11 mL, 1.5 mmol) and one drop of DMF were added to the solution. After the mixture was stirred for 1 h at room temperature, 3-amino-4-hydroxy-benzoic acid methyl ester (125.4 mg, 0.75 mmol) and pyridine (0.05 mL) were added, and the resulting. Solution was stirred at room temperature overnight, and then partitioned between ethyl acetate and 10% HCl. The organic phase was washed with brine, dried (MgSO$_4$-anh), and concentrated. The residue was purified by (n-Hexane:Ethyl acetate:MeOH=6:3:1) to give 3-[2-(4-Adamantan-1-yl-phenoxy)-acetylamino]-4-hydroxy-benzoic acid methyl ester as a white solid (183.2 mg, 84.1% yield).

$^1$H-NMR (DMSO-d$_6$, 300 Hz) 11.10 (1H, s, OH), 9.24 (1H, s, NH), 8.69 (1H, m, aromatic-H), 7.60-7.64 (1H, m, aromatic-H), 7.30 (2H, d, J=8.4 Hz, aromatic-H), 6.94-6.99 (3H, m, aromatic-H), 4.74 (2H, s, CH$_2$), 3.79 (3H, s, CH$_3$), 2.04 (3H, m, adamantly-H), 1.83 (6H, m, adamantly-H), 1.72 (6H, m, adamantly-H).

EXAMPLE 19

3-[2-(4-tert-butyl-phenoxy)-acetyl-amino]-4-hydroxy-benzoic acid methyl ester

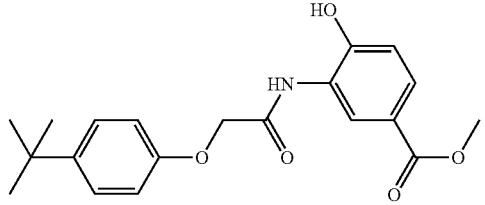 [SMILES: COC(=O)c1ccc(O)c(NC(=O)COc2ccc(C(C)(C)C)cc2)c1]

(4-tert-butyl-phenoxy)-acetic acid (200 mg, 0.96 mmol) and 3-amino-4-hydroxy-benzoic acid methyl ester (240.7 mg, 1.44 mmol) were dissolved in PPSE (3 mL), and reacted for 2.5 h at 140° C. After saturated sodium bicarbonate aqueous solution was added, organic phase was washed with 10% HCl and brine. The organic phase was dried (MgSO4 anh), and concentrated. The residue was purified by silica gel column chromatography (n-Hexane:Ethyl acetate:MeOH=15:3:1) to give 3-[2-(4-tert-butyl-phenoxy)-acetyl-amino]-4-hydroxy-benzoic acid methyl ester as an orange solid (350 mg, 89% yield).

$^1$H-NMR (CD$_3$OD, 300 Hz) 8.79 (1H, d, J=2.4 Hz aromatic), 7.68 (1H, dd, J=8.7&1.8 Hz, aromatic), 7.35 (2H, m, aromatic), 6.89-6.99 (3H, m, aromatic), 4.66 (2H, s, OCH$_2$), 3.85 (3H, s, CH$_3$), 1.29 (9H, s, (CH$_3$)$_3$)

EXAMPLE 20

3-(2-biphenylyl-acetyl-amino)benzoic acid methyl ester

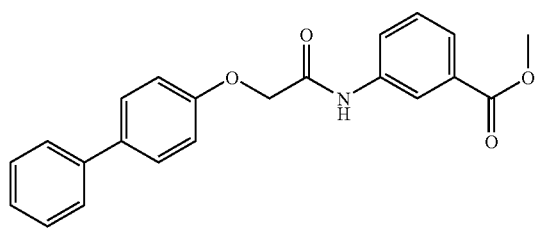 [SMILES: COC(=O)c1cccc(NC(=O)COc2ccc(-c3ccccc3)cc2)c1]

To a solution of the 4-biphenyl acetic acid (106.1 mg, 0.50 mmol), 3-amino benzoic acid methyl ester (113.4 mg, 0.75 mmol), EDCHCl (143.8 mg, 0.75 mmol) and HOBT (101.4 mg, 0.75 mmol) were dissolved in DMF (5.0 mL), and DIPEA (0.13 mL, 0.75 mmol) were added. The reaction mixture was stirred at room temperature overnight and then partitioned between Ethyl acetate and brine. The organic phase was dried (anhydrous MgSO$_4$), and concentrated. Purification by silica gel column chromatography (n-Hexane:Ethyl acetate:MeOH=6:3:1) gave 3-(2-biphenyl-4-yl-acetyl-amino)benzoic acid methyl ester as a white solid (174 mg, 100% yield).

$^1$H-NMR (CDCl$_3$, 300 Hz) 7.88-7.91 (2H, m, aromatic-H), 7.77 (1H, d, J=7.8 Hz, aromatic-H), 7.61-7.66 (4H, m, aromatic-H), 7.36-7.49 (6H, m, aromatic-H), 7.18 (1H, s, NH), 3.90 (3H, s, CH$_3$), 3.81 (2H, s, CH$_2$).

EXAMPLE 21

4[2-(4-Adamantan-1-yl-phenoxy)acetyl-amino]-isophthalic acid dimethyl ester

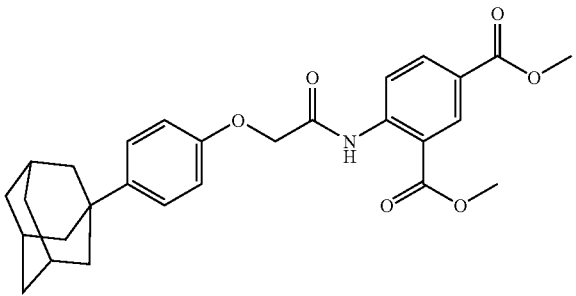 [SMILES: COC(=O)c1ccc(NC(=O)COc2ccc(C34CC5CC(CC(C5)C3)C4)cc2)c(C(=O)OC)c1]

To a mixture of (4-adamantan-1-yl-phenoxy)-acetic acid (229 mg, 0.8 mmol) and 4-aminoisophthalic acid dimethyl ester (301 mg, 1.4 mmol) were dissolved in DMF (5 mL), and EDCHCl (140 mg, 0.75 mmol), HOAt (163 mg, 1.2 mmol) and DIPEA (0.21 ml, 1.2 mmol) was added. The mixture was stirred overnight, and then partitioned between ethyl acetate and brine. The organic phase was dried (MgSO$_4$ anh), and concentrated. The residue was purified by silica gel column chromatography (CH$_2$Cl$_2$:MeOH=50:1) to give 4-[2-(4-Adamantan-1-yl-phenoxy)acetyl-amino]-isophthalic acid dimethyl ester as a white solid (281 mg, 76.3% yield).

$^1$H-NMR (CDCl$_3$, 300 Hz) 12.00 (1H, s, NH), 9.40 (1H, d, J=1.8 Hz, aromatic), 8.12 (1H, d, J=7.8 Hz, aromatic), 7.78 (1H, dd, J=8.1 & 1.8 Hz, aromatic), 7.33 (2H, m, aromatic), 7.03 (2H, m, aromatic), 4.65 (2H, s, OCH$_2$CO), 3.97 (3H, s, OCH$_3$), 3.95 (3H, s, OCH$_3$), 2.09 (3H, m, adamantyl), 1.89-1.90 (6H, m, adamantyl), 1.72-1.82 (6H, m, adamantyl).

Example 22

3-[2-(4-nitro-phenoxy)acetyl-amino]-benzoic acid methyl ester

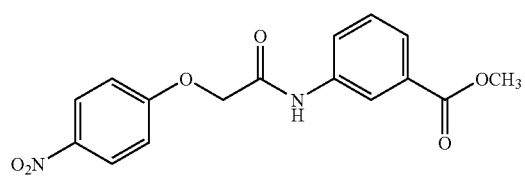 [SMILES: COC(=O)c1cccc(NC(=O)COc2ccc([N+](=O)[O-])cc2)c1]

To a solution of the 4-nitrophenoxy acetic acid (100 mg, 0.5 mmol), 3-amino benzoic acid methyl ester (115 mg, 0.76 mmol), HOBt (102.81 mg, 0.76 mmol) and DIPEA (98.34 mg, 0.76 mmol) in DMF (4.0 mL) were added EDC (145.86 mg, 0.76 mmol) at room temperature. After reaction terminated, the reaction mixture in cool water was diluted with Ethyl acetate. The organic phase was washed with aqueous sodium bicarbonate and dried (anhydrous MgSO$_4$), and concentrated. Purification by silica gel column chromatography (Ethyl acetate:Hexane=1:9~1:1) gave 3-[2-(4-nitro-phenoxy)acetyl-amino]-benzoic acid methyl ester as a white solid (150 mg, 89% yield).

$^1$H NMR (DMSO-d$_6$, 300 MHz) 8.35 (1H, s, CONH), 8.24 (2H, m, aromatic), 8.08 (1H, t, J=1.8 Hz, aromatic), 7.97 (1H, d, J=8.1 Hz, aromatic), 7.82 (1H, d, J=7.8 Hz, aromatic), 7.43 (1H, t, J=7.8 Hz, aromatic), 7.09 (2H, m, CONH$_2$), 4.72 (2H, s, OCH$_2$), 3.90 (3H, s, OCH$_3$).

EXAMPLE 23

3-[2-(4-Adamantan-1-yl-phenoxy)acetyl-amino]-benzamide

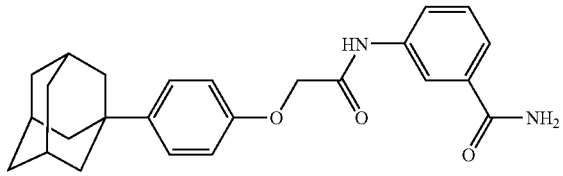

To a solution of the 4-adamantan-1-yl-phenoxy acetic acid (114.6 mg, 0.40 mmol) and 3-amino benzamide (81.7 mg, 0.60 mmol) ware dissolved in DMF (4.0 mL), and were added EDCHCl (115.1 mg, 0.60 mmol), HOBt (81.1 mg, 0.60 mmol) and DIPEA (0.15 mL, 0.60 mmol). The reaction mixture was stirred overnight and then partitioned between Ethyl acetate and brine. The organic phase was dried (MgSO$_4$ anh), and concentrated. The residue was purified by silica gel column chromatography (n-Hexane:Ethyl acetate:MeOH=9:3:

1) gave 3-[2-(4-Adamantan-1-yl-phenoxy)acetyl-amino]-benzamide as a white solid (145.0 mg, 89.6% yield).

$^1$H-NMR (CD$_3$OH) 8.08 (1H, m, aromatic-H), 7.80-7.80 (1H, m, aromatic-H), 8.57 (1H, d, J=8.4 Hz aromatic-H), 7.43 (1H, m, aromatic-H), 7.30-7.33 (2H, m, aromatic-H), 7.00 (2H, m, aromatic-H), 4.65 (2H, s, CH$_2$), 2.06 (3H, m, adamantyl-H), 1.90 (6H, m, adamantly-H), 1.80 (6H, m, adamantly-H).

EXAMPLE 24

3-[2-(2,4-dichloro-phenoxy)acetyl-amino]-benzamide

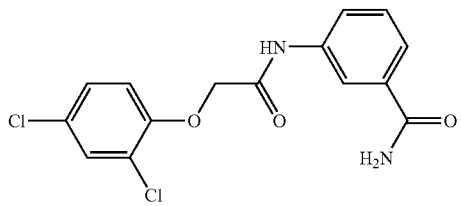

To a solution of the 4-biphenyl acetic acid (106.1 mg, 0.50 mmol), 3-amino benzoic acid methyl ester (113.4 mg, 0.75 mmol), EDCHCl (143.8 mg, 0.75 mmol) and HOBT (101.4 mg, 0.75 mmol) were dissolved in DMF (5.0 mL), and DIPEA (0.13 mL, 0.75 mmol) were added. The reaction mixture was stirred at room temperature overnight and then partitioned between Ethyl acetate and brine. The organic phase was dried (anhydrous MgSO$_4$), and concentrated. Purification by silica gel column chromatography (n-Hexane:Ethyl acetate:MeOH=6:3:1) gave 3-(2-biphenyl-4-yl-acetyl-amino)benzoic acid methyl ester as a white solid (174 mg, 100% yield).

EXAMPLE 25

3-[2-(2,4,5-trichloro-phenoxy)acetyl-amino]-benzamide

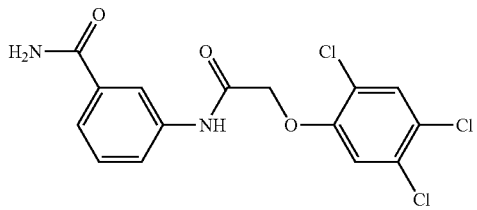 [SMILES: NC(=O)c1cccc(NC(=O)COc2cc(Cl)c(Cl)cc2Cl)c1]

To a solution of the 2,4,5-trichloro-phenoxy acetic acid (76.7 mg, 0.3 mmol), 3-amino benzamide (61.3 mg, 0.45 mmol), EDC (86.3 mg, 0.45 mmol) and HOBt (61.3 mg, 0.45 mmol) were dissolved in DMF (3 mL), and DIPEA (0.08 mL, 0.45 mmol) were added. The reaction mixture was stirred at room temperature overnight, and then partitioned between Ethyl acetate and brine. The organic phase was dried (anhydrous MgSO$_4$), and concentrated. Purification by silica gel column chromatography (CH$_2$Cl$_2$:MeOH=6:3:1) gave 3-[2-(2,4,5-trichloro-phenoxy)acetyl-amino]-benzamide as a white solid (95.2 mg, 84.9% yield).

$^1$H-NMR (CDCl$_3$) 10.31 (1H, s, NH), 8.06 (1H, s, aromatic-H), 7.95 (1H, s, NH$_2$), 7.85 (1H, s, aromatic-M, 7.75 (1H, d, J=7.8 Hz, aromatic-H), 7.58 (1H, d, J=7.8 Hz, aromatic-H), 7.47 (1H, s, aromatic-H), 7.36-7.42 (2H, m, aromatic-H, NH$_2$), 4.95 (2H, s, CH$_2$).

EXAMPLE 26

3-[2-(4-bromo-phenoxy)acetyl-amino]-benzamide

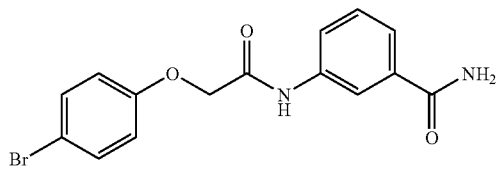 [SMILES: NC(=O)c1cccc(NC(=O)COc2ccc(Br)cc2)c1]

To a mixture of (4-bromo-phenoxyacetic acid (392.5 mg, 1.8 mmol), 3-amino-benzamide (408.2 mg, 3.0 mmol), N-(3-ethylaminopropyl)-N'-ethyl carbodiimide HCl (EDC) (517.6 mg, 2.7 mmol) and 1-hydroxybenzotriazole (HOBt) (365.3 mg, 2.7 mmol) in DMF (18 mL) was added N,N-diisopropylethylamine, redistilled (DIPEA) (0.47 ml, 2.7 mmol). The mixture was stirred overnight and then partitioned between ethyl acetate and water. The organic phase was washed with brine, dried (MgSO$_4$ anh), and concentrated. The residue was purified by recrystallization from the mixture of Ethyl acetate and MeOH to give 3-[2-(4-bromo-phenoxy)acetyl-amino]-benzamide as a white solid (134.9 mg, 21.52% yield).

$^1$HNMR (DMSO-d$_6$) 10.21 (1H, s, NH), 8.09 (1H, s, aromatic-H), 7.94 (1H, s, NH$_2$), 7.79 (1H, d, J=8.1 Hz, aromatic-H), 7.35-7.59 (5H, m, aromatic-H, NH$_2$), 6.99 (2H, d, J=9.3 Hz aromatic-H), 4.72 (2H, s, CH$_2$).

EXAMPLE 27

3-[2-(4-bromo-2-chloro-phenoxy)acetyl-amino]-benzamide

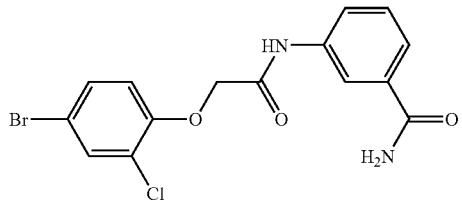 [SMILES: NC(=O)c1cccc(NC(=O)COc2ccc(Br)cc2Cl)c1]

A mixture of 4-bromo-2-chloro-phenol (2.0 g, 9.64 mmol) and anhydrous potassium carbonate (4.0 g, 28.92 mmol) in dry DMF (30 ml) was heated at 60° C. for 1 h under Ar atmosphere. The mixture was then cooled to room temperature and ethyl chloroacetate (1.24 ml, 11.57 mmol) was added through septum using syringe. The mixture was stirred overnight at room temperature and poured into water with stirring. Stirring continued for 10 min, and then partitioned between ethyl acetate and water. The organic phase washed with brine, dried (anhydrous MgSO$_4$), and concentrated. The residue was purified by silica gel column chromatography (n-Hexane:Ethyl acetate:MeOH=15:3:1) to give (4-Bromo-2-chloro-phenoxy)-acetic acid ethyl ester as a colorless oil (2.98 (2.83) g, >100% yield). To (4-bromo-2-chloro-phenoxy)-acetic acid (132.8 mg, 0.5 mmol), 3-amino-benzamide (102.2 mg, 0.75 mmol), N-(3-dimethylaminopropyl)-N'-ethyl carbodiimide HCl (EDC) (143.8 mg, 0.75 mmol) and 1-hydroxybenzotriazole (HOBt) (101.4 mg, 0.75 mmol) in DMF (5 ml) was added N,N-diisopropylethylamine, redistilled (DIPEA) (0.13 ml, 0.75 mmol). The mixture was stirred overnight, and then partitioned between ethyl acetate and water. The organic phase was washed with brine, dried (MgSO₄ anh), and concentrated. The residue was purified by silica gel flash column chromatography (CH₂CH₂:MeOH=10:1) to give 3-[2-(4-bromo-2-chloro-phenoxy)acetyl-amino]-benzamide as a white solid (181.4 mg, 94.6% yield).

¹H-NMR (DMSO-d₆) 10.30 (1H, s, NH), 8.06 (1H, s, aromatic-H), 7.94 (1H, s, NH₂), 7.70 7.77 (2H, m, aromatic-H), 7.57 (1H, d, J=7.2 Hz, aromatic-H), 7.48 (1H, dd, J=16.2 & 2.4 Hz, aromatic-H), 7.35 7.42 (2H, m, aromatic-H, NH₂), 7.06 (1H, d, J=9 Hz, aromatic-H), 4.87 (2H, s, CH₂).

EXAMPLE 28

3-[2-(4-iodo-phenoxy)acetyl-amino]-benzamide

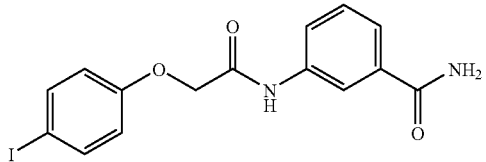 [SMILES: NC(=O)c1cccc(NC(=O)COc2ccc(I)cc2)c1]

To (4-iodo-phenoxy)acetic acid (83.5 mg, 0.3 mmol), 3-amino-benzamide (61.3 mg, 0.45 mmol), N-(3-dimethylaminopropyl)-N'-ethyl carbodiimide HCl (EDC) (86.3 mg, 0.45 mmol) and 1-hydroxybenzotriazole (HOBt) (61.3 mg, 0.45 mmol) in DMF (3 ml) was added N,N-diisopropylethylamine, redistilled (DIPEA) (0.08 ml, 0.45 mmol). The mire was stirred overnight, and then partitioned between ethyl acetate and water. The organic phase was washed with brine, dried (MgSO₄ anh), and concentrated. The residue was purified by silica gel flash column chromatography (CH₂CH₂:MeOH=6:1) to give 3-[2-(4-iodo-phenoxy)acetyl-amino]-benzamide as a white solid (105.1 mg, 88.4% yield).

¹H-NMR (DMSO-d₆) 10.22 (1H, s, NH), 8.09 (1H, s, aromatic-H), 7.94 (1H, s, NH₂), 7.79 (1H, d, J=8.1 Hz, aromatic-H), 7.56-7.64 (3H, m, aromatic-H), 7.35-7.41 (2H, m, aromatic-H, NH₂), 6.86 (2H, d, J=, 8.7 Hz, aromatic-H), 4.71 (2H, s, CH₂).

EXAMPLE 29

3-(2-phenoxy-acetyl-aminobenzamide

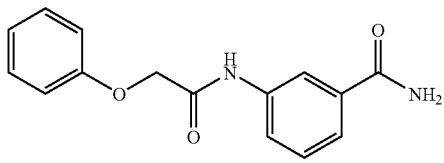 [SMILES: NC(=O)c1cccc(NC(=O)COc2ccccc2)c1]

To a solution of phenoxy-acetic acid (100 mg, 0.65 mmol), 3-amino benzamide (178.9 mg, 1.31 mmol), HOBt (177.7 mg, 1.31 mmol) and DIPEA (170 mg, 1.31 mmol) in DMF (6 ml) was added EDC (252 mg, 1.31 mmol) at room temperature and the resulting mixture was stirred until reaction completion as indicated by TLC. Reaction mixture was poured onto ice cold water, diluted with a mixture of MeOH:MC (10%), separated organic layer and sequentially washed with aqueous sodium bicarbonate, brine and water, and dried over anhydrous MgSO₄. The solvent was filtered and evaporated under reduced pressure to afford a crude solid, which was purified flash chromatography on silica gel (MeOH:MC=1:9~2:8) to afford of 3-(2-phenoxy-acetyl-amino)-benzamide as a colorless solid (146 mg, 82% yield).

¹H NMR (DMSO-d₆, 300 MHz) 10.19 (1H, s, CONH), 8.09 (1H, s, aromatic), 7.93 (1H, s, aromatic), 7.80 (1H, d, J=9.0 Hz, aromatic), 7.56 (1H, d, J=7.5 Hz, aromatic), 7.35 (4H, m, CONH₂, aromatic), 6.98 (3H, m, aromatic), 4.70 (2H, s, OCH₂).

EXAMPLE 30

3-[2-(4-tert-butyl-phenoxy)-acetyl-amino]-benzamide

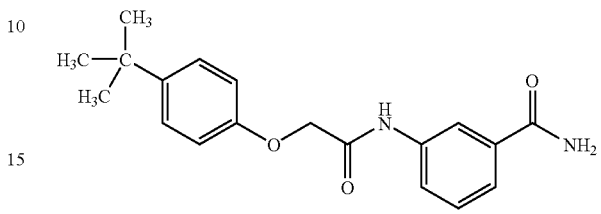

To a solution of (4-tert-butyl-phenoxy)acetic acid (125 mg, 0.6 mmol), 3-amino benzamide (163.5 mg, 1.2 mmol), HOBT (162 mg, 1.2 mmol) and DIPEA (155 mg, 1.2 mmol) in DMF (6 ml) was added EDC (230.05 mg, 1.2 mmol) at room temperature and the resulting mixture was stirred until reaction completion as indicated by TLC. Reaction mixture was poured onto ice cold water, diluted with a mix of MeOH:MC (10%), separated organic layer and sequentially washed with aqueous sodium bicarbonate, brine and water, and dried over anhydrous MgSO₄. The solvent was filtered and evaporated under reduced pressure to afford a crude solid, which was purified flash chromatography on silica gel (MeOH:MC=1:9~2:8) to afford of 3-[2-(4-tert-butyl-phenoxy)-acetylamino]-benzamide as a colorless solid (168 mg, 85.75% yield).

¹HNMR (DMSO-d₆, 300 MHz) 10.67 (1H, s, CONH), 8.44 (1H, d, J=5.1 Hz, CONH₂), 8.41 (1H, s, CONH₂), 8.20 (1H, brs, pyridine), 7.68 (1H, brs, pyridine), 7.49 (1H, d, J=1.5, 5.1 Hz, pyridine), 7.16-7.11 (2H, m, aromatic), 7.01-6.97 (2H, m, aromatic), 4.80 (2H, s, OCH₂).

EXAMPLE 31

3-(2-p-tolyloxy-acetyl-amino)-benzamide

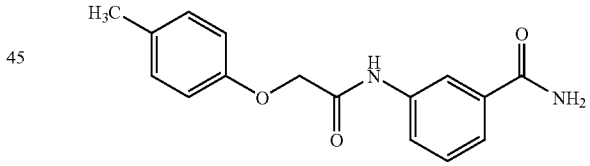

To a solution of (4-methyl-phenoxyacetic acid (100 mg, 0.6 mmol), 3-amino benzamide (163.86 mg, 1.2 mmol), HOBT (162 mg, 1.2 mmol) and DIPEA (155 mg, 1.2 mmol) in DMF (6 ml) was added EDC (230.8 mg, 1.2 mmol) at room temperature and the resulting mixture was stirred until reaction completion as indicated by TLC. Reaction mixture was poured onto ice cold water, diluted with a mixture of MeOH:MC (10%), separated organic layer and sequentially washed with aqueous sodium bicarbonate, brine and water, and dried over anhydrous MgSO₄. The solvent was filtered and evaporated under reduced pressure to afford a crude solid, which was purified flash chromatography on silica gel (MeOH:MC=1:9~2:8) to afford of 3-[2-(4-tert-butyl-phenoxy)-acetylamino]-benzamide as a colorless solid (133 mg, 78% yield).

¹H NMR (DMSO-d₆, 300 MHz) 10.16 (1H, s, CONH), 8.09 (1H, s, aromatic), 7.93 (1H, s, aromatic), 7.80 (1H, d, J=8.1 Hz, aromatic), 7.56 (1H, d, J=8.1 Hz, aromatic), 7.37

(2H, m, CONH₂), 7.10 (2H, d, J=8.7 Hz, aromatic), 6.90 (2H, d, J=8.4 Hr; aromatic), 4.65 (1H, s, OCH₂), 2.23 (3H, s, CH₃).

EXAMPLE 32

3-[2-(4-nitro-phenoxy)-acetyl-amino)benzamide

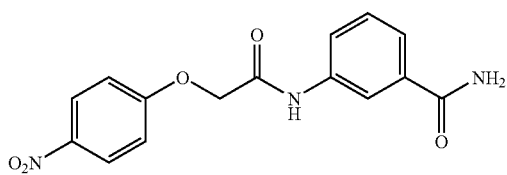 [SMILES: NC(=O)c1cccc(NC(=O)COc2ccc([N+](=O)[O-])cc2)c1]

To a solution of (4-nitrophenoxy)-acetic acid (100 mg, 0.5 mmol), 3-amino benzamide (103.5 mg, 0.76 mmol), HOBt (102.81 mg, 0.76 mmol) and DIPEA (98.34 mg, 0.76 mmol) in DMF (2 ml) was added EDC (145.86 mg, 0.76 mmol) at room temperature and the resulting mixture was stirred until reaction completion as indicated by TLC. Reaction mixture was poured onto ice cold water, diluted with a mixture of MeOH:MC (10%), separated organic layer and sequentially washed with aqueous sodium bicarbonate, brine and water, and dried over anhydrous MgSO₄. The solvent was filtered and evaporated under reduced pressure to afford a crude solid, which was purified flash chromatography on silica gel (MeOH:MC=1:9-2:8) to afford of 3-[2-(4-tert-butyl-phenoxy)acetylamino]-benzamide as a colorless solid (135 mg, 81% yield).

¹H NMR (DMSO-d₆, 300 MHz) 10.32 (1H, s, CONH), 8.24 (1H, d, J=9.3H aromatic), 8.08 (1H, s, aromatic), 7.94 (1H, s, aromatic), 7.78 (1H, d, J=8.1 Hz, aromatic), 7.58 (1H, d, J=7.2 Hz, aromatic), 7.39 (2H, m, CONH₂), 7.21 (2H, d, J=9.3 Hz, aromatic), 4.92 (2H, s, OCH₂).

EXAMPLE 33

2-(4-Adamantyl-1-yl-phenoxyl)-N-(3-sulfamoyl-phenyl)-acetamide

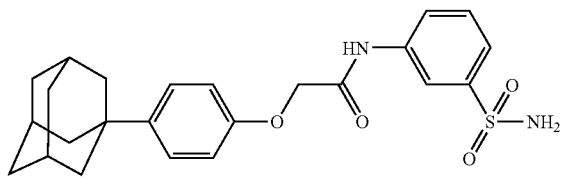 [SMILES: NS(=O)(=O)c1cccc(NC(=O)COc2ccc(C34CC5CC(CC(C5)C3)C4)cc2)c1]

The mixture of [4-(1-adamantyl)-phenoxy]acetic acid (80.7 mg, 0.28 mmol), 3-amino-benzenesulfonamide (72.3 mg, 0.42 mmol), N,N-diisopropylethylamine, redistilled (DIPEA) (0.1 ml, 0.56 mmol) and benzotriazole-1-yl-oxy-tris-pyrrolidino-phosphonium hexafluorophosphate (pybop) (291.4 mg, 0.56 mmol) in DMF (5 mL) was stirred overnight and then partitioned between ethyl acetate and water. The organic phase was washed with brine, dried (MgSO₄ anh), and concentrated. The residue was purified by Prep-TLC (n-Hexane:EtoAc:MeOH=6:3:1) to give 244-Adamantyl-1-yl-phenoxyl)-N-(3-sulfamoyl-phenyl)-acetamide as a white solid (23.1 mg, 18.7% yield).

¹H-NMR (DMSO-d₆, 300 Hz) 10.39 (1H, s, NH), 8.23 (1H, s, aromatic-H), 7.79 7.82 (1H, m, aromatic-H), 7.51 7.53 (2H, m, aromatic-H), 7.37 (2H, s, NH₂), 7.28 (2H, d, J=8.7 Hz, aromatic-H), 6.93 (2H, d, J=8.7 Hz aromatic-H), 2.04 (3H, m, adamantly-H), 1.83 (6H, m, adamantly-D), 1.72 (6H, m, adamantly-H).

EXAMPLE 34

2-(4-Adamantyl-1-yl-phenoxyl)-N-(4-sulfamoyl-phenyl)-acetamide

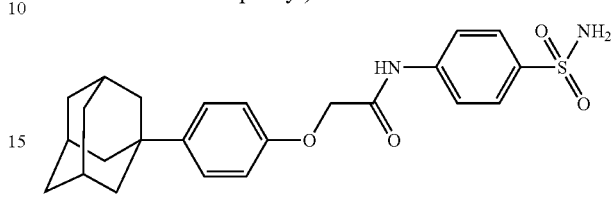

To a solution of the (4-adamantan-1-yl-phenoxy)-acetic acid (143 mg, 0.5 mmol) and 4-amino-benzenesulfonamide (103 mg, 0.6 mmol) in DMF (5.0 mL) were added benzotriazol-1-yl-N-oxy-tris(pyrrolidino)phosphonium hexafluorophosphate (PyBOP) (390 mg, 0.75 mmol), and 4-dimethylaminopyridine (DMAP) (92 mg, 0.75 mmol). The reaction mixture was stirred at room temperature overnight, and then partitioned between ethyl acetate and brine. The organic phase was dried (MgSO₄ anh), and concentrated. Purification by silica gel column chromatography (CH₂Cl₂:MeOH=40:1) gave 2-(4-Adamantan-1-yl-phenoxy)-N-(4-sulfamoyl-phenylacetamide as a white solid (78.9 mg, 35.8% yield).

¹H-NMR (DMSO-d₆, 300 Hz) 10.40 (1H, s, NH), 7.75-7.83 (4H, m, aromatic), 7.27-7.30 (4H, m, aromatic), 6.92 (2H, m, aromatic), 4.70 (2H, s, OCH₂CO), 2.04 (3H, m, adamantyl), 1.80-1.83 (6H, m, adamantyl), 1.67-1.75 (6H, m, adamantyl).

EXAMPLE 35

2-(4-Adamantyl-1-yl-phenoxyl)-N-(3-cyano-phenyl)-acetamide

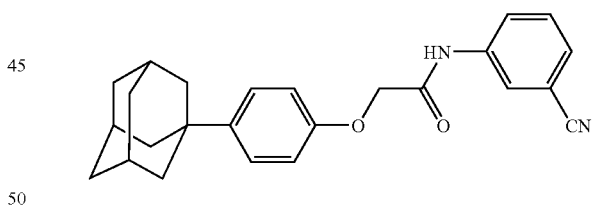

To 2-(4-Adamantan-1-yl-phenoxy)-acetic acid (200.0 mg, 0.70 mmol), 3-amino-benzonitrile (124.1 mg, 1.05 mmol), N-(3-dimethylaminopropyl)-N-ethyl carbodiimide HCl (EDC) (201.3 mg, 1.05 mmol) and 1-hydroxybenzotriazole (HOBt) (142.9 mg, 1.05 mmol) in DMF (10 mL) was added N,N-diisopropylethylamine, redistilled (DIPEA) (131.5 mg, 0.18 ml, 1.05 mmol). The mixture was stirred overnight; and then partitioned between ethyl acetate and 10% HCl. The organic phase was washed with brine, dried (MgSO₄ anh), and concentrated. The residue was purified by silica gel flash column chromatography (n-Hexane:EtoAc:MeOH=6:3:1) to give 2-(4-Adamantyl-1-yl-phenoxyl)-N-(3-cyano-phenylacetamide as a yellow solid (222.8 mg, 82.6% yield).

¹H-NMR (CDCl₃, 300 Hz) 8.41 (1H, s, NH), 8.03 (1H, s, aromatic-H), 7.78-7.81 (1H, m, aromatic-H), 7.42 7.49 (2H, m, aromatic-H), 7.32 7.37 (2H, m, aromatic-H), 6.91 6.97

(2H, m, aromatic-H), 4.62 (2H, s, CH$_2$), 2.09 (3H, m, adamantly-H), 1.89 (6H, m, adamantly-H), 1.77 (6H, m, adamantly-H).

EXAMPLE 36

N-(3-Cyano-phenyl)-2-2,4-dichloro-phenoxy)-acetamide

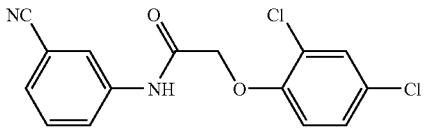

To (2,4-dichloro-phenoxy)-acetic acid (300.0 mg, 1.36 mmol), 3-amino-benzonitrile (241.0 mg, 2.04 mmol), N-(3-dimethylaminopropyl)-N'-ethyl carbodiimide HCl (EDC) (391.1 mg, 2.04 mmol) and 1-hydroxybenzotriazole (HOBt) (277.7 mg, 2.04 mmol) in DMF (18 mL) was added N,N-diisopropylethylamine, redistilled (DIPEA) (0.35 ml, 2.04 mmol). The mixture was stirred overnight, and then partitioned between ethyl acetate and 10% HCl. The organic phase was washed with brine, dried (MgSO$_4$ anh), and concentrated. The residue was purified by silica gel flash column chromatography (n-Hexane:EtoAc:MeOH=6:3:1) to give AC-147 as a white solid (353.7 mg, 81.3% yield).

$^1$H-NMR (DMSO-d$_6$, 300 Hz) 7.90 (1H, s, NH), 7.26 (1H, s, aromatic-H), 6.97-7.01 (1H, m, aromatic-H), 6.65-6.71 (3H, m, aromatic-H), 6.47-6.50 (1H, m, aromatic-H), 6.12 (1H, d, J=8.7 Hz, aromatic-H), 4.86 (2H, s, CH$_2$).

EXAMPLE 37

2-(4-Adamantan-1-yl-phenoxy)-N-(3-trifluoromethyl-phenyl)-acetamide

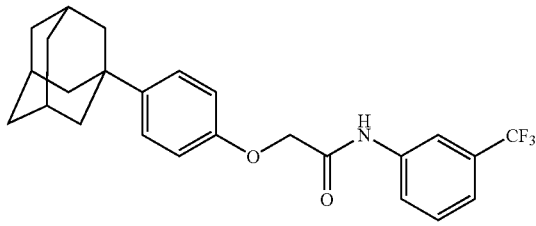 [SMILES: O=C(COc1ccc(C23CC4CC(CC(C4)C2)C3)cc1)Nc1cccc(C(F)(F)F)c1]

To a solution of (4-adamantan-1-yl-phenoxy)-acetic acid (50 mg, 0.17 mmol), 3-trifluoromethyl-phenylamine (42 mg, 0.26 mmol) and DIPEA (33.85 mg, 0.26 mmol) in DMF (2 mL) was added EDC (50.2 mg, 0.26 mmol) and HOBt (35.39 mg, 0.26 mmol) at room temperature. The reaction mix was stirred at room temperature until completion and then poured into water (100 mL). The resulting solid was extracted with ethyl acetate, washed with brine, aqueous sodium bicarbonate and water, dried over anhydrous MgSO$_4$, filtered and concentrated under reduced pressure. The resulting crude product was purified by flash chromatography on silica gel (EtOAc: hexanes=1:9 to 2:8) to afford of 2-(4-adamantan-1-yl-phenoxy)-N-(3-trifluoromethyl-phenyl)acetamide as a colorless solid (0.061 g, 81% yield).

$^1$H NMR (CDCl$_3$, 300 MHz) 8.44 (1H, s, CONH), 7.89 (1H, s, aromatic), 7.83 (1H, d, J=7.8 Hz, aromatic), 7.50-7.32 (4H, m, aromatic), 6.95 (2H, d, J=8.7 Hz, aromatic), 4.61 (2H, s, OCH$_2$), 2.10 (3H, brs, adamantyl), 1.90 (6H, d, J=2.4 Hz, adamantyl), 1.77 (6H, m, adamantyl).

EXAMPLE 38

2-(4-Adamantan-1-yl-phenoxy)-N-(3-hydroxyl-phenyl)-acetamide

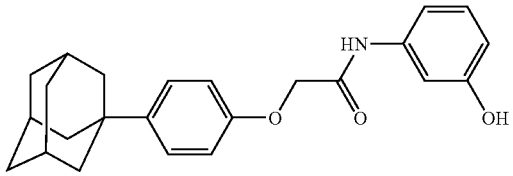 [SMILES: O=C(COc1ccc(C23CC4CC(CC(C4)C2)C3)cc1)Nc1cccc(O)c1]

To a solution of the (4-adamantan-1-yl-phenoxy)-acetic acid (85.9 mg, 0.3 mmol) and 3-amino-phenol (65.5 mg, 0.6 mmol) in DMF (5.0 mL) were added benzotriazol-1-yl-N-oxy-tris(pyrrolidino)phosphonium hexafluorophosphate (PyBOP) (312.2 mg, 0.6 mmol), and N,N-diisopropylethylamine (DIPEA) (0.11 ml, 0.6 mmol). The reaction mixture was stirred at room temperature overnight, and then partitioned between ethyl acetate and brine. The organic phase was dried (MgSO$_4$ anh), and concentrated. Purification by silica gel column chromatography (n-Hexane:EtOAc:MeOH=15:3:1) gave 2-(4-Adamantan-1-yl-phenoxy)-N-(3-hydroxyl-phenyl)acetamide as a white solid (67.6 mg, 59.7% yield).

$^1$H-NMR (CD$_3$OD, 300 Hz) 7.28-7.32 (2H, m, aromatic), 7.19-7.21 (1H, m, aromatic), 7.09-7.14 (1H, m, aromatic), 6.93-7.00 (3H, m, aromatic), 6.56 (1H, dd, J=7.8 Hz & 1.8 Hz, aromatic), 4.60 (2H, s, OCH$_2$CO), 2.06 (3H, m, adamantyl), 1.90-1.91 (6H, m, adamantyl), 1.75-1.86 (6H, m, adamantyl).

EXAMPLE 39

2-(2,4-dichloro-phenoxy)-N-(3-hydroxy-phenyl)acetamide

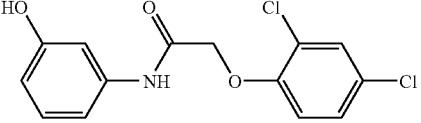

To a solution of the (2,4-dichloro-phenoxyacetic acid (600 mg, 2.71 mmol) and 3-amino-phenol (592 mg, 5.43 mmol) in DMF (20.0 mL) were added benzotriazol-1-yl-N-oxy-trispyrrolidino)-phosphonium hexafluorophosphate (PyBOP) (2.8 g, 5.43 mmol), and N,N-diisopropylethylamine (DIPEA) (0.95 ml, 5.43 mmol). The reaction mixture was stirred at room temperature overnight, and then partitioned between ethyl acetate and brine. The organic phase was dried (MgSO$_4$anh), and concentrated. Purification by silica gel column chromatography (n-Hexane:EtOAc:MeOH=10:3:1) gave 2-(2,4-Dichloro-phenoxy)-N-(3-hydroxy-phenyl)-acetamide as a white solid (837 mg, 99% yield)

$^1$H-NMR (CD$_3$OD, 300 Hz) 7.47 (1H, d, J=2.4 aromatic), 7.28 (1H, m, aromatic), 7.19 (1H, ps t, J=1.8H aromatic), 7.10

(2H, m, aromatic), 6.97 (1H, m, aromatic), 6.57 (1H, dd, J=8.1 & 2.4 Hz, aromatic), 4.73 (2H, s, OCH$_2$CO).

EXAMPLE 40

2-(2,4-dichloro-phenoxy)-N-(3-methanesulfonyl-phenyl)-acetamide

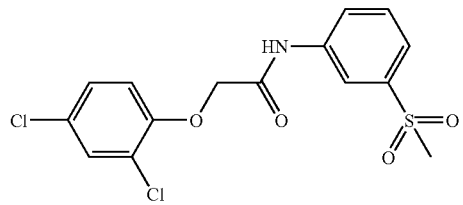 [SMILES: CS(=O)(=O)c1cccc(NC(=O)COc2ccc(Cl)cc2Cl)c1]

To 2,4-dichlorophenoxyacetic acid (110.6 mg, 0.5 mmol), 3-methylsulphonylaniline (128.4 mg, 0.75 mmol), N-(3-dimethylaminopropyl)-N'-ethyl carbodiimide HCl (EDC) (143.8 mg, 0.75 mmol) and 1-hydroxybenzotriazole (HOBt) (102.1 mg, 0.75 mmol) in DMF (5 mL) was added N,N-diisopropylethylamine, redistilled (DIPEA) (0.13 ml, 0.75 mmol). The mixture was stirred overnight, and then partitioned between ethyl acetate and 10% HCl. The organic phase was washed with brine, dried (MgSO$_4$ anh), and concentrated. The residue was purified by silica gel flash column chromatography (CH$_2$CH$_2$:MeOH=15:1) to give 2-(2,4-dichloro-phenoxy)-N-3-methanesulfonyl-phenyl)-acetamide as a white solid (103.0 mg, 55.02% yield).

$^1$H-NMR (CD$_3$OD and DMSO-d$_6$, 300 Hz) 8.41 (1H, m, aromatic-H), 7.99-8.03 (1H, m, aromatic-H), 7.66-7.79 (3H, m, aromatic-H), 7.45 (1H, dd, J=9.0 & 2.4 Hz, aromatic-H), 7.24 (1H, d, J=9.0 Hz, aromatic-H), 4.30 (2H, s, CH$_2$), 3.27 (3H, s, CH$_3$).

EXAMPLE 41

2-(2,4-dichloro-phenoxy)-N-[3-(2-hydroxy-ethanesulfonyl)-phenyl]-acetamide

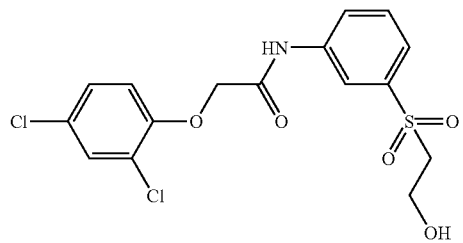 [SMILES: O=C(COc1ccc(Cl)cc1Cl)Nc1cccc(S(=O)(=O)CCO)c1]

To 2,4-dichlorophenoxyacetic acid (110.6 mg, 0.5 mmol), 2-(3-amino-benzenesulfonyl)-ethanol (151.0 mg, 0.75 mmol), N-[3-dimethylaminopropyl)-N'-ethyl carbodiimide HCl (EDC) (143.8 mg, 0.75 mmol) and 1-hydroxybenzotriazole (HOBt) (102.1 mg, 0.75 mmol) in DMF (5 mL) was added N,N-diisopropylethylamine, redistilled (DIPEA) (0.13 ml, 0.75 mmol). The mixture was stirred overnight and then partitioned between ethyl acetate and 10% HCl. The organic phase was washed with brine, dried (MgSO$_4$ anh), and concentrated. The residue was purified by preparative (CH$_2$CH$_2$:MeOH=30:1) to give 2-(2,4-dichloro-phenoxy)-N-[3-(2-hydroxy-ethanesulfonyl)-phenyl]-acetamide as a yell foam (21.5 mg, 10.6% yield).

$^1$H-NMR (CDCl$_3$, 75 Hz) 8.78 (1H, s, NH), 8.20 (1H, s, aromatic-H), 7.89 7.92 (1H, m, aromatic-H), 7.73 (1H, d, J=7.8 Hz, aromatic-H), 7.59 (1H, ps-t, J=7.8 Hz, aromatic-H), 7.45 (1H, d, J=2.4 Hz, aromatic-H), 7.24 7.28 (1H, m, aromatic-H), 6.91 (1H, d, J=9.0H), aromatic-H), 4.66 (2H, s, CH$_2$), 4.03 (2H, J=4.8 Hz, CH$_2$), 3.39 (2H, t, J=4.8 Hz, CH$_2$).

EXAMPLE 42

2-(4-Adamantan-1-yl-phenoxyl)-N-(3-benzoyl-phenyl)-acetamide

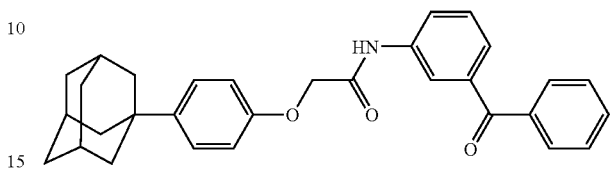

To a solution of the (4-adamantan-1-yl-phenoxy)-acetic acid (143 mg, 0.5 mmol) and (3-amino-phenyl)phenyl-methanone (148 mg, 0.75 mmol) in DMF (5.0 mL) were added 1-[3-dimethylamino)propyl]-3-ethylcarbodiimide hydrochloride (EDC) (144.0 mg, 0.75 mmol), 1-hydroxybenzotriazole hydrate (HOBT) (101 mg, 0.75 mmol), and N,N-diisopropylethylamine (DIPEA) (0.13 ml, 0.75 mmol). The reaction mixture was stirred at room temperature overnight, and then partitioned between ethyl acetate and brine. The organic phase was dried (MgSO$_4$ anh), and concentrated. Purification by silica gel column chromatography (n-Hexane:EtOAc:MeOH=12:3:1) gave 2-(4-Adamantan-1-yl-phenoxy)-N-(3-benzoyl-phenyl)-acetamide as a white solid (173.1 mg, 74.3% yield).

$^1$H-NMR (CDCl$_3$, 300 Hz) 8.44 (1H, s, NH), 8.02 (1H, dd, J=7.8 & 1.2 Hz aromatic), 7.81-7.89 (3H, m, aromatic), 7.45-7.7.63 (5H, m, aromatic), 7.34 (2H, m, aromatic), 6.94 (2H, m, aromatic), 4.61 (2H, s, OCH$_2$CO), 2.10 (3H, m, adamantyl), 1.89-1.90 (6H, m, adamantyl), 1.72-1.82 (6H, m, adamantyl).

EXAMPLE 43

2-[2-(4-Adamantan-1-yl-phenoxy)-acetylamino]-benzoic acid

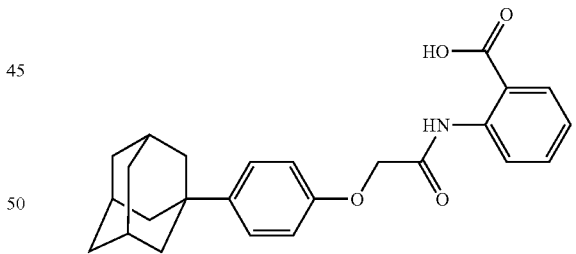

A solution of 2-[2-(4-Adamantan-1-yl-phenoxy)-acetylamino]-benzoic acid methyl ester (30.5 mg, 0.07 mmol) in 1,4-dioxane/H$_2$O (3:1, 3 mL) added LiOHH$_2$O (8.4 mg, 0.2 mmol) at room temperature. The resulting mixture was stirred overnight, and then acidified with 10% HCl to PH 2. Ethyl acetate was added and the organic layer was separated. The organic layer was washed with water, and dried (MgSO$_4$ anh), and concentrated. The residue was purified by silica gel flash column chromatography (n-Hexane:EtOAc:MeOH=6:3:1) to gave 2-[2-(4-Adamant-1-yl-phenoxy)-acetylamino]-benzoic acid as a white solid (18.5 mg, 62.5% yield).

$^1$H-NMR (DMSO-d$_6$, 300 Hz) 8.57 (1H, d, J=8.4 Hz, aromatic-H), 8.01-8.04 (1H, m, aromatic-H), 7.32-7.37 (1H, m, aromatic-H), 7.26 (2H, d, J=8.4 Hz aromatic-H), 7.00-7.05

(3H, m, aromatic-H), 4.58 (2H, s, CH$_2$), 2.03 (3H, m, adamantly-H), 1.81 (6H, m, adamantly-H), 1.71 (6H, m, adamantly-H).

EXAMPLE 44

3-[2-(4-Adamantan-1-yl-phenoxy)-acetylamino]-benzoic acid

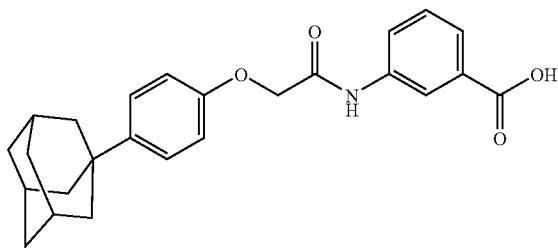 [SMILES: O=C(COc1ccc(C23CC4CC(CC(C4)C2)C3)cc1)Nc1cccc(C(=O)O)c1]

A solution of methyl ester (306 mg, 0.72 mmol) in THF/H$_2$O/1,4-dioxane (1:1:1, 300 mL) added LiOHH$_2$O (66 mg, 1.44 mmol) at room temperature. The resulting mixture was stirred overnight and then acidified with 10% HCl to PH 2. Ethyl acetate was added and the organic layer was separated. After concentration, the residue was purified by silica gel flash column chromatography (n-Hexane:EtOAc:MeOH=15:3:1) to gave 3-[2-(4-Adamant-1-yl-phenoxy)-acetylamino]-benzoic acid as a white solid (152 mg, 43% yield).

$^1$H-NMR (DMSO-d$_6$, 300 Hz) 10.31 (1H, s, NH, 8.27 (1H, s, aromatic), 7.84 (1H, d, J=8.7 Hz, aromatic), 7.67 (1H, d, J=8.1 Hz, aromatic), 7.38 (1H, ps t, J=7.8 Hz, aromatic), 7.27 (2H, m, aromatic), 6.93 (2H, m, aromatic), 4.68 (2H, s, OCH$_2$CO), 2.03 (3H, m, adamantyl), 1.81-1.82 (6H, m, adamantyl), 1.71 (6H, m, adamantyl).

EXAMPLE 45

3-[2-(4-Adamantan-1-yl-phenoxy)acetylamino]-phenyl}-acetic acid

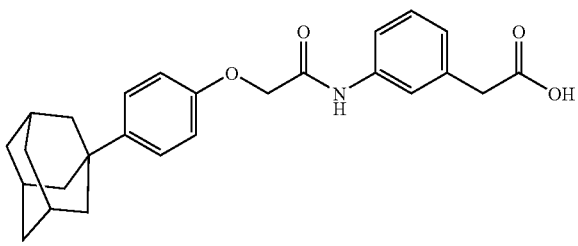 [SMILES: O=C(O)Cc1cccc(NC(=O)COc2ccc(C34CC5CC(CC(C5)C3)C4)cc2)c1]

A solution of methyl ester (185.5 mg, 0.44 mmol) in THF/H$_2$O (1:1, 20 mL) added LiOHH$_2$O (37.1 mg, 0.88 mmol) at room temperature. The resulting mixture was stirred overnight and then acidified with 10% HCl to PH 2. Ethyl acetate was added and the organic layer was separated. After concentration, the residue was purified recrystallization (CH$_2$Cl$_2$+ MeOH/n-Hexane) to gave {3-[2-(4-Adamantan-1-yl-phenoxy)-acetylamino]-phenyl}-acetic acid as a white solid (148.0 mg, 79.9% yield).

$^1$H-NMR (DMSO-d$_6$, 300 Hz) 12.32 (1H, brs, OH), 10.06 (1H, s, NH), 7.54 (2H, m, aromatic), 7.22-7.29 (3H, m, aromatic), 6.90-6.98 (3H, m, aromatic), 4.65 (2H, s, OCH$_2$CO), 3.53 (2H, s, CH$_2$COOH), 2.03 (3H, m, adamantyl), 1.82-1.83 (6H, m, adamantyl), 1.71 (6H, m, adamantyl).

EXAMPLE 46

4-[2-(4-Adamantan-1-yl-phenoxy)-acetylamino]-benzoic acid

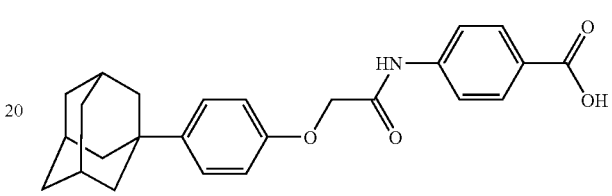

A solution of 4-[2-(4-adamantan-1-yl-phenoxy)-acetylamino]-benzoic acid methyl ester (79.1 mg, 0.16 mmol) in 1,4-dioxane/H$_2$O (3:1, 8 ml) was treated with LiOHH$_2$O (15.9 mg, 0.38 mmol) at room temperature until the reaction was complete, as judged by TLC. The reaction mixture was then acidified with 10% HCl to PH 2, and then partitioned between ethyl acetate and brine. The organic phase was washed with water, dried (MgSO$_4$ anh), and concentrated. The residue was purified by silica gel flash column chromatography (n-Hexane:EtoAc:MeOH=6:3:1) to give 4-[2-(4-Adamantan-1-yl-phenoxy)acetylamino]-benzoic acid as a white solid (40.7 mg, 53.1% yield).

$^1$H-NMR (DMSO-d$_6$, 300 Hz) 10.34 (1H, s, NH), 7.89 (2H, d, J=8.4 Hz, aromatic-H), 7.73 (2H, d, J=8.7 Hz, aromatic-H), 7.27 7.30 (2H, m, aromatic-H), 6.90 6.93 (2H, m, aromatic-H), 4.69 (2H, s, CH$_2$), 2.04 (3H, m, adamantyl-H), 1.82 (6H, m, adamantyl-H), 1.72 (6H, m, adamantyl-H).

EXAMPLE 47

4-[2-(4-tert-butyl-phenoxy)-acetylamino]-benzoic acid

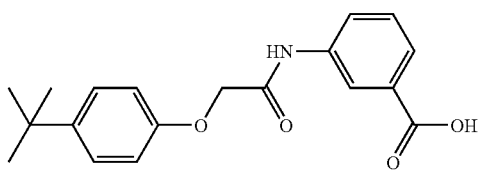 [SMILES: CC(C)(C)c1ccc(OCC(=O)Nc2cccc(C(=O)O)c2)cc1]

The present example was performed in the same manner from 4-[2-(4-tert-butyl-phenoxy)-acetylamino]-benzoic acid methyl ester to give 4-[2-(4-tert-butyl-phenoxy)acetylamino]-benzoic acid as a white solid (68.7 mg, 65.7% yield).

$^1$H-NMR (CDCl$_3$) 8.41 (1H, s, NH), 8.03-8.11 (2H, m, aromatic-H), 7.87 (1H, d, J=7.5 Hz, aromatic-H), 7.45 (1H, m, aromatic-H), 7.36 (2H, d, J=8.7 Hz aromatic-H), 6.92 (2H, m, aromatic-H), 4.60 (2H, s, CH$_2$), 1.31 (9H, s, CH$_3$).

EXAMPLE 48

3-[2-(4-Adamantan-1-yl-phenoxy)-acetylamino]-4-hydroxy-benzoic acid

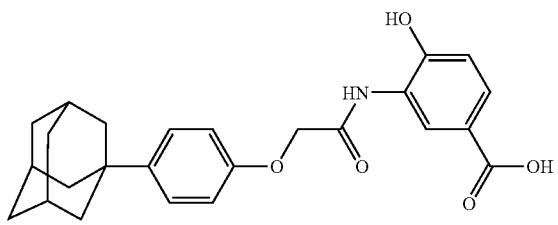 [SMILES: O=C(COc1ccc(C23CC4CC(CC(C4)C2)C3)cc1)Nc1cc(C(=O)O)ccc1O]

3-[2-(4-Adamantan-1-yl-phenoxy)-acetylamino]-4-hydroxy-benzoic acid methyl ester (151.8 mg, 0.35 mmol) in 1,4-dioxane/H$_2$O (10 ml) was treated with KOH (290.7 mg, 5.18 mmol) at 60° C. for 3 h. The reaction mixture was then acidified with 10% HCl to PH 2, and then partitioned between ethyl acetate and brine. The organic phase was washed with water, dried (MgSO$_4$ anh), and concentrated. The residue was purified by silica gel flash column chromatography (CH$_2$CH$_2$:MeOH 4:1) to give 3-[2-(4-Adamantan-1-yl-phenoxy)-acetylamino]-4-hydroxy-benzoic acid as a white solid (110.4 mg, 75.10% yield).

$^1$H-NMR (DMSO-d$_6$, 300 Hz) 9.26 (1H, s, NH), 8.64 (1H, s, aromatic-H), 7.56 (1H, d, J=8.7 Hz, aromatic-H), 7.29 (2H, d, J=8.4H, aromatic-H), 6.90 6.96 (3H, m, aromatic-H), 4.71 (2H, s, CH$_2$), 2.03 (3H, m, adamantly-H), 1.72 1.82 (12H, m, adamantly-H).

EXAMPLE 49

3-[2-(4-tert-butyl-phenoxy)-acetylamino]-4-hydroxy-benzoic acid

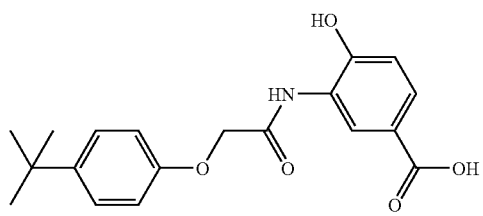 [SMILES: CC(C)(C)c1ccc(OCC(=O)Nc2cc(C(=O)O)ccc2O)cc1]

A 3-[2-(4-Adamantan-1-yl-phenoxy)-acetylamino]-4-hydroxy-benzoic acid methyl ester (151.8 mg, 0.35 mmol) in 1,4-dioxane/H$_2$O (10 ml) was treated with KOH (290.7 mg, 5.18 mmol) at 60° C. for 3 h. The reaction mixture was then acidified with 10% HCl to PH 2, and then partitioned between ethyl acetate and brine. The organic phase was washed with water, dried (MgSO$_4$ anh), and concentrated. The residue was purified by silica gel flash column chromatography (CH$_2$CH$_2$:MeOH=4:1) to give 3-[2-(4-tert-butyl-phenoxy)acetylamino]-4-hydroxy-benzoic acid as a white solid (110.4 mg, 75.10% yield).

$^1$H-NMR (DMSO-d$_6$, 300 Hz) 9.26 (1H, s, NH), 8.64 (1H, s, aromatic-H), 7.56 (1H, d, J=8.7 Hz, aromatic-H), 7.29 (2H, d, J=8.4 Hz, aromatic-H), 6.90 6.96 (3H, m, aromatic-H), 4.71 (2H, s, CH$_2$), 2.03 (3H, m, adamantly-H), 1.72 1.82 (12H, m, adamantly-H).

EXAMPLE 50

3-[2-(4-Adamantan-1-yl-phenoxy)-acetylamino]-isophthalic acid

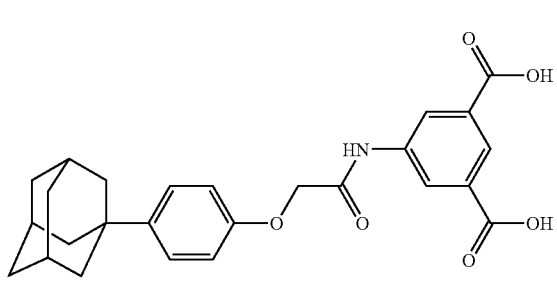 [SMILES: O=C(COc1ccc(C23CC4CC(CC(C4)C2)C3)cc1)Nc1cc(C(=O)O)cc(C(=O)O)c1]

A 3-[2-(4-Adamantan-1-yl-phenoxy)-acetylamino]-isophthalic acid dimethyl ester (158.9 mg, 0.34 mmol) in 1,4-dioxane/H$_2$O (1:1, 3.5 ml) was treated with LiOHH$_2$O (56.2 mg, 1.34 mmol) at room temperature. The reaction mixture was then acidified with 10% HCl to PH 2, and then partitioned between ethyl acetate and brine. The organic phase was washed with water, dried (MgSO$_4$ anh), and concentrated. The residue was purified by silica gel flash column chromatography (CH$_2$CH$_2$:MeOH=5:1) to give 3-[2-(4-Adamantan-1-yl-phenoxy)-acetylamino]-isophthalic acid as a white solid (161.7 mg, 100% yield).

$^1$H-NMR (CD$_3$OD, 300 Hz) 8.52 (2H, m, aromatic-H), 8.40 (1H, m, aromatic-H), 7.30-7.33 (2H, m, aromatic-H), 6.97-7.00 (2H, m, aromatic-H), 4.67 (2H, s, CH$_2$), 2.06 (3H, m, adamantly-H), 1.90 (6H, m, adamantly-H), 1.80 (6H, m, adamantly-H).

EXAMPLE 51

3-[2-(4-fluoro-phenoxy)acetylamino]-benzoic acid

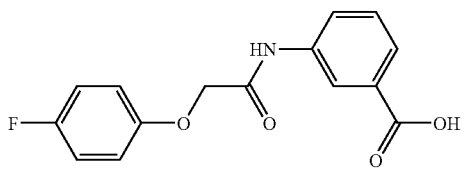

A methyl ester (134.3 mg, 0.45 mmol) in THF/H$_2$O (1:1, 6 mL) was treated with LiOHH$_2$O (37.8 mg, 0.90 mmol) at room temperature. The reaction mixture was then acidified with 10% HCl to PH 2, and then partitioned between ethyl acetate and brine. The organic phase was washed with water, dried (MgSO$_4$ anh), and concentrated. The residue was purified by silica gel column chromatography (CH$_2$CH$_2$:MeOH=6:1) to give 3-[2-(4-fluoro-phenoxy)-acetylamino]-benzoic acid as a white solid (108.3 mg, 83.24% yield).

$^1$H-NMR (DMSO-d$_6$) 10.31 (1H, s, NH), 8.27 (1H, s, aromatic-H), 7.84 (1H, d, J=8.7 Hz aromatic-H), 7.67 (1H, d, J=8.1 Hz, aromatic-H), 7.41 (1H, ps-t, J=7.8 Hz, aromatic-H), 7.12-7.18 (2H, m, aromatic-H), 7.01-7.05 (2H, m, aromatic-1H), 4.71 (2H, s, CH$_2$).

EXAMPLE 52

3-[2-(4-chloro-phenoxy)-acetylamino]-benzoic acid

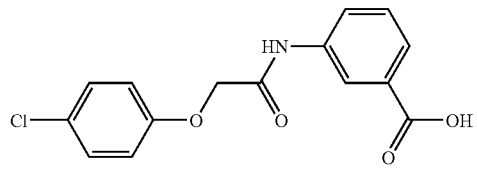 [SMILES: O=C(COc1ccc(Cl)cc1)Nc1cccc(C(=O)O)c1]

The present example was performed in the same manner from 3-[2-(4-chloro-phenoxy)-acetylamino]-benzoic acid methyl ester to give 3-[2-(4-chloro-phenoxy)-acetylamino]-benzoic acid as a white solid (70.3 mg, 74.2% yield).

$^1$H-NMR (DMSO-d$_6$) 10.30 (1H, s, NH), 8.26 (1H, s, aromatic-H), 7.83 (1H, d, J=7.8 Hz, aromatic-H), 7.66 (1H, d, J=7.2 Hz, aromatic-H), 7.44 (1H, ps-t, J=7.8 Hz, aromatic-H), 7.33-7.36 (2H, m, aromatic-H), 7.01-7.04 (2H, m, aromatic-H), 4.72 (2H, s, CH$_2$).

EXAMPLE 53

3-[2-(2,4-dichloro-phenoxy)-acetylamino]-benzoic acid

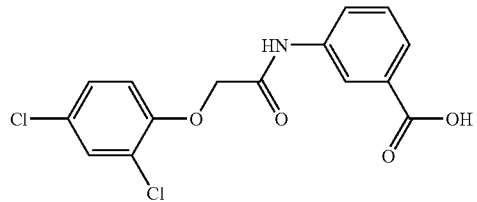 [SMILES: O=C(COc1ccc(Cl)cc1Cl)Nc1cccc(C(=O)O)c1]

The present example was performed in the same manner from 3-[2-(2,4-dichloro-phenoxy)-acetylamino]-benzoic acid methyl ester to give 3-[2-(2,4-dichloro-phenoxy)-acetylamino]-benzoic acid 3-[2-(2,4-dichloro-phenoxy)-acetylamino]-benzoic acid as a white solid (583.7 mg, 85.8% yield).

$^1$H-NMR (CD$_3$OD) 8.25 (1H, s, aromatic-H), 7.78-7.86 (2H, m, aromatic-H), 7.41-7.48 (2H, m, aromatic-H), 7.29 (1H, dd, J=9.0&2.4H, aromatic-H), 7.10 (1H, d, J=9.3 Hz, aromatic-H), 4.77 (2H, s, CH$_2$).

EXAMPLE 54

2-[2-(2,4-dichloro-phenoxy)-acetylamino]-benzoic acid

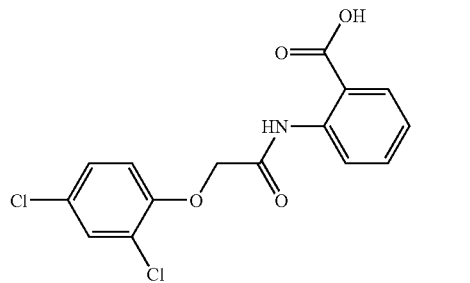 [SMILES: O=C(COc1ccc(Cl)cc1Cl)Nc1ccccc1C(=O)O]

2-[2-(2,4-dichloro-phenoxy)-acetylamino]-benzoic acid methyl ester (94.6 mg, 0.27 mmol) in THF/H$_2$O (3:1, 25 mL) was treated with LiOHH$_2$O (22.7 mg, 0.54 mmol) at room temperature. The reaction mixture was then acidified with 10% HCl to PH 2, and added ethyl acetate and brine. The organic phase was washed with water, dried (MgSO$_4$ anh), and concentrated. The residue was purified by silica gel column chromatography (CH$_2$Cl$_2$:MeOH=6:1) to give 2-[2-(2,4-dichloro-phenoxy)-acetylamino]-benzoic acid as a white solid (81.7 mg, 88.9% yield).

$^1$H-NMR (DMSO-d$_6$, 300 Hz) 12.64 (1H, s, NH), 8.59 (1H, d, J=8.7 Hz, aromatic-H), 8.02 (1H, dd, J=8.1&1.2 Hz, aromatic-H), 7.61 (1H, d, J=3.0 Hz, aromatic-H), 7.53 (1H, m, aromatic-H), 7.37 (1H, dd, J=8.7&2.4 Hz, aromatic-H), 7.11-7.20 (2H, m, aromatic-H), 4.86 (2H, s, CH$_2$).

EXAMPLE 55

4-[2-(2,4-dichloro-phenoxy)acetylamino]-benzoic acid

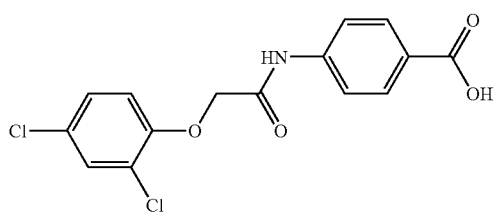 [SMILES: O=C(COc1ccc(Cl)cc1Cl)Nc1ccc(C(=O)O)cc1]

4-[2-(2,4-dichloro-phenoxy)-acetylamino]-benzoic acid methyl ester (127.7 mg, 0.36 mmol) in THF/H$_2$O (3:1, 9 mL) was treated with LiOHH$_2$O (30.2 mg, 0.72 mmol) at room temperature. The reaction mixture was then acidified with 10% HCl to PH 2, and added ethyl acetate and brine. The organic phase was washed with water, dried (MgSO$_4$ anh), and concentrated. The residue was purified by silica gel column chromatography (CH$_2$Cl$_2$:MeOH=4:1) to give 4-[2-(2,4-dichloro-phenoxy)-acetylamino]-benzoic acid as a white solid (86.4 mg, 70.6% yield).

$^1$H-NMR (DMSO-d$_6$, 300 Hz) 10.44 (1H, s, NH), 7.88 (2H, d, J=8.4 Hz, aromatic-H), 7.58-7.64 (3H, m, aromatic-H), 7.33-7.37 (1H, m, aromatic-H), 7.09 (1H, d, J=9.3 Hz, aromatic-H), 4.87 (2H, s, CH$_2$).

EXAMPLE 56

3-[2-(2,4,5-trichloro-phenoxy)-acetylamino]-benzoic acid

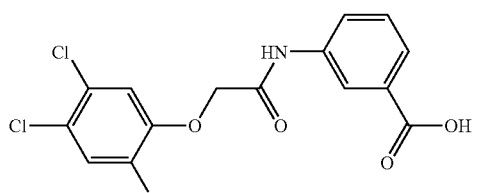

The present example was performed in the same manner from 3-[2-(2,4,5-trichloro-phenoxy)acetylamino]-benzoic acid methyl ester to give 3-[2-(2,4,5-trichloro-phenoxy)-acetylamino]-benzoic acid as a white solid (89.3 mg, 77.2% yield).

$^1$H-NMR (DMSO-d$_6$) 10.56 (1H, s, NH), 8.25 (1H, s, aromatic-H), 7.83 (1H, s, aromatic-H), 7.77 (1H, d, J=7.8 Hz, aromatic-H), 7.70 (1H, d, J=7.8 Hz, aromatic-H), 7.47 (1H, s, aromatic-H), 7.32 (1H, ps-t, J=7.8 Hz, aromatic-H), 4.98 (2H, s, CH$_2$).

EXAMPLE 57

3-[2-(4-bromo-phenoxy)-acetylamino]-benzoic acid

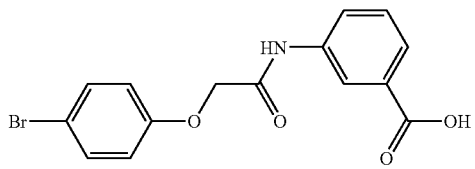 [SMILES: O=C(COc1ccc(Br)cc1)Nc1cccc(C(=O)O)c1]

The present example was performed in the same manner from 3-[2-(4-bromo-phenoxy)acetylamino]-benzoic acid methyl ester to give 3-[2-(4-bromo-phenoxy)-acetylamino]-benzoic acid as a white solid (44.6 mg, 51% yield).

$^1$H-NMR (CD$_3$OD, 300 Hz) 8.26 (1H, m, aromatic), 7.86 (1H, m, aromatic), 7.79 (1H, d, J=8.1 Hz, aromatic), 7.41-7.46 (3H, nm, aromatic), 6.99 (2H, m, aromatic), 4.68 (2H, s, OCH$_2$CO).

EXAMPLE 58

3-[2-(4-iodo-phenoxy)-acetylamino]-benzoic acid

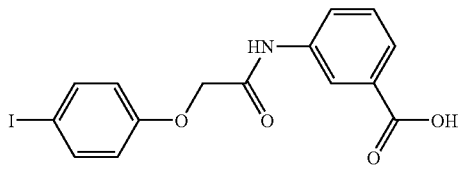 [SMILES: O=C(COc1ccc(I)cc1)Nc1cccc(C(=O)O)c1]

The present example was performed in the same manner from 3-[2-(4-iodo-phenoxy)-acetylamino]-benzoic acid methyl ester to give 3-[2-(4-iodo-phenoxy)-acetylamino]-benzoic acid as a white solid (64.4 mg, 67.7% yield).

$^1$H-NMR (DMSO-d$_6$) 10.15 (1H, s, NH), 8.25 (1H, s, aromatic-H), 7.85 (1H, d, J=8.1 Hz, aromatic-H), 7.60-7.67 (3H, m, aromatic-H), 7.43 (1H, ps-t, J=8.1 Hz, aromatic-H), 6.86 (2H, d, J=8.7 Hz, aromatic-H), 4.72 (2H, s, CH$_2$).

EXAMPLE 59

3-(2-biphenyl-4-yl-acetylamino)-benzoic acid

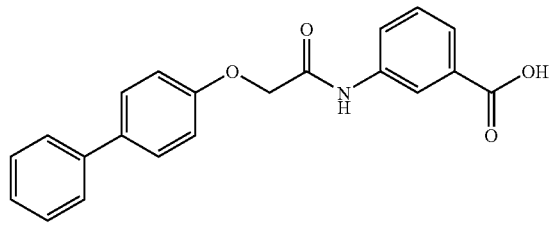 [SMILES: O=C(COc1ccc(-c2ccccc2)cc1)Nc1cccc(C(=O)O)c1]

3-(2-biphenyl-4-yl-acetylamino)-benzoic acid methyl ester (133.6 mg, 0.39 mmol) in THF/H$_2$O (1:1, 4 mL) was treated with LiOHH$_2$O (32.7 mg, 0.78 mmol) at room temperature. The reaction mixture was then acidified with 10% HCl to PH 2. Resulting mixture was collected by filtration, and recrystallized with mixture of CH$_2$Cl$_2$ and MeOH to give 3-(2-biphenyl-4-yl-acetylamino)-benzoic acid as a white solid (74.4 mg, 58.1% yield).

$^1$H-NMR (DMSO-d$_4$, 300 Hz) 12.96 (1H, s, CO$_2$H), 10.44 (1H, s, NH), 8.26 (1H, s, aromatic-H), 7.86 (1H, d, J=8.7 Hz, aromatic-H), 7.61-7.66 (5H, m, aromatic-H), 7.43-7.48 (5H, m, aromatic-H), 7.32-7.40 (1H, m, aromatic-H), 3.71 (2H, s, CH$_2$).

EXAMPLE 60

3-[2-(4-acetyl-phenoxy)-acetylamino]-benzoic acid

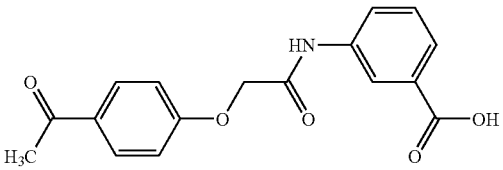 [SMILES: CC(=O)c1ccc(OCC(=O)Nc2cccc(C(=O)O)c2)cc1]

Methyl ester (113 mg, 0.35 mmol) in THF/H$_2$O (1:1, 14 mL) was treated with LiOHH$_2$O (29 mg, 0.69 mmol) at room temperature. The reaction mixture was then acidified with 10% HCl to PH 2, added EtoAC, and an organic layer was separated. After concentrated, The residue was purified by silica gel column chromatography (CH$_2$Cl$_2$:MeOH=15:1) to give 3-[2-(4-acetyl-phenoxy)-acetylamino]-benzoic acid as a white solid (73 mg, 67% yield).

$^1$H-NMR (CD$_3$OD, 300 Hz) 8.26 (1H, m, aromatic), 8.00 (2H, m, aromatic), 7.86 (1H, m, aromatic), 7.79 (1H, d, J=8.1 Hz, aromatic), 7.43 (1H, ps t, J=8.1 Hz, aromatic), 7.14 (2H, m, aromatic), 4.79 (2H, s, OCH$_2$CO), 2.55 (3H, s, COCH$_3$).

EXAMPLE 61

2-(4-adamantan-1-yl-phenoxy)-N-[3-(1H-tetrazole-5-yl)phenyl]-acetamide

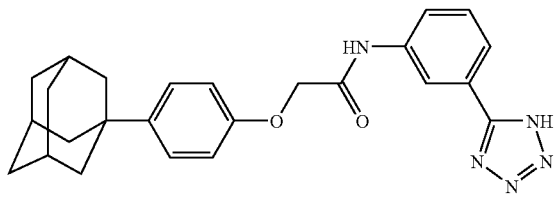 [SMILES: O=C(COc1ccc(C23CC4CC(CC(C4)C2)C3)cc1)Nc1cccc(-c2nnn[nH]2)c1]

A mixture of 24-Adamantan-1-yl-phenoxy)-N-(3-cyano-phenylacetamide (165.9 mg, 0.43 mmol), sodium azide (83.9 mg, 1.29 mmol) and triethylamine hydrochloride (89.5 mg, 0.65 mmol) in N-methylpyrrolidone (6 ml) (NMP) was stirred at 150° C. under nitrogen overnight. After cooling, the reaction mixture was diluted with water, acidified to PH 1 with 10% v/v hydrochloric acid, and extracted with ethyl acetate. The organic phase was washed with brine, dried (MgSO$_4$ anh), and concentrated. The residue was purified by silica gel flash column chromatography (CH$_2$CH$_2$:MeOH=6:1) to give 2-(4-adamantan-1-yl-phenoxy)-N-[3-(1H-tetrazole-5-yl)phenyl]-acetamide as a solid (30.3 mg, 16.3% yield).

$^1$H-NMR (DMSO-d$_6$, 300 Hz) 10.36 (1H, s, NH), 8.46 (1H, s, aromatic-H), 7.81 (1H, d, J=8.1 Hz, aromatic-H), 7.73 (1H, d, J=7.8 Hz, aromatic-H), 7.55 (1H, ps-t, J=8.1 Hz, aromatic-H), 7.29 (2H, d, J=8.7 Hz, aromatic-H), 6.94 (2H, d, J=9.3 Hz, aromatic-H), 4.71 (2H, s, CH$_2$), 2.03 (3H, m, adamantly-H), 1.83 (6H, m, adamantly-H), 1.71 (6H, m, adamantly-H).

EXAMPLE 62

2-(2,4-dichloro-phenoxy)-N-[3-(1H-tetrazole-5-yl)-phenyl]-acetamide

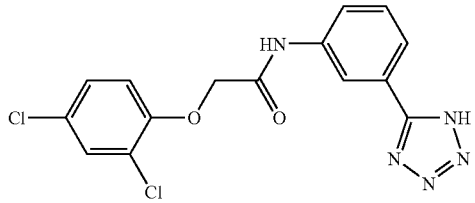 [SMILES: O=C(COc1ccc(Cl)cc1Cl)Nc1cccc(-c2nnn[nH]2)c1]

A mixture of N-(3-cyano-phenyl)-2-(2,4-dichloro-phenoxyacetamide (70.0 mg, 0.22 mmol), sodium azide (42.9 mg, 0.66 mmol) and triethylamine hydrochloride (45.4 mg, 0.33 mmol) in N-methylpyrrolidone (6 ml) (NMP) was stirred at 150° C. under nitrogen overnight. After cooling, the reaction mixture was diluted with water, acidified to PH 1 with 10% v/v hydrochloric acid, and extracted with ethyl acetate. The organic phase was washed with brine, dried (MgSO$_4$ anh), and concentrated. The residue was purified by silica gel flash column chromatography (CH$_2$CH$_2$:MeOH=3:1) to give 2-(2,4-dichloro-phenoxy)-N-[3-(1H-tetrazole-5-yl)-phenyl]-acetamide as a solid (57.2 mg, 71.6% yield).

$^1$H-NMR (DMSO-d$_6$, 300 Hz) 10.31 (1H, s, NH), 8.21 (1H, s, aromatic-H), 7.64-7.72 (2H, m, aromatic-H), 7.61 (1H, d, J=2.4 Hz, aromatic-H), 7.34-7.40 (2H, m, aromatic-H), 7.13 (1H, d, J=9.0 Hz, aromatic-H), 4.89 (2H, s, CH$_2$).

EXAMPLE 63 carbamic acid 3-[2-(2,4-dichloro-phenoxy)-acetylamino]-phenylester

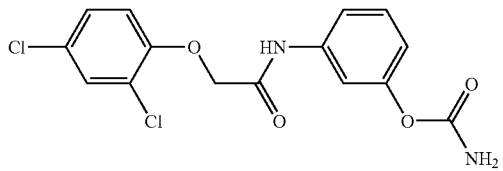 [SMILES: NC(=O)Oc1cccc(NC(=O)COc2ccc(Cl)cc2Cl)c1]

To a stirred solution of mixture of 2-(2,4-Dichloro-phenoxy)-N-(3-hydroxy-phenyl)-acetamide (95.2 mg, 0.3 mmol) in CH$_2$Cl$_2$ (1.0 mL) was added trichloroacetyl (0.09 ml, 0.76 mmol) at 0° C. and the solution was stirred at room temperature until the reaction was complete, as judged by TLC. The reaction mixture was added aluminum oxide and CH$_2$Cl$_2$ (10 mL) and then stirred at room temperature for 0.5 h. The aluminum oxide was removed by filtration and the filtrate was concentrated in vacuo. Purification by preparative TLC (n-Hexane:EtOAc:MeOH=6:3:1) gave Carbamic acid 3-[2-(4-Adamantan-1-yl-phenoxyl)-acetylamino]-phenyl ester as a white solid (42.0 mg, 39.4% yield).

$^1$H-NMR (DMSO-d$_6$, 300 Hz) 10.27 (1H, s, NH), 7.60 (1H, d, J=2.4 Hz, aromatic), 7.45 (1H, m, aromatic), 7.27-7.38 (3H, m, aromatic), 7.16 (1H, brs, NH$_2$), 7.10 (1H, d, J=8.7 Hz, aromatic), 6.91 (1H, brs, NH$_2$), 6.81 (1H, d, J=8.1 Hz aromatic), 4.86 (2H, s, OCH$_2$CO).

Example 64 sulfamic acid 3-[2-(2,4-dichloro-phenoxy)-acetylamino]-phenyl ester

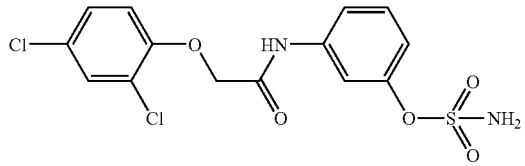 [SMILES: NS(=O)(=O)Oc1cccc(NC(=O)COc2ccc(Cl)cc2Cl)c1]

Sulfamoyl chloride was prepared by the dropwise addition of formic acid (0.03 mL, 0.80 mmol) to neat chlorosulfonyl isocyanate (0.07 mg, 0.80 mmol) at 0° C. with rapid stirring. Gas was evolved during the addition process. The viscous mixture was stirred for 5 min at 0° C. during which time it solidified. Dichloromethane (0.2 mL) was added and the solution of the 2-(2,4-Dichloro-phenoxy)-N-(3-hydroxy-phenyl)-acetamide (100 mg, 0.32 mmol) and pyridine (0.26 mL, 3.2 mmol) in dichloromethane (0.3 mL) was added dropwise. The reaction mixture was warmed 25 C and stirred for 18 h. The reaction was quenched by the successive addition of ethyl acetate (5 mL) and H$_2$O (3 mL). The biphasic mix was poured into ethyl acetate (10 mL) and H$_2$O (5 mL) and the organic layer was separated. After concentration, the residue was purified by preparative TLC (n-Hexane EtOAc: MeOH=6:3:1) to gave Sulfamic acid 3-[2-(4-Adamantan-1-yl-phenoxyl)acetylamino]-phenyl ester as a white solid (19.3 mg, 15.4% yield).

$^1$H-NMR (CD$_3$OD, 300 Hz) 7.70 (1H, m, aromatic), 7.47 (2H, m, aromatic), 7.38 (2H, m, aromatic), 7.28 (2H, m, aromatic), 7.09 (2H, m, aromatic), 4.76 (2H, m, OCH$_2$CO).

EXAMPLE 65

3-[2-(4-adamantan-1-yl-phenoxy)-acetylamino]-4-hydroxy-benzamide

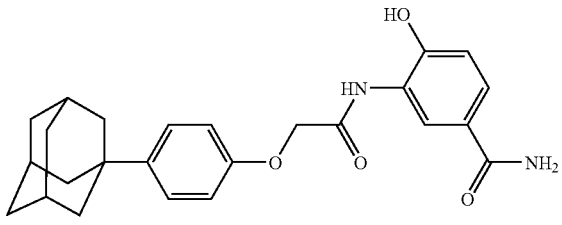 [SMILES: NC(=O)c1ccc(O)c(NC(=O)COc2ccc(C34CC5CC(CC(C5)C3)C4)cc2)c1]

Ammonium chloride (6.5 mg, 0.12 mmol) in anhydrous toluene 2 ml was treated with trimethyl aluminium (in 2.0 M Hexane, 0.26 ml, 0.51 mmol) under nitrogen. After 0.25 h, It was added 3-[2-(4-adamantan-1-yl-phenoxy)-acetylamino]-4-hydroxy-benzoic acid methyl ester (50.1 mg, 0.12 mmol) in toluene 4 ml. The mixture was stirred for 3 h at 80° C. After cooling, the reaction mixture was treated with diluted HCl until no foaming more. The reaction mixture was separated with ethyl acetate and sodium bicarbonate. The organic phase was washed by brine, dried (MgSO$_4$ anh), and concentrated. The residue was purified by preparative TLC(CH$_2$Cl$_2$: MeOH=15:1) to give 3-[2-(4-adamantan-1-yl-phenoxy)-acetylamino]-4-hydroxy-benzamide as a white-solid (12.9 mg, 25.6%-yield).

$^1$H-NMR (CDCl$_3$+CD$_3$OD, 300 Hz) 8.26 (1H, d, J=2.4 Hz, aromatic-H), 7.23 (1H, d, J=2.1 Hz, aromatic-H), 6.99 (2H, d, J=9.3 Hz, aromatic-H), 6.64 (2H, d, J=9.3 Hz, aromatic-H), 6.59 (1H, d, J=8.7 Hz, aromatic-H), 4.25 (2H, s, CH₂), 1.75 (3H, m, adamantly-H), 1.56 (6H, m, adamantly-H), 1.44 (6H, m, adamantly-H).

EXAMPLE 66

3-[2-(4-adamantan-1-yl-phenoxy)-acetylamino]-4-hydroxy-N,N-dimethyl-benzamide

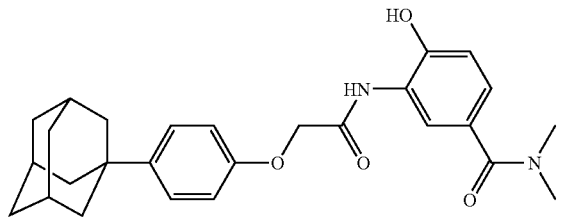 [SMILES: CN(C)C(=O)c1ccc(O)c(NC(=O)COc2ccc(C34CC5CC(CC(C5)C3)C4)cc2)c1]

Dimethyl amine (0.06 ml, 0.12 mmol) in anhydrous toluene 2 ml was treated with trimethyl aluminium (in 2.0 M Hexane, 0.15 ml, 0.31 mmol) under nitrogen. After 0.25 h, It was added 3-[2-(4-adamantan-1-yl-phenoxy)acetylamino]-4-hydroxy-benzoic acid methyl ester (30.1 mg, 0.07 mmol) in toluene 4 ml. The mixture was stirred for 3 h at 80° C. After cooling, the reaction mixture was treated with diluted HCl until no foaming more. The reaction mixture was separated with ethyl acetate and sodium bicarbonate. The organic phase was washed by brine, dried (MgSO₄ anh), and concentrated. The residue was purified by preparative TLC(Hexane:EtoAC:MeOH=15:3:1) to give 3-[2-(4-adamantan-1-yl-phenoxy)-acetylamino]-4-hydroxy-N,N-dimethyl-benzamide as a white solid (10.4 mg, 23.2% yield).

¹H-NMR (CDCl₃, 300 Hz) 8.85 (1H, s, NH), 7.70 (1H, s, aromatic-H), 7.32 (2H, d, J=8.4 Hz, aromatic-H), 7.03-7.05 (1H, m, aromatic-H), 6.93 (2H, d, J=8.7 Hz, aromatic-H), 6.85 (1H, d, J=7.2 Hz, aromatic-H), 4.61 (2H, s, CH₂), 3.07 (6H, s, CH₃), 2.09 (3H, m, adamantly-H), 1.89 (6H, m, adamantly-H), 1.76 (6H, m, adamantly-H).

EXAMPLE 67

3-[2-(4-adamantan-1-yl-phenoxy)-acetylamino]-N-furan-2-ylmethyl-4-hydroxy-benzamide

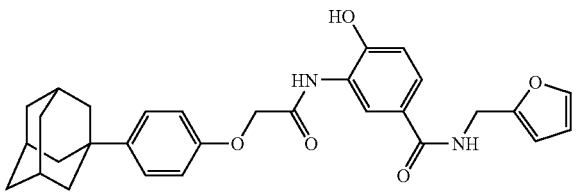 [SMILES: O=C(COc1ccc(C23CC4CC(CC(C4)C2)C3)cc1)Nc1cc(C(=O)NCc2ccco2)ccc1O]

furfuryl amine (6.8 mg, 0.07 mmol, 0.07 ml) in anhydrous toluene 1 ml was treated with trimethyl aluminium (in 2.0 M Hexane, 0.15 ml, 0.31 mmol) under nitrogen. After 0.25 h, It was added 3-[2-(4-adamantan-1-yl-phenoxyacetyl)-amino]-4-hydroxy-benzoic acid methyl ester (30.1 mg, 0.07 mmol) in toluene 8 ml. The mixture was stirred for 3 h at 80° C. After cooling, the reaction mixture was treated with diluted HCl until no foaming more. The reaction mixture was separated with ethyl acetate and sodium bicarbonate. The organic phase was washed by brine, dried (MgSO₄ anh), and concentrated. The residue was purified by preparative TLC(CH₂Cl₂:MeOH=15:1) to give 3-[2-(4-adamantan-1-yl-phenoxy)acetylamino]-N-furan-2-ylmethyl-4-hydroxy-benzamide as a white solid (15.4 mg, 44.0% yield).

¹H-NMR (CDCl₃, 300 Hz) 8.71 (1H, s, N), 7.76 (1H, s, aromatic-H), 7.48 (1H, d, J=9.0 Hz, aromatic-H), 7.33-7.38 (3H, m, aromatic-H), 7.04 (1H, d, J=8.1 Hz, aromatic-H), 6.95 (2H, d, J=9.0 Hz, aromatic-H), 6.44 (1H, s, NH), 6.32 (2H, d, J=8.7 Hz, aromatic-H), 4.62-4.69 (4H, m, CH₂), 2.10 (3H, m, adamantly-H), 1.90 (6H, m, adamantly-H), 1.77 (6H, m, adamantly-H).

EXAMPLE 68

3-[2-(4-adamantan-1-yl-phenoxy)-acetylamino]-N-(2-dimethylamino-ethyl)-4-hydroxy-benzamide

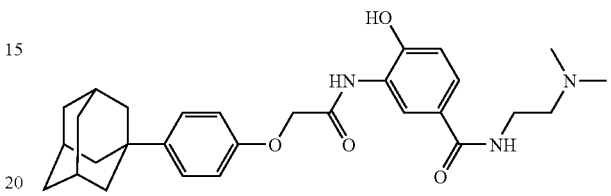

3-[2-(4-adamantan-1-yl-phenoxy)acetylamino]-4-hydroxy-benzoic acid (60.1 mg, 0.14 mmol) and PyBOP (148.3 mg, 0.29 mmol) in DMF 3.0 ml was added N,N-dimethylethylenediamine (25.1 mg, 0.29 mmol, 0.03 ml) and DIPEA (0.05 ml, 0.29 mmol) at room temperature. The reaction mixture was separated with ethyl acetate and sodium bicarbonate. The organic phase was dried (MgSO₄ anh), and concentrated. The residue was purified by preparative TLC (CH₂C₂:MeOH=7:1) to give 3-[2-(4-adamantan-1-yl-phenoxy)-acetylamino]-N-(2-dimethylamino-ethyl)-4-hydroxy-benzamide as a yellow solid (20.2 mg, 28.7% yield).

¹H-NMR (MEOD, 300 Hz) 8.26 (1H, m, aromatic), 7.85 (1H, dd, J=1.8&9.0 Hz, aromatic-H), 7.45-7.47 (1H, m, aromatic-H), 7.36 (2H, d, J=9.0 Hz, aromatic-H), 7.02 (2H, d, J=6.6 Hz, aromatic-H), 4.73 (2H, s, CH₂), 3.63 (2H, t, J=6.6 Hz, CH₂), 2.93 (2H, t, J=6.6 Hz, CH₂), 2.60 (6H, s, CH₃), 2.08 (3H, m, adamantly-H), 1.91 (6H, m, adamantly-H), 1.81 (6H, m, adamantly-H).

EXAMPLE 69

3-[2-(4-adamantan-1-yl-phenoxy)acetylamino]-4-hydroxy-N-3-morpholine-4-yl-propyl)-benzamide

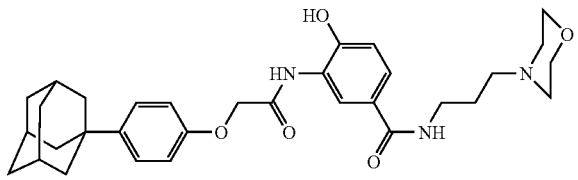 [SMILES: O=C(COc1ccc(C23CC4CC(CC(C4)C2)C3)cc1)Nc1cc(C(=O)NCCCN2CCOCC2)ccc1O]

3-[2-(4-adamantan-1-yl-phenoxy)acetylamino]-4-hydroxy-benzoic acid (50.1 mg, 0.12 mmol), HATU (68.5 mg, 0.18 mmol) in DMF 3.0 ml was added N-(aminopropyl)morpholine (0.18 mmol, 0.03 ml) and DIPEA (0.03 ml, 0.18 mmol) at room temperature. The reaction mixture was separated with ethyl acetate and sodium bicarbonate. The organic phase was dried (MgSO₄ anh), and concentrated. The residue was purified by preparative TLC(CH₂Cl₂:MeOH=15:1) to give 3-[2-(4-adamantan-1-yl-phenoxy)-acetylamino]-N-(2-dimethylamino-ethyl)-4-hydroxy-benzamide as a yellow solid (9.5 mg, 14.5% yield).

¹H-NMR (MEOD, 300 Hz) 8.57 (1H, d, J=2.4 Hz, aromatic), 7.51 (1H, dd, J=2.4&8.7 Hz, aromatic-H), 7.33 (2H, d, J=8.7 Hz, aromatic-H), 6.98 (2H, d, J=8.7 Hz, aromatic-H), 6.92 (1H, d, J=8.7 Hz, aromatic-H), 4.67 (2H, s, CH$_2$), 3.76-3.81 (4H, m, aliphatic), 6.92 (2H, t, J=6.9 Hz, aliphatic), 2.71-2.79 (6H, m, aliphatic), 2.07 (3H, m, adamantly-H), 1.91 (8H, m, adamantly-H and aliphatic), 1.80 (6H, m, adamantly-H).

EXAMPLE 70

3-[2-(4-adamantan-1-yl phenoxy)-acetylamino]-N-(4-chloro-phenyl)-benzamide

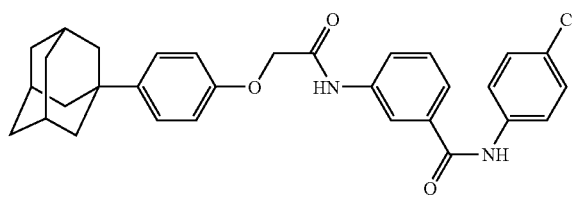 [SMILES: O=C(COc1ccc(C23CC4CC(CC(C4)C2)C3)cc1)Nc1cccc(C(=O)Nc2ccc(Cl)cc2)c1]

To a solution of 3-[2-(4-adamantan-1-yl-phenoxy)-acetylamino]-benzoic acid (20 mg, 0.049 mmol), 4-chloro aniline (9.4 mg, 0.073 mmol) and DIPEA (9.56 mg, 0.073 mmol) in DMF (5 mL) was added EDC (14.18 mg, 0.073 mmol) and HOBt (9.99 mg, 0.073 mmol) at room temperature and continued stirring for 16 h at room temperature. Reaction mixture was diluted with ethyl acetate and sequentially washed with aqueous sodium bicarbonate, brine and water, and dried over MgSO$_4$. The solvent was filtered and evaporated under reduced pressure to afford a crude solid, which was purified by column chromatography on silica gel (EtoAC:Hexane=1:5) to give 3-[2-adamantan-1-yl-phenoxy)-acetylamino]-N-(4-chloro-phenyl)-benzamide as a colorless crystals (15 mg, yield: 59%).

$^1$H NMR (DMSO-d$_6$, 300 MHz) 10.39 (1H, s, OCH$_2$CONH), 10.27 (1H, s, PhCONHPh), 8.16 (1H, s, aromatic), 7.89 (1H, d, J=8.7 Hz, aromatic), 7.80 (2H, d, J=9.0 Hz, aromatic), 7.66 (1H, d, J=7.8 Hz, aromatic), 7.45 (3H, m, aromatic), 7.28 (2H, d, J=8.4 Hz, aromatic), 6.93 (2H, d, J=8.4 Hz, aromatic), 4.69 (2H, s, OCH$_2$), 2.03 (3H, s, adamantyl), 1.83 (6H, s, adamantyl), 1.71 (6H, s, adamantyl).

EXAMPLE 71

3-[2-(4-adamantan-1-yl-phenoxy)-acetylamino]-N-(3-trifluoromethyl-phenylbenzamide

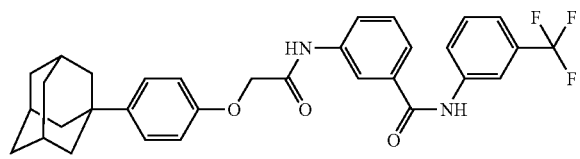 [SMILES: O=C(COc1ccc(C23CC4CC(CC(C4)C2)C3)cc1)Nc1cccc(C(=O)Nc2cccc(C(F)(F)F)c2)c1]

To a solution of 3-[2-(4-adamantan-1-yl-phenoxy)-acetylamino]-benzoic acid (50.0 mg, 0.13 mmol), 3-trifluoromethyl-phenylamine (31.5 mg, 0.03 ml 0.20 mmol), EDC (37.4 mg, 0.20 mmol) and HOBt (30.0 mg, 0.20 mmol) in DMF 1.3 mL was added DIPEA (0.04 ml, 0.20 mmol). Reaction mixture was stirred, and separated by ethyl acetate and 10% HCl. It was sequentially washed with brine and water, and dried over MgSO$_4$. The solvent was filtered and evaporated under reduced pressure to afford a crude solid, which was purified by silica gel flash column chromatography (EtoAC:Hexane=1:3) to give 3-[2-(4-adamantan-1-yl-phenoxy)-acetylamino]-N-3-trifluoromethyl-phenyl)-benzamide as a white solid (39.1 mg, 54.9% yield).

$^1$H-NMR (CDCl$_3$, 300 Hz) 8.47 (1H, s, NH), 8.13-8.16 (2H, m, aromatic-H), 7.96 (1H, s, NH), 7.89 (1H, d, J=7.8 Hz, aromatic-H), 7.79-7.81 (1H, m, aromatic-H), 7.67 (1H, d, J=7.8 Hz, aromatic-H), 7.46-7.52 (2H, m, aromatic-H), 7.40-7.43 (1H, m, aromatic-H), 7.32-7.36 (2H, m, aromatic-H), 6.95 (2H, d, J=8.7 Hz, aromatic-H), 4.62 (2H, s, CH$_2$), 2.10 (3H, m, adamantly-H), 1.72-1.90 (12H, m, adamantly-H).

EXAMPLE 72

3-[2-(4-adamantan-1-yl-phenoxy)-acetylamino]-N-naphtalene-2-yl-benzamide

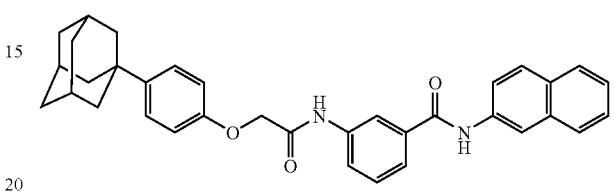

To a solution of 3-[2-(4-adamantan-1-yl-phenoxy)-acetylamino]-benzoic acid (20 mg, 0.049 mmol), 2-naphthylamine (10.59 mg, 0.073 mmol) and DIPEA (9.56 mg, 0.073 mmol) in DMF 1 mL was added EDC (14.18 mg, 0.073 mmol) and HOBt (9.99 mg, 0.073 mmol) at room temperature and continued string for 16 h at room temperature. Reaction mixture was diluted with ethyl acetate and sequentially washed with aqueous sodium bicarbonate, brine and water, and dried over MgSO$_4$. The solvent was filtered and evaporated under reduced pressure to afford a crude solid, which was purified by column chromatography on silica gel (n-Hexane:EtoAC=1:9~4:6) to give 3-[2-(4-adamantan-1-yl-phenoxy)-acetylamino]-N-naphtalene-2-yl-benzamide as a colorless crystals (16 mg, 61.53% yield).

$^1$HNMR (DMSO-d$_6$, 300 MHz) 10.39 (1H, s, OCH$_2$CONH), 10.27 (1H, s, PhCONHPh), 8.16 (1H, s, aromatic), 7.89 (1H, d, J=8.7 Hz, aromatic), 7.80 (2H, d, J=9.0 Hz, aromatic), 7.66 (1H, d, J=7.8 Hz, aromatic), 7.45 (3H, m, aromatic), 7.28 (2H, d, J=8.4 Hz, aromatic), 6.93 (2H, d, J=8.4 Hz, aromatic), 4.69 (2H, s, OCH$_2$), 2.03 (3H, s, adamantyl), 1.83 (6H, s, adamantyl), 1.71 (6H, s, adamantyl).

EXAMPLE 73

3-[2-(4-adamantan-1-yl-phenoxy)-acetylamino-N-furan-2-ylmethyl-benzamide

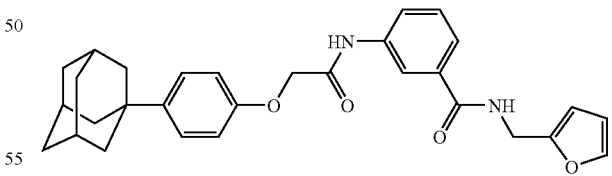

To a solution of 3-[2-(4-adamantan-1-yl-phenoxy)-acetylamino]-benzoic acid (60.0 mg, 0.15 mmol), furfuryl amine (21.9 mg, 0.03 ml, 0.23 mmol), EDC (43.1 mg, 0.23 mmol) and HOBt (34.5 mg, 0.23 mmol) in DMF 1.5 mL was added DIPEA (0.04 ml 0.20 mmol). Reaction mixture was stirred and separated by ethyl acetate and 10% HCl. It was sequentially washed with brine and water, and dried over MgSO$_4$. The solvent was filtered and evaporated under reduced pressure to afford a crude solid, which was purified by silica gel flash column chromatography (n-Hexane:EtoAC:MeOH=6:

3:1) to give 3-[2-(4-adamantan-1-yl-phenoxy)-acetylamino-N-furan-2-ylmethyl-benzamide as a yellow solid (79.5 mg, 100% yield).

¹HNMR (CDCl₃, 300 MHz) 8.47 (3H, m, 2×CONK aromatic), 7.97 (1H, s, aromatic), 7.75 (1H, d, J=8.1 Hz, aromatic), 7.48 (1H, d, J=7.2 Hz, aromatic), 7.33 (3H, m, aromatic), 7.13 (2H, d, J=5.4 Hz aromatic), 6.90 (2H, d, J=9.0 Hz, aromatic), 6.78 (1H, brs, aromatic), 4.55 (2H, s, OCH₂CO), 3.68 (2H, q, J=6.75 Hz, NHCH₂CH₂), 2.91 (2H, t, J=6.9 Hz, NHCH₂CH₂), 2.08 (3H, s, adamantyl), 1.87 (6H, s, adamantyl), 1.75 (6H, m, adamantyl).

EXAMPLE 74

3-[2-(4-adamantan-1-yl-phenoxy)-acetylamino]-N-2-pyridine-yl-ethyl)-benzamide

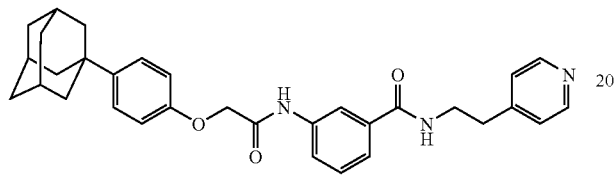

To a solution of 3-[2-(4-adamantan-1-yl-phenoxy)-acetylamino]-benzoic acid (50 mg, 0.123 mmol), 4-(2-aminoethyl)pyridine (22.59 mg, 0.184 mmol) and DIPEA (23.90 mg, 0.184 mmol) in DMF 1 mL was added EDC (35.45 mg, 0.184 mmol) and HOBt (24.99 mg, 0.184 mmol) at room temperature and continued stirring for 16 h at room temperature. Reaction mixture was diluted with ethyl acetate and sequentially washed with aqueous sodium bicarbonate, brine and water, and dried over MgSO₄. The solvent was filtered and evaporated under reduced pressure to afford a crude solid, which was purified by column chromatography on silica gel (n-Hexane:EtoAC=1:5) to give 3-[2-(4-adamantan-1-yl-phenoxy)-acetylamino]-N-(2-pyridine-4-yl-ethyl)benzamide as a colorless crystal (25 mg, 40% yield).

¹HNMR (CDCl₃, 300 MHz) 8.47 (3H, m, 2×CONH, aromatic), 7.97 (1H, s, aromatic), 7.75 (1H, d, J=8.1 Hz, aromatic), 7.48 (1H, d, J=7.2 Hz, aromatic), 7.33 (3H, m, aromatic), 7.13 (2H, d, J=5.4 k, aromatic), 6.90 (2H, d, J=9.0 Hz, aromatic), 6.78 (1H, brs, aromatic), 4.55 (2H, s, OCH₂CO), 3.68 (2H, q, J=6.75 Hz, NHCH₂CH₂), 2.91 (2H, t, J=6.9 Hz, NHCH₂CH₂), 2.08 (3H, s, adamantyl), 1.87 (6H, s, adamantyl), 1.75 (6H, m, adamantyl).

EXAMPLE 75

3-[2-(2,4-dichloro-phenoxy)-acetylamino]-N,N-dimethyl-benzamide

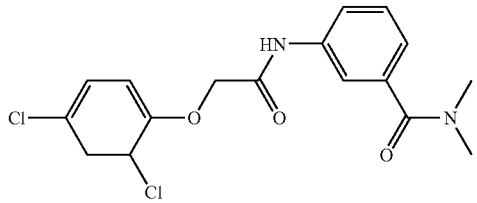 [SMILES: CN(C)C(=O)c1cccc(NC(=O)COC2=CC=C(Cl)CC2Cl)c1]

To solution of 3-[2-(2,4-dichloro-phenoxy)-acetylamino]-benzoic acid (100 mg, 0.29 mmol), dimethylamine (0.031 ml, 0.59 mmol) in DMF 3.0 mL was added EDC (83.4 mg, 0.44 mmol), HOBt (58.9 mg, 0.44 mmol) and DIPEA (0.076 ml, 0.44 mmol). Reaction mixture was stirred at room temperature, and separated by EtoAC and brine. The organic phase was dried (MgSO₄ anh) and concentrated. The residue was purified by silica gel column chromatography (CH₂Cl₂:MeOH=30:1) to give 3-[2-(2,4-dichloro-phenoxy)acetylamino]-N,N-dimethyl-benzamide as a white solid (59.3 mg, 56% yield).

¹H-NMR (CD₃OD, 300 Hz) 7.74 (1H, ps t, J=1.8 Hz, aromatic), 7.64 (1H, m, aromatic), 7.45 (2H, m, aromatic), 7.28 (1H, dd, J=9.0&2.4, aromatic), 7.18 (1H, m, aromatic), 7.09 (1H, d, J=9.3 Hz, aromatic), 4.77 (2H, s, OCH₂CO), 3.09 (3H, s, NCH₃), 3.00 (3H, s, NCH₃).

EXAMPLE 76

3-[2-(2,4-dichloro-phenoxy)-acetylamino]-N-ethyl-benzamide

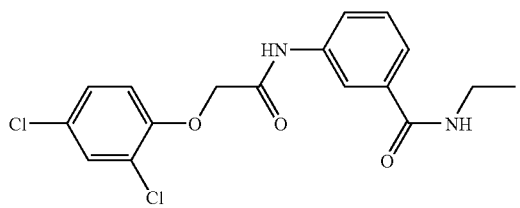 [SMILES: CCNC(=O)c1cccc(NC(=O)COc2ccc(Cl)cc2Cl)c1]

To solution of 3-[2-(2,4-dichloro-phenoxy)-acetylamino]-benzoic acid (150 mg, 0.44 mmol), ethylamine (0.034 ml, 0.66 mmol) in DMF 3.0 mL was added EDC (126.5 mg, 0.66 mmol), HOBt (89.2 mg, 0.66 mmol) and DIPEA (0.11 ml, 0.66 mmol). Reaction mixture was stirred at room temperature, and separated by EtoAC and brine. The organic phase was dried (MgSO₄ anh) and concentrated. The residue was purified by silica gel column chromatography (CH₂Cl₂:MeOH=15:1) to give 3-[2-(2,4-chloro-phenoxy)-acetylamino]-N-ethyl-benzamide as a white solid (144.6 mg, 90% yield).

¹H-NMR (DMSO-d₆, 300 Hz) 10.31 (1H, s, NH), 8.45 (1H, ps t J=5.7 Hz, aromatic), 8.04 (1H, s, aromatic), 7.74 (1H, m, aromatic), 7.55 (2H, m, aromatic), 7.39 (2H, m, aromatic), 7.12 (1H, d, J=9.0 Hz, aromatic), 4.88 (2H, s, OCH₂CO), 3.27 (2H, m, NHCH₂CH₃), 1.10 (3H, t J=7.2 Hz, NHCH₂CH₃).

EXAMPLE 77

3-[2-(2,4-dichloro-phenoxy)-acetylamino]-N-furan-2-ylmethyl-benzamide

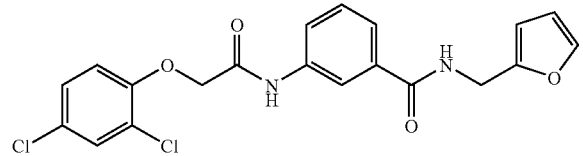 [SMILES: O=C(COc1ccc(Cl)cc1Cl)Nc1cccc(C(=O)NCc2ccco2)c1]

To solution of 3-[2-(2,4-dichloro-phenoxy)-acetylamino]-benzoic acid (100.3 mg, 0.3 mmol), furfuryl amine (58.3 mg, 0.06 ml, 0.6 mmol), 4-dimethylaminopyridine (73.4 mg, 0.6 mmol) and PyBOP (312.3 mg, 1.0-mmol) in DMF 5.0 mL was stirred. Reaction mixture was separated by EtoAC and brine. The organic phase was dried (MgSO₄ anh) and concentrated. The residue was purified by silica gel column chromatography (CH₂Cl₂:MeOH=10:1) to give 3-[2-(2,4-dichloro-phenoxy)-acetylamino]-N-furan-2-ylmethyl-benzamide as a white solid (144.6 mg, 90% yield).

¹H-NMR (DMSO-d₆, 300 Hz) 10.34 (1H, s, NH), 8.97 (1H t, J=5.4 Hz, NH—CH₂), 8.05 (1H, s, aromatic-H), 7.73-7.76

(1H, m, aromatic-H), 7.55-7.59 (3H, m, aromatic-H), 7.34-7.43 (2H, m, aromatic-H), 7.10 (1H, d, J=9.3 Hz, aromatic-H), 6.37-6.39 (1H, m, aromatic-H), 6.26 (1H, d, J=3.0 Hz, aromatic-H), 4.86 (2H, s, O—CH$_2$—CO), 4.86 (2H, d, J=5.7 Hz, NH—CH$_2$-furan).

EXAMPLE 78

3-[2-(2,4-dichloro-phenoxy)-acetylamino]-N-fan-2-ylmethyl-4-hydroxy-benzamide

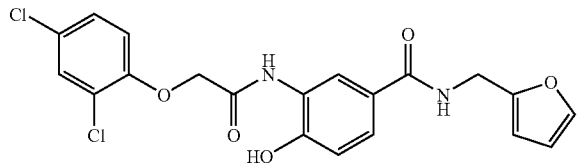 [SMILES: O=C(COc1ccc(Cl)cc1Cl)Nc1cc(C(=O)NCc2ccco2)ccc1O]

furfuryl amine (28.2 mg, 0.29 mmol, 0.03 ml) in anhydrous toluene 3 ml was treated with trimethyl aluminium (in 2.0 M Hexane, 0.64 ml. 1.28 mmol) under nitrogen. After 0.25 h, It was added 2-(2,4-dichloro-phenoxymethyl)-benzoxazole-5-carboxylic acid methyl ester (100.2 mg, 0.29 mmol) in toluene 9 ml. The mixture was stirred for 1 h at 80° C. After cooling, the reaction mixture was treated with diluted HCl until no foaming more. The reaction mixture was separated with ethyl acetate and sodium bicarbonate. The organic phase was washed by brine, dried (MgSO$_4$ anh), and concentrated. The residue was purified by preparative TLC(CH$_2$Cl$_2$: MeOH=15:1) to give 3-[2-(2,4-dichloro-phenoxy)-acetylamino]-N-furan-2-ylmethyl-4- a yellow solid (10.4 mg, 23.2% yield).

$^1$H-NMR (CD$_3$OD, 300 Hz) 8.64 (1H, m, aromatic-H), 7.49-7.54 (2H, m, aromatic-H), 7.41 (1H, m, aromatic-H), 7.30-7.33 (1H, m, aromatic-H), 7.14 (1H, d, J=9.3 Hz, aromatic-H), 6.91 (1H, d, J=8.7 Hz, aromatic-H), 6.33-6.35 (1H, m, aromatic-H), 6.27-6.28 (1H, m, aromatic-H), 5.77 (2H, s, CH$_2$), 4.53 (2H, s, CH$_2$).

EXAMPLE 79

N-benzyl-3-[2-(2,4-dichloro-phenoxy)-acetylamino]-benzamide

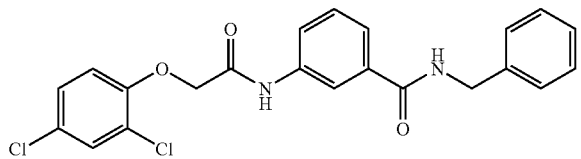 [SMILES: O=C(COc1ccc(Cl)cc1Cl)Nc1cccc(C(=O)NCc2ccccc2)c1]

To solution of 3-[2-(2,4-dichloro-phenoxy)-acetylamino]-benzoic acid (68 mg, 0.2 mmol), benzylamine (0.032 ml, 0.3 mmol) in DMF 3.0 mL was added EDC (57.5 mg, 0.3 mmol), HOBt (40.6 mg, 0.3 mmol) and DIPEA (0.052 ml, 0.3 mmol). Reaction mixture was stirred at room temperature, and separated by EtoAC and brine. The organic phase was dried (MgSO$_4$ anh) and concentrated. The residue was purified by silica gel column chromatography (n-Hexane:EtoAC: MeOH=15:3:1) to give N-benzyl-3-[2-(2,4-dichloro-phenoxy)-acetylamino]-benzamide as a white solid (12 mg, 14% yield).

$^1$H-NMR (CD$_3$OD, 300 Hz) 7.99 (1H, ps t, J=1.8 Hz, aromatic), 8.08 (1H, dd, J=7.5&1.2 Hz, aromatic), 7.61 (2H, m, aromatic), 7.19-7.44 (7H, m, aromatic), 7.01 (1H, d, J=1.8 Hz, aromatic), 4.56 (2H, s, OCH$_2$CO), 3.34 (2H, s, NHCH$_2$Ph).

EXAMPLE 80

3-[2-(2,4-dichloro-phenoxy)-acetylamino]-N-pyridine-4-ylmethyl-benzamide

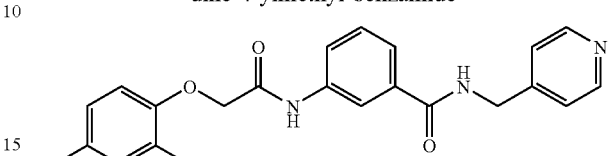

To solution of 3-[2-(2,4-dichloro-phenoxy)-acetylamino]-benzoic acid (68 mg, 0.2 mmol), 4-aminomethyl pyridine (0.024 ml, 0.24 mmol) in DMF 3.0 mL was added EDC (57.5 mg, 0.3 mmol), HOBt (40.6 mg, 0.3 mmol) and DIPEA (0.052 ml, 0.3 mmol). Reaction mixture was stirred at room temperature, and separated by EtoAC and brine. The organic phase was dried (MgSO$_4$ anh) and concentrated. The residue was purified by silica gel column chromatography (CH$_2$Cl$_2$: MeOH=30:1) to give 3-[2-(2,4-dichloro-phenoxy)-acetylamino]-N-pyridine-4-ylmethyl-benzamide as a white solid (60.6 mg, 70% yield).

$^1$H-NMR (DMSO-d$_6$, 300 Hz) 10.35 (1H, s, NH), 9.12 (1H, t, J=5.4 Hz, NH), 8.50 (2H, m, aromatic), 8.11 (1H, m, aromatic), 7.78 (1H, dd, J=8.1 &1.2 Hz aromatic), 7.61 (2H, m, aromatic), 7.44 (1H, ps t, J=7.8 Hz, aromatic), 7.38 (1H, dd, J=8.6&2.4 Hz aromatic), 7.29 (2H, m, aromatic), 7.12 (1H, d, J=9.0 Hz, aromatic), 4.88 (2H, s, OCH$_2$CO), 4.49 (2H, d, J=5.4 Hz, NHCH$_2$).

EXAMPLE 81

3-[2-(2,4-dichloro-phenoxy)-acetylamino]-N-pyridine-3-ylmethyl-benzamide

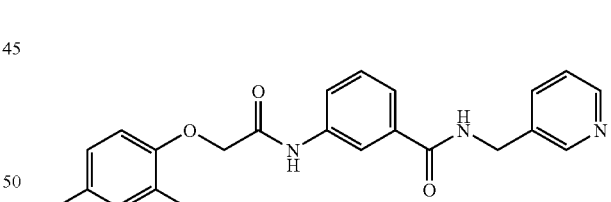

To solution of 3-[2-(2,4-dichloro-phenoxy)-acetylamino]-benzoic acid (102 mg, 0.3 mmol), 3-aminomethyl pyridine (0.036 ml, 0.36 mmol) in DMF 3.0 mL was added EDC (86.3 mg, 0.45 mmol), HOBt (60.8 mg, 0.45 mmol) and DIPEA (0.078 ml, 0.45 mmol). Reaction mixture was stirred at room temperature, and separated by EtoAC and brine. The organic phase was dried (MgSO$_4$ anh) and concentrated. The residue was purified by silica gel column chromatography (CH$_2$Cl$_2$: MeOH=30:1) to give 3-[2-(2,4-dichloro-phenoxy)-acetylamino]-N-pyridine-3-ylmethyl-benzamide as a white-solid (71.4 mg, 55% yield).

$^1$H-NMR (DMSO-d$_6$, 300 Hz) 10.34 (1H, s, NH), 9.09 (1H, t, J=6.0 Hz, NH), 8.54 (1H, d, J=2.1 Hz, aromatic), 8.45 (1H, m, aromatic), 8.09 (1H, s, aromatic), 7.72 (2H, m, aromatic), 7.60 (2H, m, aromatic), 7.33-7.45 (3H, m, aromatic), 7.11 (1H, d, J=9.0 Hz, aromatic), 4.88 (2H, s, OCH$_2$CO), 4.48 (2H, d, J=6.0 Hz, NHCH$_2$).

EXAMPLE 82

3-[2-(2,4-dichloro-phenoxy)-acetylamino]-N-(2-piperidine-1-yl-ethyl)-benzamide

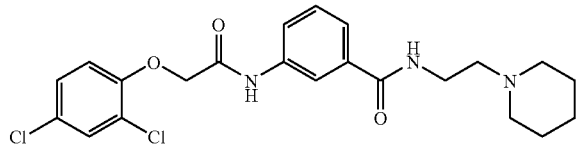 [SMILES: O=C(COc1ccc(Cl)cc1Cl)Nc1cccc(C(=O)NCCN2CCCCC2)c1]

To solution of 3-[2-(2,4-dichloro-phenoxy)acetylamino]-benzoic acid (68 mg, 0.2 mmol), 1-(2-aminoethyl)-piperidine (0.043 ml, 0.3 mmol) in DMF 3.0 mL was added EDC (57.5 mg, 0.3 mmol), HOBt (40.6 mg, 0.3 mmol) and DIPEA (0.052 ml, 0.3 mmol). Reaction mixture was stirred at room temperature, and separated by EtoAC and brine. The organic phase was dried (MgSO$_4$ anh) and concentrated. The residue was purified by silica gel column chromatography (CH$_2$Cl$_2$:MeOH=20:1) to give 3-[2-(2,4-dichloro-phenoxy)-acetylamino]-N-pyridine-3-ylmethyl-benzamide as a white solid (60.6 mg, 70% yield).

$^1$H-NMR (CD$_3$OD, 300 Hz) 8.09 (1H, ps t J=1.8 Hz, aromatic), 7.75 (1H, dd, J=7.8 & 1.2 Hz, aromatic), 7.58 (1H, d, J=7.8 Hz, aromatic), 7.45 (2H, m, aromatic), 7.28 (1H, dd, J=8.7 & 2.4 Hz, aromatic), 7.09 (1H, d, J=8.7 Hz, aromatic), 4.78 (2H, s, OCH$_2$CO), 3.59 (2H, m, aliphatic), 2.73-2.80 (6H, m, aliphatic), 1.65-1.73 (4H, m, aliphatic), 1.55 (2H, m, aliphatic).

EXAMPLE 83

3-[2-(2,4-dichloro-phenoxy)acetylamino]-N-(2-morpholine-4-yl-ethyl)-benzamide

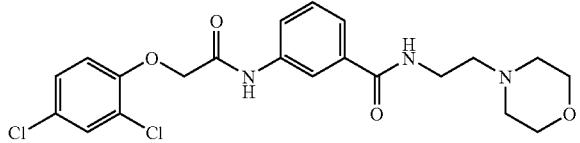 [SMILES: O=C(COc1ccc(Cl)cc1Cl)Nc1cccc(C(=O)NCCN2CCOCC2)c1]

To solution of 3-[2-(2,4-dichloro-phenoxy)-acetylamino]-benzoic acid (68 mg, 0.2 mmol) and 2-morpholine-4-yl-ethylamine (0.039 ml, 0.3 mmol) in DMF 3.0 mL was added EDC (57.5 mg, 0.3 mmol), HOBt (40.6 mg, 0.3 mmol) and DIPEA (0.052 ml, 0.3 mmol). Reaction mixture was stirred at room temperature, and separated by EtoAC and brine. The organic phase was dried (MgSO$_4$ anh) and concentrated. The residue was purified by silica gel column chromatography (CH$_2$Cl$_2$:MeOH=20:1) to give 3-[2-(2,4-dichloro-phenoxy)acetylamino]-N-pyridine-3-ylmethyl-benzamide as a white solid (34.1 mg, 38% yield).

$^1$H-NMR (CD$_3$OD, 300H) 8.02 (1H, m, aromatic), 7.78 (1H, m, aromatic), 7.57 (1H, m, aromatic), 7.41 (2H, m, aromatic), 7.24 (1H, dd, J=9.0 & 2.4 Hz, aromatic), 7.05 (1H, d, J=8.4 Hz, aromatic), 4.74 (2H, s, OCH$_2$CO), 3.70-3.73 (4H, m, aliphatic), 3.54 (2H, t, J=6.6 Hz aliphatic), 2.57-2.66 (6H, m, aliphatic).

EXAMPLE 84

3-[2-(2,4-dichloro-phenoxy)acetylamino]-N-(2-hydroxy-ethyl)-benzamide

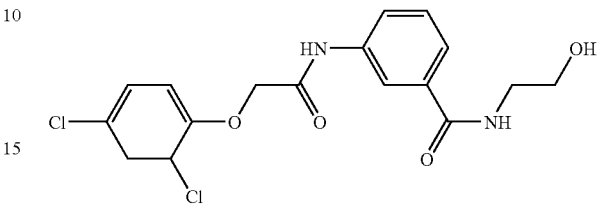

To solution of 3-[2-(2,4-dichloro-phenoxy)acetylamino]-benzoic acid (150 mg, 0.44 mmol) and ethanolamine (0.04 ml, 0.66 mmol) in DMF 3.0 mL was added EDC (126.5 mg, 0.66 mmol), HOBt (89.2 mg, 0.66 mmol) and DIPEA (0.11 ml, 0.66 mmol). Reaction mixture was stirred at room temperature, and separated by EtoAC and brine. The organic phase was dried (MgSO$_4$ anh) and concentrated. The residue was purified by silica gel column chromatography (CH$_2$Cl$_2$:MeOH=15:1) to give 3-[2-(2,4-dichloro-phenoxy)-acetylamino]-N-(2-hydroxy-ethyl)-benzamide as a white solid (135 mg, 80% yield).

$^1$H-NMR (DMSO-d$_6$, 300 Hz) 10.32 (1H, s, NH), 8.40 (1H, ps t J=5.4 Hz NH), 8.05 (1H, s, aromatic), 7.76 (1H, d, J=7.8 Hz aromatic), 7.58 (2H, m, aromatic), 7.39 (2H, m, aromatic), 7.12 (1H, d, J=8.4 Hz aromatic), 4.88 (2H, s, OCH$_2$CO), 4.72 (1H, t, J=6.0 Hz, OH), 3.51 (2H, m, aliphatic), 3.33 (2H, m, aliphatic).

EXAMPLE 85

3-[2-(2,4-dichloro-phenoxy)acetylamino]-N-(3-morpholine-4-yl-propyl)-benzamide

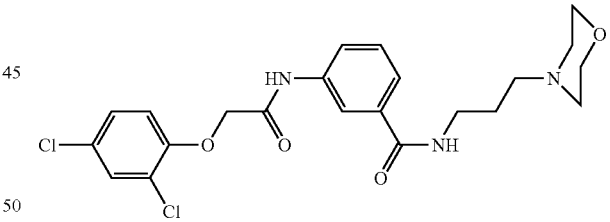

3-[2-(2,4-dichloro-phenoxy)-acetylamino]-benzoic acid (200 mg, 0.59 mmol) and N-(aminopropyl)morpholine (0.17 ml, 1.18 mmol) in DMF 3.0 mL was added EDC (168.7 mg, 0.88 mmol), HOBt (118.9 mg, 0.88 mmol) and DIPEA (0.15 ml, 0.88 mmol). Reaction mixture was stirred at room temperature, and separated by EtoAC and brine. The organic phase was dried (MgSO$_4$ anh) and concentrated. The residue was purified by silica gel column chromatography (CH$_2$Cl$_2$:MeOH=15:1) to give 3-[2-(2,4-dichloro-phenoxy)-acetylamino]-N-(3-morpholine-4-yl-propyl)-benzamide as a yellow solid (56.7 mg, 20% yield).

$^1$H-NMR (CD$_3$OD, 300 Hz) 8.05 (1H, m, aromatic), 7.73 (1H, m, aromatic), 7.54 (1H, m, aromatic), 7.44 (2H, m, aromatic), 7.26 (1H, dd, J=9.0 & 3.0 Hz, aromatic), 7.08 (1H, d, J=8.7 Hz, aromatic), 4.76 (2H, s, OCH$_2$CO), 3.65-3.68

(4H, m, aliphatic), 3.41 (2H, m, aliphatic), 2.41-2.48 (6H, m, aliphatic), 1.81 (2H, m, aliphatic).

EXAMPLE 86

2-[2-(4-adamantan-1-yl-phenoxy)acetylamino]-isonicotinic acid methyl ester

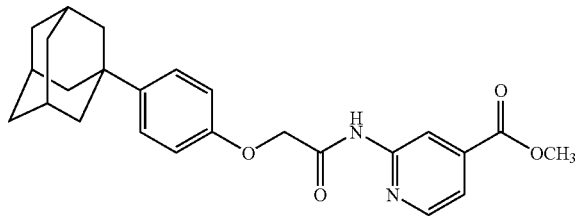 [SMILES: COC(=O)c1ccnc(NC(=O)COc2ccc(C34CC5CC(CC(C5)C3)C4)cc2)c1]

To a solution of appropriate (4-adamantan-1-yl-phenoxy)-acetic acid (150 mg, 0.523 mmol), 2-amino isonicotinic acid methyl ester (159.3 mg, 1.04 mmol) and DMAP (127.9 mg, 1.04 mmol) in DMF (6 ml) was added PyBOP (545 mg, 1.04 mmol) at room temperature and the resulting mixture was stirred until reaction completion as indicated by TLC. Reaction mixture was poured onto ice cold water, diluted with ethyl acetate, separated organic layer and sequentially washed with aqueous sodium bicarbonate, brine and water, and dried over anhydrous MgSO$_4$. The solvent was filtered and evaporated under reduced pressure to afford a crude solid, which was purified by flash chromatography on silica gel (EtOAc:hexanes=1:9 to 1:1) to afford of 2-[2-(4-adamantan-1-yl-phenoxy)acetylamino]-isonicotinic acid methyl ester as a colorless solid (0.166 g, 75% yield).

$^1$H NMR (DMSO-d$_6$, 300 MHz) 9.06 (1H, s, CONH), 8.80 (1H, s, pyridine), 8.45 (1H, d, J=5.1 Hz, pyridine), 7.65 (1H, d, J=5.4 Hz, pyridine), 7.33 (2H, d, J=8.4 Hz, aromatic), 6.95 (2H, d, J=9.3 Hz, aromatic), 4.64 (2H, s, OCH$_2$), 3.97 (3H, s, OCH$_3$), 2.09 (3H, brs, adamantyl), 1.88 (6H, s, adamantyl), 1.76 (6H, m, adamantyl).

EXAMPLE 87

5-[2-(4-adamantan-1-yl-phenoxy)acetylamino]-nicotinic acid methyl ester

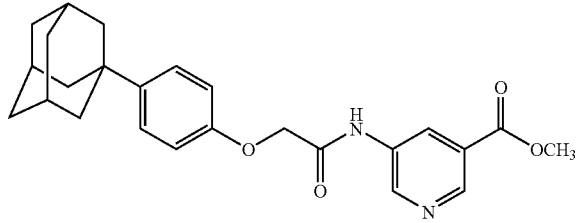 [SMILES: COC(=O)c1cncc(NC(=O)COc2ccc(C34CC5CC(CC(C5)C3)C4)cc2)c1]

To solution of (4-adamantan-1-yl-phenoxy)-acetic acid (125 mg, 0.438 mmol), 5-amino nicotinic acid methyl ester (100 mg, 0.654 mmol) and DIPEA (84.62 mg, 0.654 mmol) in DMF 1 mL was added EDC (125.5 mg, 0.654 mmol), HOBt (88.47 mg, 0.654 mmol). Reaction mixture was stirred at room temperature, poured onto ice cold water, extracted with ethyl acetate, sequentially washed with aqueous sodium bicarbonate, brine and water, dried over anhydrous MgSO$_4$, and concentrated. The residue was purified by flash silica gel column chromatography (EtoAC: Hexane=1:9~1:1) to give 3-[2-(2,4-dichloro-phenoxy)acetylamino]-N-(3-morpholine-4-yl-propyl)-benzamide as a colorless solid (0.125 g, 68% yield).

$^1$HNMR (CDCl$_3$, 300 MHz) 9.01 (2H, brs, CONK pyridine), 8.67 (1H, s, pyridine), 8.53 (1H, s, pyridine), 7.34 (2H, d, J=9.3 Hz, aromatic), 6.95 (2H, d, J=8.7H aromatic), 4.65 (2H, s, OCH$_2$), 3.96 (3H, s, OCH$_3$), 2.09 (3H, brs, adamantyl), 1.89 (6H, d, J=3.0 Hz, adamantyl), 1.76 (6H, m, adamantyl).

EXAMPLE 88

5-[2-(2,4-dichloro-phenoxy)acetylamino]-nicotinic acid methyl ester

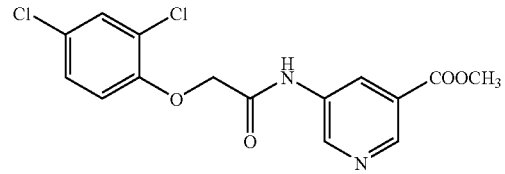 [SMILES: COC(=O)c1cncc(NC(=O)COc2ccc(Cl)cc2Cl)c1]

To solution of (2,4-dichloro-phenoxy)acetic acid (192.7 mg, 0.87 mmol), 5-amino nicotinic acid methyl ester (200 mg, 1.31 mmol) and DIPEA (169.8 mg, 1.31 mmol) in DMF 5 mL was added EDC (252 mg, 1.31 mmol) and HOBt (177.62 mg, 1.31 mmol) at room temperature. Reaction mixture was stirred at room temperature, poured onto ice cold water, extracted with ethyl acetate, sequentially washed with aqueous sodium bicarbonate, brine and water, dried over anhydrous MgSO$_4$, and concentrated. The residue was purified by flash silica gel column chromatography (EtoAC:Hexane=1:9~1:1) to give 3-[2-(2,4-dichloro-phenoxy)-acetylamino]-N-(3-morpholine-4-yl-propyl)-benzamide as a colorless solid (0.185 g, 60% yield).

$^1$H NMR (CDCl$_3$, 300 MHz) 8.98 (2H, d, J=14.7 Hz, CONE pyridine), 8.75 (1H, s, pyridine), 8.65 (1H, s, pyridine), 7.45 (1H, d, J=2.4H, aromatic) 7.26 (1H, dd, J=3.0&7.8 Hz, aromatic), 6.91 (1H, d, J=8.4 Hz, aromatic), 4.68 (2H, s, OCH$_2$), 3.96 (3H, s, OCH$_3$).

EXAMPLE 89

2-(4-adamantan-1-yl-phenoxy)-N-(4-methyl-pyridine-2-yl)acetamide

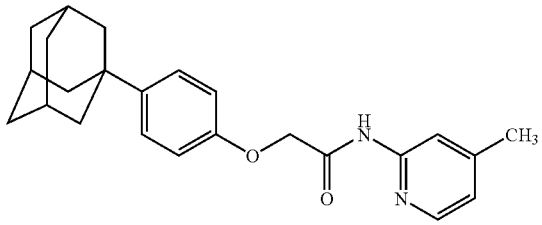 [SMILES: Cc1ccnc(NC(=O)COc2ccc(C34CC5CC(CC(C5)C3)C4)cc2)c1]

To solution of (4-adamantan-1-yl-phenoxy)-acetic acid (50 mg, 0.17 mmol), 5-amino-4-picoline (28.32 mg, 0.26 mmol) and DIPEA (33.85 mg, 0.26 mmol) in DMF 1 mL was added EDC (50.2 mg, 0.26 mmol) and HOBt (35.39 mg, 0.26 mmol) at room temperature. Reaction mixture was stirred at room temperature. Resulting mixture poured onto ice cold water, was extracted with ethyl acetate, sequentially washed with aqueous sodium bicarbonate, brine and water, dried over anhydrous MgSO$_4$, and concentrated under reduced pressure. The residue was purified by flash silica gel column chromatography (EtoAC:Hexane=1:9~2:8) to give 2-(4-adamantan-1-yl-phenoxy)-N-(4-methyl-pyridine-2-yl)-acetamide as a colorless solid (0.033 g, 50% yield).

¹H NMR (CDCl₃, 300 MHz) 8.92 (1H, brs, CONH), 8.16 (1H, d, J=5.4 Hz, aromatic), 8.12 (1H, s, aromatic), 7.31 (2H, m, aromatic), 6.94 (3H, m, pyridine), 4.60 (2H, s, OCH₂), 2.39 (3H, s, CH₃), 2.08 (3H, brs, adamantyl), 1.88 (6H, d, J=3.0 Hz, adamantyl), 1.76 (6H, m, adamantyl).

EXAMPLE 90

2-(2,4-dichloro-phenoxy)-N-(4-methyl-pyridine-2-yl)acetamide

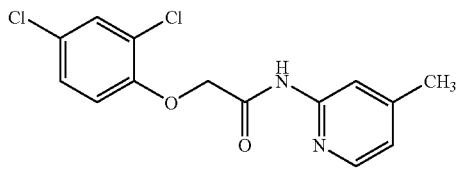 [SMILES: Cc1ccnc(NC(=O)COc2ccc(Cl)cc2Cl)c1]

To solution of (4-adamantan-1-yl-phenoxyacetic acid (50 mg, 0.17 mmol), 5-amino-4-picoline (28.32 mg, 0.26 mmol) and DIPEA (33.85 mg, 0.26 mmol) in DMF 1 mL was added EDC (50.2 mg, 0.26 mmol) and HOBt (35.39 mg, 0.26 mmol) at room temperature. Reaction mixture was stirred at room temperature. Resulting mixture poured onto ice cold water, was diluted by ethyl acetate. The organic phase was separated, sequentially washed with aqueous sodium bicarbonate, brine and water, dried over anhydrous MgSO₄, and concentrated. The residue was purified by flash silica gel column chromatography (EtoAC:Hexane=1:9~4:6) to give 2-(2,4-dichloro-phenoxy)-N-(4-methyl-pyridine-2-yl)-acetamide as a colorless solid (0.247 g, 87.9% yield).

¹H NMR (CDCl₃, 300 MHz) 9.19 (1H, brs, CONH), 8.18 (1H, d, J=4.8 Hz, aromatic), 8.1 (1H, s, aromatic), 7.43 (1H, d, J=3.0 Hz, aromatic), 7.22 (1H, dd, J=2.7, 9.0 Hz, aromatic), 6.94-6.88 (2H, m, aromatic), 4.65 (2H, s, OCH₂), 2.40 (3H, s, CH₃).

EXAMPLE 91

2-[2-(2,4-dichloro-phenoxy)-acetylamino]-isonicotinic acid methyl ester

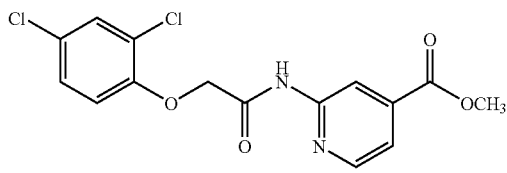 [SMILES: COC(=O)c1ccnc(NC(=O)COc2ccc(Cl)cc2Cl)c1]

To solution of (2,4-dichloro-phenoxyacetic acid (0.200 g, 0.9 mmol), 2-amino isonicotinic acid methyl ester (207 mg, 1.36 mmol) and DMAP (0.222 g, 1.81 mmol) in DMF 13 mL was added PyBOP (946 mg, 1.81 mmol) at room temperature. Reaction mixture was stirred at room temperature. Resulting mixture poured onto ice cold water, was diluted by ethyl acetate. The organic phase was separated, sequentially washed with aqueous sodium bicarbonate, brine and water, dried over anhydrous MgSO₄, and concentrated. The residue was purified by flash silica gel column chromatography (EtoAC:Hexane=1:9-4:6) to give 2-[2-(2,4-dichloro-phenoxy)-acetylamino]-isonicotinic acid methyl ester as a colorless solid (0.229 g, 71% yield).

¹H NMR (DMSO-d₆, 300 MHz) 10.87 (1H, s, CONH), 8.53 (2H, d, J=4.8 Hz, pyridine), 7.58 (m, 2H, aromatic), 7.35 (1H, dd, J=1.8&9.0 Hz, pyridine), 7.11 (1H, d, J=8.4 Hz, aromatic), 4.98 (2H, s, OCH₂), 3.88 (3H, s, OCH₃).

EXAMPLE 92

2-[2-(2,4,5-trichloro-phenoxy)-acetylamino]-isonicotinic acid methyl ester

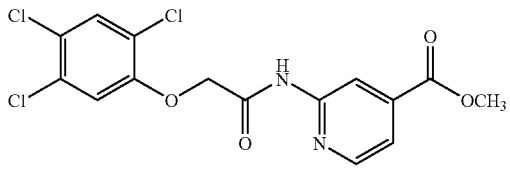 [SMILES: COC(=O)c1ccnc(NC(=O)COc2cc(Cl)c(Cl)cc2Cl)c1]

To solution of (2,4,5-trichloro-phenoxy)-acetic acid (150 mg, 0.59 mmol), 2-amino isonicotinic acid methyl ester (179 mg, 1.18 mmol) and DMAP (144 mg, 1.18 mmol) in DMF 13 mL was added PyBOP (614 mg, 1.18 mmol) at room temperature. Reaction mixture was stared at room temperature. Resulting mixture poured onto ice cold water, was diluted by ethyl acetate. The organic phase was separated, sequentially washed with aqueous sodium bicarbonate, brine and water, dried over anhydrous MgSO₄, and concentrated. The residue was purified by flash silica gel column chromatography (EtoAC:Hexane=1:1) to give 2-[2-(2,4,5-trichloro-phenoxy)-acetylamino]-isonicotinic acid methyl ester as a colorless solid (0.056 g, 24.45% yield).

¹H NMR (DMSO-d₆, 300 MHz) 10.89 (1H, s, CONH), 8.54 (2H, d, J=5.4 Hz, pyridine), 7.85 (s, 1H, aromatic), 7.58 (1H, dd, J=1.35 &4.95 Hz, pyridine), 7.48 (1H, s, aromatic), 5.05 (2H, s, OCH₂), 3.89 (3H, s, OCH₃).

EXAMPLE 93

2-[2-(4-bromo-2-chloro-phenoxy)-acetylamino]-isonicotinic acid methyl ester

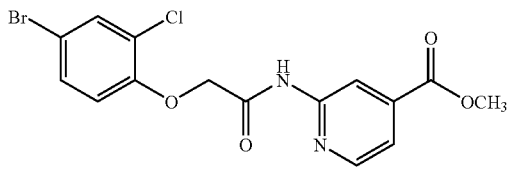

To solution of (4-bromo-2-chloro-phenoxyacetic acid (100 mg, 0.378 mmol), 2-amino isonicotinic acid methyl ester (86.42 mg, 0.568 mmol) and DMAP (69.43 mg, 0.568 mmol) in DMF 2 mL was added PyBOP (295 mg, 0.568 mmol) at room temperature. Reaction mixture was stirred at room temperature. Resulting mixture poured onto ice cold water, was diluted by ethyl acetate. The organic phase was separated, sequentially washed with aqueous sodium bicarbonate, brine and water, dried over anhydrous MgSO₄, and concentrated. The residue was purified by flash silica gel column chromatography (EtoAC:Hexane=1:9~4:6) to give 2-[2-(4-bromo-2-chloro-phenoxy)-acetylamino]-isonicotinic acid methyl ester as a colorless solid (0.084 g, 56% yield).

¹H NMR (CDCl₃, 300 M) 9.2 (1H, s, CONH), 8.77 (1H, s, pyridine), 8.47 (1H, d, J=4.8 Hz, pyridine), 7.66 (1H, dd, J=1.2&4.8H pyridine), 7.59 (1H, d, J=2.4 Hz, aromatic), 7.38

(1H, dd, J=2.25&8.85 Hz, aromatic), 6.85 (1H, d, J=8.4 Hz, aromatic), 4.67 (2H, s, OCH$_2$), 3.96 (3H, s, OCH$_3$).

EXAMPLE 94

2-[2-(4-tert-butyl-phenoxy)-acetylamino]-isonicotinic acid methyl ester

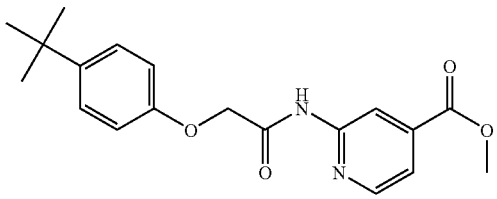 [SMILES: COC(=O)c1ccnc(NC(=O)COc2ccc(C(C)(C)C)cc2)c1]

A solution of (4-tert-butyl-phenoxy)acetic acid (200.1 mg, 0.96 mmol), 2-amino-isonicotinamide (109.5 mg, 0.72 mmol), DIPEA (0.17 ml, 0.96 mmol) and PyBOP (499.5 mg, 0.96 mmol) in DMF 6.0 mL was stirred, then partitioned between ethyl acetate and water. The organic phase was purified by preparative TLC(Hexane:EtoAC:MeOH=15:3:1) to give 2-[2-(4-tert-butyl-phenoxy)-acetylamino]-isonicotinic acid methyl ester as a white solid (124.0 mg, 50.3% yield).

$^1$H-NMR (CDCl$_3$, 300 Hz) 9.20 (1H, s, NH), 8.83 (1H, s, aromatic-H), 8.45 (1H, d, J=5.1 Hz, aromatic-H), 7.66-7.68 (1H, m, aromatic-H), 7.33-7.37 (2H, m, aromatic-E), 6.93-6.97 (2H, m, aromatic-H), 4.64 (2H, s, CH$_2$), 3.97 (3H, s, CH$_3$), 1.31 (9H, s, CH$_3$).

EXAMPLE 95

2-[2-(2,4-dichloro-phenoxy)-acetylamino]-isonicotinic acid

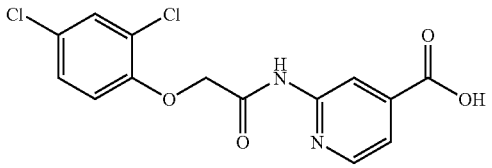 [SMILES: O=C(COc1ccc(Cl)cc1Cl)Nc1cc(C(=O)O)ccn1]

A solution of 2-[2-(2,4-dichloro-phenoxy)-acetylamino]-isonicotinic acid methyl ester (50 mg, 0.14 mmol) and lithium Iodide (189 mg, 1.41 mmol) in pyridine (3 mL) was heated to reflux until reaction completion, then cooled and distilled off the solvent under reduced pressure. The residue was taken up in water, neutralized and extracted with methanol/MC mixture (10%). The combined extracts were washed with brine and water, dried over anhydrous MgSO$_4$, filtered and concentrated under reduced pressure. The resultant crude product was purified by HPLC (MeOH/MC=10%) to afford 2-[2-(2,4-dichloro-phenoxy)acetylamino]-isonicotinic acid as a colorless solid (0.02 g, 41% yield).

$^1$H NMR (DMSO-d$_6$, 300 MHz) 10.55 (1H, s, CONH), 8.44 (1H, s, pyridine), 8.32 (1H, d, J=3.9 Hz pyridine), 7.59 (1H, d, J=2.1 Hz, pyridine), 7.52 (1H, dd, J=0.9&3.75 Hz, aromatic), 7.36 (1H, dd, J=1.95&6.75 Hz, aromatic), 7.12 (1H, d, J=6.6 Hz, aromatic), 4.96 (2H, s, OCH$_2$), COOH not detected.

EXAMPLE 96

5-[2-(4-adamantan-1-yl-phenoxy)-acetylamino]-nicotinic acid

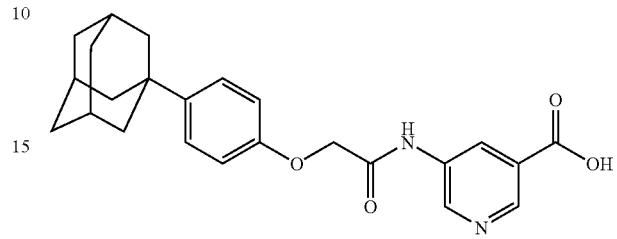

A solution of 5-[2-(4-adamantan-1-yl-phenoxy)acetylamino]-nicotinic acid methyl ester (50 mg, 0.11 mmol) and lithium Iodide (189 mg, 1.11 mmol) in pyridine (3 mL) was heated to reflux until reaction completion, then cooled and distilled off the solvent under reduced pressure. The residue was taken up in water, neutralized and extracted with methanol/MC mixture (10%). The combined extracts were washed with brine and water, dried over anhydrous MgSO$_4$, filtered and concentrated under reduced pressure. The resultant crude product was purified by HPLC (MeOH/MC-10%) to afford 5-[2-(4-adamantan-1-yl-phenoxy)-acetylamino]-nicotinic acid as a colorless solid (0.015 g, 30% yield).

$^1$H NMR (CD$_3$OD+CDCl$_3$, 300 MHz) 8.95 (1H, d, J=1.8 Hz, pyridine), 8.84 (1H, s, pyridine), 8.44 (1H, s, pyridine), 7.28 (2H, d, J=8.4 Hz, aromatic), 6.94 (2H, d, J=9.0H, aromatic), 4.62 (2H, s, OCH$_2$), 2.04 (3H, brs, adamantyl), 1.86 (6H, d, J=3.0 Hz, adamantyl), 1.74 (6H, m, adamantyl), COOH and CONH not detected.

EXAMPLE 97

5-[2-(2,4-dichloro-phenoxy)-acetylamino]-nicotinic acid

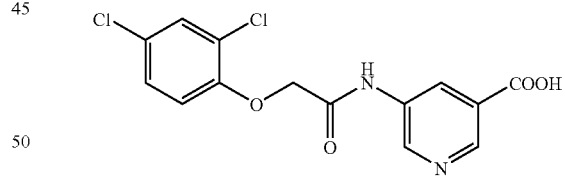

A solution of 5-[2-(2,4-dichloro-phenoxy)-acetylamino]-nicotinic acid methyl ester (50 mg, 0.14 mmol) and lithium Iodide (189 mg, 1.41 mmol) in pyridine (3 mL) was heated to reflux until reaction completion, then cooled and distilled off the solvent under reduced pressure. The residue was taken up in water, neutralized and extracted with methanol/MC mixture (10%). The combined extracts were washed with brine and water, dried over anhydrous MgSO$_4$, filtered and concentrated under reduced pressure. The resultant crude product was purified by HPLC (MeOH/MC=10%) to afford 5-[2-(4-adamantan-1-yl-phenoxy)-acetylamino]-nicotinic acid as a colorless solid (0.022 g, 45% yield).

$^1$H NMR (DMSO-d$_6$, 300 MHz) 10.70 (1H, s, CONH), 8.77 (2H, d, J=15.9 Hz, pyridine), 8.46 (1H, s, pyridine), 7.60

(1H, d, J=2.4 Hz, aromatic), 7.36 (1H, dd, J=2.4&8.4 Hz, aromatic), 7.13 (1H, d, J=9 Hz, aromatic), 4.93 (2H, s, OCH$_2$), COOH not detected.

EXAMPLE 98

2-[2-(4-adamantan-1-yl-phenoxy)acetylamino]-isonicotinic acid

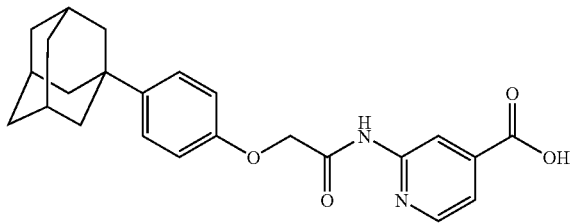 [SMILES: O=C(COc1ccc(C23CC4CC(CC(C4)C2)C3)cc1)Nc1cc(C(=O)O)ccn1]

A solution of 2-[2-(4-adamantan-1-yl-phenoxy)-acetylamino]-isonicotinic acid methyl ester (50 mg, 0.11 mmol) and lithium Iodide (159 mg, 1.11 mmol) in pyridine (3 mL) was heated to reflux until reaction completion, then cooled and distilled off the solvent under reduced pressure. The residue was taken up in water, neutralized and extracted with methanol/MC mixture (10%). The combined extracts were washed with brine and water, dried over anhydrous MgSO$_4$, filtered and concentrated under reduced pressure. The resultant crude product was purified by HPLC (MeOH/MC=100%) to afford 2-[2-(4-adamantan-1-yl-phenoxy)-acetylamino]-isonicotinic acid as a colorless solid (0.039 g, 81% yield).

$^1$H NMR (DMSO-d$_6$, 300 MHz) 10.29 (1H, s, CONH), 8.39 (1H, s, pyridine), 8.26 (1H, d, J=5.1 Hz, pyridine), 7.45 (1H, d, J=5.1 Hz, pyridine), 7.27 (2H, d, J=8.7 Hz, aromatic), 6.90 (2H, d, J=8.4 Hz, aromatic), 4.74 (2H, s, OCH$_2$), 2.03 (3H, brs, adamantyl), 1.82 (6H, d, J=1.8 Hz, adamantyl), 1.71 (6H, s, adamantyl), COOH not detected.

EXAMPLE 99

2-[2-(4-bromo-2-chloro-phenoxy)-acetylamino]-isonicotinic acid

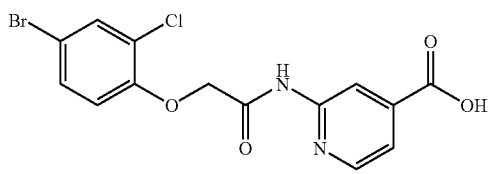

A solution of 2-[2-(4-bromo-2-chloro-phenoxy)-acetylamino]-isonicotinic acid methyl ester (50 mg, 0.125 mmol) and lithium Iodide (189 mg, 1.25 mmol) in pyridine (3 mL) was heated to reflux until reaction completion, then cooled and distilled off the solvent under reduced pressure. The residue was taken up in water, neutralized and extracted with methanol/MC mixture (10%). The combined extracts were washed with brine and water, dried over anhydrous MgSO$_4$, filtered and concentrated under reduced pressure. The resultant crude product was purified by HPLC (MeOH/MC=10%) to afford 2-[2-(4-bromo-2-chloro-phenoxy)-acetylamino]-isonicotinic acid as a colorless solid (0.012 g, 25% yield).

$^1$H NMR (DMSO-d$_6$, 300 MHz) 10.29 (1H, s, CONH), 8.33 (1H, s, pyridine), 8.21 (1H, d, J=5.1 Hz, pyridine), 7.71 (1H, d, J=2.4H, pyridine), 7.49 (1H, dd, J=2.4&8.4H, aromatic), 7.41 (1H, d, J=4.8 Hz, aromatic), 7.06 (1H, d, J=8.7 Hz, aromatic), 4.92 (2H, s, OCH$_2$), COOH not detected

EXAMPLE 100

2-[2-(4-tert-butyl-phenoxy)acetylamino]-isonicotinic acid

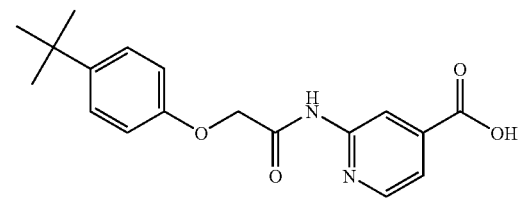 [SMILES: CC(C)(C)c1ccc(OCC(=O)Nc2cc(C(=O)O)ccn2)cc1]

To solution of 2-[2-(4-tert-butyl-phenoxy)-acetylamino]-isonicotinic acid methyl ester (51.8 mg, 0.15 mmol) in pyridine 6 ml was added lithium Iodide (12.6 mg, 0.30 mmol), and stirred at 125° C. Reaction mixture was concentrated, and purified by Prep-TLC(CH$_2$Cl$_2$:MeOH=10:1) to give as a colorless solid (394 mg, 77.94% yield).

$^1$H-NMR (DMSO-d$_6$, 300 Hz) 10.63 (1H, s, NH), 8.53 (1H, s, aromatic-H), 8.45 (1H, d, J=5.1 Hz, aromatic-H), 7.55 (1H, d, J=4.8 Hz, aromatic-H), 7.31 (2H, d, J=8.4 Hz, aromatic-H), 6.88 (2H, d, J=8.7 Hz, aromatic-H), 4.78 (2H, s, CH$_2$), 1.25 (9H, s, CH$_3$).

EXAMPLE 101

5-[2-(4-adamantan-1-yl-phenoxy)-acetylamino]-N-furan-2-ylmethyl-nicotinamide

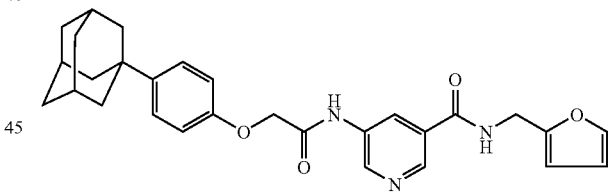

To solution of 5-[2-(4-adamantan-1-yl-phenoxy)-acetylamino]-nicotinic acid (40 mg, 0.098 mmol), furfuryl amine (19.11 mg, 0.196 mmol) and DMAP (24.06 mg, 0.196 mmol) in DMF was added PyBOP (102.4 mg, 0.196 mmol) at room temperature, and stirred. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The resultant crude product was purified by PLC (MeOH:MC=1:9) to afford 5-[2-(4-adamantan-1-yl-phenoxy)-acetylamino]-N-furan-2-ylmethyl-nicotinamide as a colorless solid (5 mg, 25.3% yield).

$^1$H NMR (DMSO-d$_6$, 300 MHz) 10.74 (1H, s, OCH$_2$CONH), 9.25 (1H, t, J=5.85 Hz, CH$_2$CONH), 8.46 (1H, d, J=4.8 Hz, pyridine), 8.41 (1H, s, pyridine), 7.61 (1H, d, J=3.0 Hz, pyridine), 7.58 (1H, s, furan), 7.51-7.49 (1H, m, furan), 7.37 (1H, dd, J=2.4&8.4 Hz, furan), 7.11 (1H, d, J=8.7

Hz, aromatic), 6.39 (1H, t, J=2.4 Hz, aromatic), 6.28 (1H, d, J=3 Hz, aromatic), 4.97 (2H, s, OCH$_2$), 445 (2H, d, J=5.4 Hz, CONHCH$_2$).

EXAMPLE 102

5-[2-(4-adamantan-1-yl-phenoxy)acetylamino]-N-(2-pyridine-4-yl-ethyl)nicotinamide

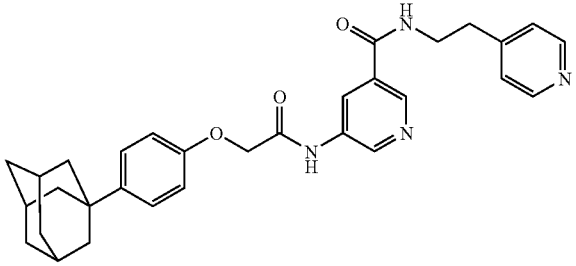 [SMILES: O=C(COc1ccc(C23CC4CC(CC(C4)C2)C3)cc1)Nc1cncc(C(=O)NCCc2ccncc2)c1]

To solution of 5-[2-(4-adamantan-1-yl-phenoxy)-acetylamino]-nicotinic acid (40 mg, 0.098 mmol), 2-pyridine-4-yl-ethylamine (24.06 mg, 0.196 mmol) and DMAP (24.06 mg, 0.196 mmol) in DMF was added PyBOP (102.7 mg, 0.196 mmol) at room temperature, and stirred. Reaction mixture was poured onto ice cold water; diluted by methanol/MC mixture (10%). The organic phase was separated, sequentially washed with aqueous sodium bicarbonate, brine and water, dried over anhydrous MgSO$_4$, and concentrated. The resultant crude product was purified by PLC (MeOH:MC=1:9) to afford 5-[2-(4-adamantan-1-yl-phenoxy)acetylamino]-N-(2-pyridine-4-yl-ethyl)nicotinamide as a colorless solid (30 mg, 60% yield).

$^1$H NMR (DMSO-d$_6$, 300 MHz) 8.83-8.74 (3H, m, 2×CONH, pyridine), 8.44 (3H, m, pyridine), 7.31 (2H, d, J=8.4 Hz, pyridine), 7.22 (3H, m, pyridine, aromatic), 6.90 (2H, d, J=9.0 Hz, aromatic), 4.59 (2H, s, OCH$_2$), 3.73 (2H, q, J=5.85 Hz, CONHCH$_2$CH$_2$), 2.97 (2H, t, J=6.6 Hz, CONHCH$_2$CH$_2$), 2.07 (3H, brs, adamantyl), 1.86 (6H, d, J=1.8 Hz, adamantyl), 1.81-1.69 (6H, m, adamantyl).

EXAMPLE 103

5-[2-(4-adamantan-1-yl-phenoxy)-acetylamino]-N-(3-imidazole-1-yl-propyl)nicotinamide

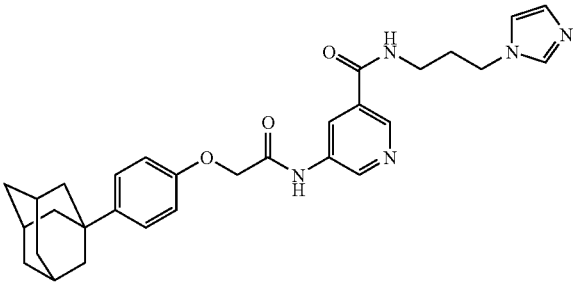 [SMILES: O=C(COc1ccc(C23CC4CC(CC(C4)C2)C3)cc1)Nc1cncc(C(=O)NCCCn2ccnc2)c1]

To solution of 5-[2-(4-adamantan-1-yl-phenoxy)-acetylamino]-nicotinic acid (40 mg, 0.098 mmol), 1-(3-aminopropyl)-imidazole (24.65 mg, 0.196 mmol) and DMAP (24.06 mg, 0.196 mmol) in DMF was added PyBOP (102.47 mg, 0.196 mmol) at room temperature, and stirred. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The resultant crude product was purified by PLC (MeOH:MC=1:9) to afford 5-[2-(4-adamantan-1-yl-phenoxy)-acetylamino]-N-(3-imidazole-1-yl-propyl)nicotinamide as a colorless solid (37 mg, 49% yield).

$^1$H NMR (DMSO-d$_6$, 300 MHz) 10.45 (1H, s, OCH$_2$CONH), 8.92 (1H, d, J=1.8 Hz, pyrazole), 8.72 (2H, d, J=1.8 Hz, pyrazole), 8.47 (1H, t, J=2.1 Hz, CH$_2$CONH), 7.65 (1H, s, pyridine), 7.28 (2H, d, J=9.3 Hz, aromatic), 7.20 (1H, s, pyridine), 6.94 (2H, d, J=9.3 Hz, aromatic), 6.88 (1H, s, pyridine), 4.72 (2H, s, OCH$_2$), 4.02 (2H, t, J=6.75 Hz, NCH$_2$), 3.24 (2H, q, J=6.75 Hz, CH$_2$CH$_2$CH$_2$), 2.03 (3H, brs, adamantyl), 3.24 (2H, t, J=6.75 Hz, CONHCH$_2$CH$_2$), 1.82 (6H, s, adamantyl), 1.71 (6H, m, adamantyl).

EXAMPLE 104

2-[2-(4-adamantan-1-yl-phenoxy)-acetylamino]-N-(4-chloro-phenyl)-isonicotinamide

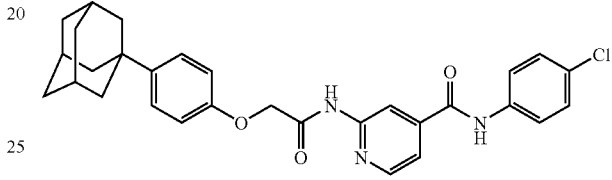

To solution of 2-[2-(4-adamantan-1-yl-phenoxy)-acetylamino]-isonicotinic acid (40 mg, 0.098 mmol), 4-chloroaniline (25.12 mg, 0.196 mmol) and DMAP (21.65 mg, 0.17 mmol) in DMF was added PyBOP (92.22 mg, 0.17 mmol), and stirred. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The resultant crude product was purified by PLC (MeOH:MC=1:9) to afford 2-[2-(4-adamantan-1-yl-phenoxy)-acetylamino]-N-(4-chloro-phenyl)-isonicotinamide as a colorless solid (49 mg, 98% yield).

$^1$H NMR (DMSO-d$_6$, 300 MHz) 10.74 (1H, s, OCH$_2$CONH), 9.25 (1H, t J=5.85 Hz, CH$_2$CONH), 8.46 (1H, d, J=4.8 Hz, pyridine), 8.41 (1H, s, pyridine), 7.61 (1H, d, J=3.0 Hz, pyridine), 7.58 (1H, s, furan), 7.51-7.49 (1H, m, furan), 7.37 (1H, dd, J=24&8.4 Hz, furan), 7.11 (1H, d, J=8.7 Hz, aromatic), 6.39 (1H, t, J=2.4 Hz, aromatic), 6.28 (1H, d, J=3 Hz, aromatic), 4.97 (2H, s, OCH$_2$), 445 (2H, d, J=5.4 Hz, CONHCH$_2$).

EXAMPLE 105

2-[2-(4-adamantan-1-yl-phenoxy)-acetylamino]-N-furan-2-ylmethyl-isonicotinamide

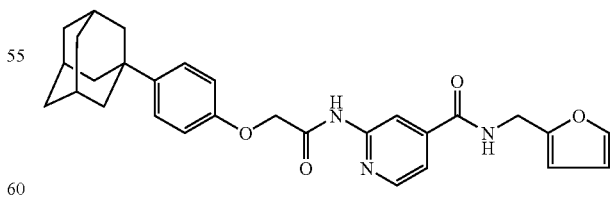

To solution of 2-[2-(4-adamantan-1-yl-phenoxy)-acetylamino]-isonicotinic acid (40 mg, 0.098 mmol), furfuryl amine (19.11 mg, 0.196 mmol) and DMAP (24.06 mg, 0.196 mmol) in DMF was added PyBOP (102.4 mg, 0.196 mmol) at room temperature, and stirred. Reaction mixture was poured onto ice cold water, diluted by methanol/MC mixture (10%).

The organic phase was separated, sequentially washed with aqueous sodium bicarbonate, brine and water, dried over anhydrous MgSO$_4$, and concentrated. The resultant crude product was purified by PLC (MeOH:MC=1:1) to afford 2-[2-(4-adamantan-1-yl-phenoxy)-acetylamino]-N-furan-2-ylmethyl-isonicotinamide as a colorless solid (30 mg, 63% yield).

$^1$H NMR (DMSO-d$_6$, 300 MHz) 10.74 (1H, s, OCH$_2$CONH), 9.25 (1H, t, J=5.85 Hz, CH$_2$CONH), 8.46 (1H, d, J=4.8 Hz, pyridine), 8.4 (1H, s, pyridine), 7.61 (1H, d, J=3.0 Hz, pyridine), 7.58 (1H, s, furan), 7.51-7.49 (1H, m, furan), 7.37 (1H, dd, J=2.4&8.4 Hz, furan), 7.11 (1H, d, J=8.7 Hz, aromatic), 6.39 (1H, t, J=2.4 Hz, aromatic), 6.28 (1H, d, J=3 Hz, aromatic), 4.97 (2H, s, OCH$_2$), 4.45 (2H, d, J=5.4 Hz, CONHCH$_2$)

EXAMPLE 106

2-[2-(4-adamantan-1-yl-phenoxy)-acetylamino]-N-(2-pyridine-4-yl-ethyl)-isonicotinamide

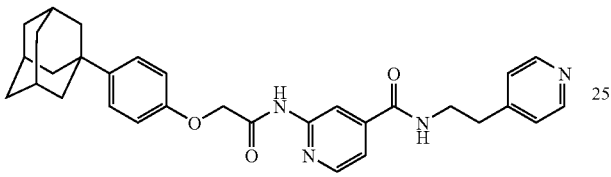

To solution of 2-[2-(4-adamantan-1-yl-phenoxy)-acetylamino]-isonicotinic acid (40 mg, 0.098 mmol), 4-(2-aminoethyl)pyridine (24.06 mg, 0.196 mmol) and DMAP (24.06 mg, 0.196 mmol) in DMF was added PyBOP (102.4 mg, 0.196 mmol) at room temperature, and stirred. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The resultant crude product was purified by PLC (MeOH:MC=1:9) to afford 2-[2-(4-adamantan-1-yl-phenoxy)acetylamino]-N-(2-pyridine-4-yl-ethyl)-isonicotinamide as a colorless solid (42.7 mg, 84% yield).

$^1$H NMR (DMSO-d$_6$, 300 MHz) 10.74 (1H, s, OCH$_2$CONH), 9.25 (1H, t, J=5.85 Hz, CH$_2$CONH), 8.46 (1H, d, J=4.8 Hz, pyridine), 8.4 (1H, s, pyridine), 7.61 (1H, d, J=3.0 Hz, pyridine), 7.58 (1H, s, furan), 7.51-7.49 (1H, m, furan), 7.37 (1H, dd, J=2.4&8.4 Hz, furan), 7.11 (1H, d, J=8.7 Hz, aromatic), 6.39 (1H, t, J=2.4 Hz, aromatic), 6.28 (1H, d, J=3 Hz, aromatic), 4.97 (2H, s, OCH$_2$), 4.45 (2H, d, J=5.4 Hz, CONHCH$_2$).

EXAMPLE 107

2-[2-(4-adamantan-1-yl-phenoxy)-acetylamino]-N-(3-imidazole-1-yl-propyl)-isonicotinamide

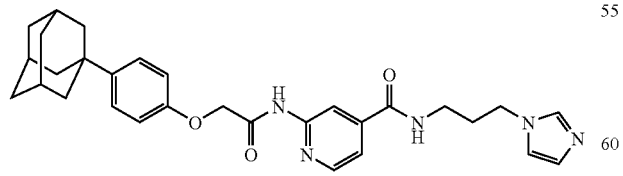

To solution of 2-[2-(4-adamantan-1-yl-phenoxy)-acetylamino]-isonicotinic acid (40 mg, 0.098 mmol), 1-(3-aminopropyl)imidazole (24.65 mg, 0.196 mmol) and DMAP (24.06 mg, 0.196 mmol) in DMF was added PyBOP (102.4 mg, 0.196 mmol) at room temperature, and stirred. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The resultant crude product was purified by PLC (MeOH:MC=1:9) to afford 2-[2-(4-adamantan-1-yl-phenoxy)-acetylamino]-N-(3-imidazole-1-yl-propyl)-isonicotinamide as a colorless solid (44.4 mg, 87.85% yield).

$^1$H NMR (DMSO-d$_6$, 300 MHz) 10.66 (1H, s, pyridine), 8.78 (1H, t, J=5.55 Hz, pyrazole), 8.46 (1H, d, J=4.8H), pyridine), 8.41 (1H, s, pyrazole), 7.83 (1H, brs, OCH$_2$CONH), 7.49-7.46 (1H, m, pyrazole), 7.27 (3H, d, J=9.3 Hz, aromatic, pyridine), 7.0 (1H, brs, CONHCH$_2$), 6.89 (2H, d, J=9.0 Hz, aromatic), 4.78 (2H, s, OCH$_2$), 4.03 (2H, t, J=7.05 Hz, N—CH$_2$), 3.23 (2H, q, J=6.3 Hz, CONHCH$_2$CH$_2$), 2.03 (3H, s, adamantyl), 1.96 (2H, m, CH$_2$CH$_2$CH$_2$), 1.82 (6H, d, J=2.4 Hz, adamantyl), 1.71 (6H, s, adamantyl).

EXAMPLE 108

2-[2-(2,4-dichloro-phenoxy)-acetylamino]-N,N-dimethyl-isonicotinamide

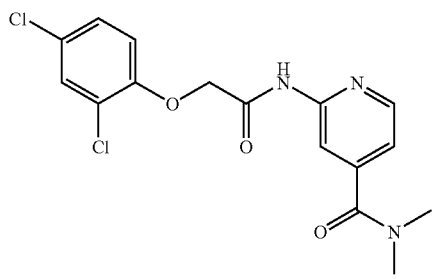 [SMILES: CN(C)C(=O)c1ccnc(NC(=O)COc2ccc(Cl)cc2Cl)c1]

To solution of 2-[2-(2,4-dichloro-phenoxy)-acetylamino]-isonicotinic acid (100.0 mg, 0.31 mmol), dimethylamine (0.24 ml, 0.47 mmol, in 2.0 M tetrahydrofuran), EDC (90.1 mg, 0.47 mmol) and HOBt (63.5 mg, 0.47 mmol) in DMF 4 ml was added DIPEA (60.8 mg, 0.08 ml, 0.47 mmol), and stirred. Reaction mixture was then partitioned between ethyl acetate and 10% HCl. The organic phase was washed with brine, dried over anhydrous MgSO$_4$, and concentrated. The residue was purified by preparative-TLC (n-Hexane:EtoAC:MeOH=6:3:1) to afford 2-[2-(2,4-dichloro-phenoxy)-acetylamino]-N,N-dimethyl-isonicotinamide as a yellow solid (52.9 mg, 46.5% yield).

$^1$HNMR (CDCl$_3$, 300 Hz) 8.46 (1H, s, NH), 8.30-8.42 (2H, m, aromatic-H), 7.45 (1H, d, J=2.4 Hz, aromatic-H), 7.22-7.26 (1H, m, aromatic-H), 7.13 (1H, m, aromatic-H), 6.89 (1H, d, J=9.3 Hz, aromatic-H), 4.66 (2H, s, CH$_2$), 3.12 (3H, s, CH$_3$), 2.97 (3H, s, CH$_3$).

EXAMPLE 109

2-[2-(2,4-dichloro-phenoxy)-acetylamino]-N-furan-2-ylmethyl-isonicotinamide

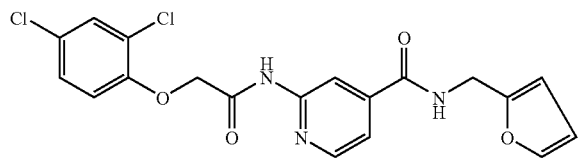 [SMILES: O=C(COc1ccc(Cl)cc1Cl)Nc1cc(C(=O)NCc2ccco2)ccn1]

To solution of 2-[2-(2,4-dichloro-phenoxy)-acetylamino]-isonicotinic acid (16 mg, 0.047 mmol), furfuryl amine (9.1 mg, 0.094 mmol) and DMAP (8.6 mg, 0.07 mmol) in DMF 4 ml was added PyBOP (36 mg, 0.07 mmol) at room temperature, and stirred. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The resultant crude product was purified by PLC (MeOH:MC=1:9) to afford 2-[2-(2,4-dichloro-phenoxy)-acetylamino]-N-furan-2-ylmethyl-isonicotinamide as a colorless solid (5 mg, 25.3% yield).

$^1$H NMR (DMSO-d$_6$, 300 MHz) 10.74 (1H, s, OCH$_2$CONH), 9.25 (1H, t, J=5.85 Hz, CH$_2$CONH), 8.46 (1H, d, J=4.8 Hz, pyridine), 8.41 (1H, s, pyridine), 7.61 (1H, d, J=3.0 Hz, pyridine), 7.58 (1H, s, furan), 7.51-7.49 (1H, m, furan), 7.37 (1H, dd, J=2.4&8.4 Hz, furan), 7.11 (1H, d, J=8.7 Hz, aromatic), 6.39 (1H, t, J=2.4 Hz, aromatic), 6.28 (1H, d, J=3 Hz, aromatic), 4.97 (2H, s, OCH$_2$), 4.45 (2H, d, J=5.4 Hz, CONHCH$_2$).

EXAMPLE 110

2-[2-(2,4-dichloro-phenoxy)-acetylamino]-N-(2-piperidine-1-yl-ethyl)-isonicotinamide

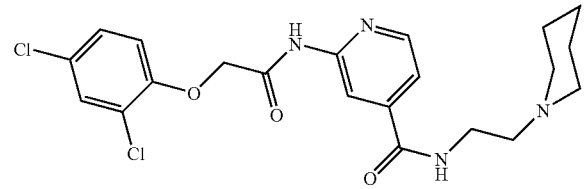 [SMILES: O=C(COc1ccc(Cl)cc1Cl)Nc1cc(C(=O)NCCN2CCCCC2)ccn1]

To solution of 2-[2-(2,4-dichloro-phenoxy)-acetylamino]-isonicotinic acid (80.0 mg, 0.24 mmol), 2-piperidine-1-yl-ethylamine (46.2 mg, 0.05 ml, 0.36 mmol), EDC (69.0 mg, 0.36 mmol) and HOBt (48.7 mg, 0.36 mmol) in DMF 4 ml was added DIPEA (46.5 mg, 0.06 ml, 0.36 mmol), and stirred. Reaction mixture was then partitioned between ethyl acetate and 10% HCl. The organic phase was washed with brine, dried over anhydrous MgSO$_4$, and concentrated. The residue was purified by preparative-TLC (n-Hexane:EtoAC:MeOH=6:3:1) to afford 2-[2-(2,4-dichloro-phenoxy)-acetylamino]-N-(2-piperidine-1-yl-ethyl)-isonicotinamide as a yellow solid (14.3 mg, 13.3% yield).

$^1$HNMR (CDCl$_3$, 300 Hz) 9.10 (1H, s, NH), 8.80 (1H, m, NH), 8.67 (1H, s, aromatic-H), 8.46 (1H, d, J=4.8 Hz, aromatic-H), 7.75 (1H, m, aromatic-H), 7.44-7.46 (1H, nm, aromatic-H), 7.22-7.26 (1H, m, aromatic-H), 6.89 (1H, d, J=9.3 Hz, aromatic-H), 4.66 (2H, s, CH$_2$), 3.82-3.87 (2H, m, CH$_2$), 3.07 (6H, m, CH$_2$), 1.99 (4H, m, CH$_2$), 1.65 (2H, m, CH$_2$), 3.90 (3H, s, CH$_3$).

EXAMPLE 111

2-[2-(2,4-dichloro-phenoxy)-acetylamino]-N-(3-morpholine-4-yl-propyl)-isonicotinamide

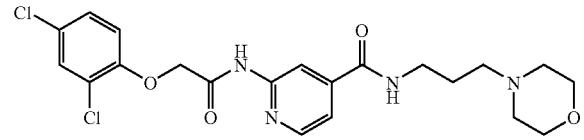 [SMILES: O=C(COc1ccc(Cl)cc1Cl)Nc1cc(C(=O)NCCCN2CCOCC2)ccn1]

To solution of 2-[2-(2,4-dichloro-phenoxy)-acetylamino]-isonicotinic acid (100 mg, 0.31 mmol), 3-morpholine-4-propylamine (67.8 mg, 0.07 ml, 0.47 mmol), EDC (90.1 mg, 0.47 mmol) and HOBt (63.4 mg, 0.47 mmol) in DMF 4 ml was added DIPEA (60.7 mg, 0.08 ml, 0.47 mmol), and stirred. Reaction mixture was then partitioned between ethyl acetate and 10% HCl. The organic phase was washed with brine, dried over anhydrous MgSO$_4$, and concentrated. The residue was purified by preparative-TLC(CH$_2$Cl$_2$:MeOH=6:1) to afford 2-[2-(2,4-dichloro-phenoxy)-acetylamino]-N-(3-morpholine-4-yl-propyl)isonicotinamide as a white solid (31.3 mg, 21.7% yield).

$^1$HNMR (CDCl$_3$, 300 Hz) 9.15 (1H, s, NH), 8.57 (1H, s, aromatic-H), 8.45 (1H, d, J=5.1 Hz, aromatic-H), 8.29 (1H, s, NH), 7.57-7.58 (1H, m, aromatic-H), 7.45 (1H, d, J=2.4 Hz, aromatic-H), 7.23-7.26 (1H, m, aromatic-H), 6.90 (1H, d, J=8.4 Hz, aromatic-H), 4.66 (2H, s, CH$_2$), 3.86 (4H, m, CH$_2$), 3.60-3.65 (2H, m, CH$_2$), 2.79 (6H, m, CH$_2$), 2.00 (2H, m, CH$_2$).

EXAMPLE 112

5-[2-(4-adamantan-1-yl-phenoxy)acetylamino]-nicotinamide

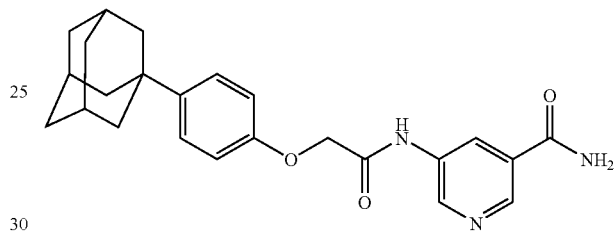

To solution of (4-adamantan-1-yl-phenoxy)-acetic acid (50 mg, 0.17 mmol), 5-amino nicotinamide (47.89 mg, 0.34 mmol) and DMAP (42.71 mg, 0.34 mmol) in DMF 5 ml was added PyBOP (181 mg, 0.34 mmol), and stirred room temperature. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The residue was purified by preparative-TLC(CH$_2$Cl$_2$:MeOH=6:1) to afford 5-[2-(4-adamantan-1-yl-phenoxy)-acetylamino]-nicotinamide as a colorless solid (42.48 mg, 60% yield).

$^1$H NMR (DMSO-d$_6$, 300 MHz) 10.41 (1H, s, CONH), 8.91 (1H, d, J=2.4 Hz, pyridine), 8.75 (1H, d, J=2.4 Hz, pyridine), 8.49-8.47 (1H, m, pyridine), 8.15 (1H, s, CONH$_2$), 7.59 (1H, s, CONH$_2$), 7.29 (2H, d, J=8.7 Hz, aromatic), 6.94 (2H, d, J=2.4 Hz, adamantyl), 1.71 (6H, s, adamantyl).

EXAMPLE 113

2-[2-(4-adamantan-1-yl-phenoxy)acetylamino]-isonicotinamide

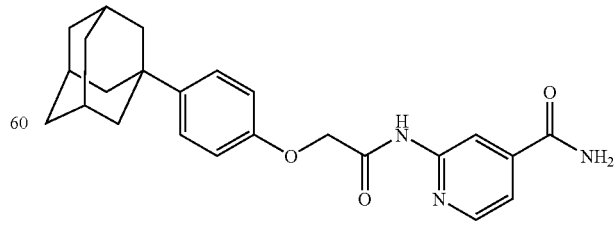

To solution of (4-adamantan-1-yl-phenoxy)acetic acid (70 mg, 0.24 mmol), 2-amino nicotinamide (50.28 mg, 0.36 mmol) and DMAP (59.77 mg, 0.48 mmol) in DMF 5 ml was added PyBOP (452 mg, 0.86 mmol), and stirred room temperature. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The residue was purified by PLC (EtoAC:Hexane:MeOH=3:6:1-2:4:1) to afford 2-[2-(4-adamantan-1-yl-phenoxy)-acetylamino]-isonicotinamide as a colorless solid (0.05 g, 50% yield).

$^1$H NMR (DMSO-d$_6$, 300 MHz) 10.62 (1H, s, CONH), 8.43 (2H, m, CONH$_2$), 8.19 (1H, s, pyridine), 7.67 (1H, s, pyridine), 7.49 (1H, d, J=5.1 Hz, pyridine), 7.26 (2H, d, J=9.3, aromatic), 6.89 (2H, d, J=8.4 Hz, aromatic), 4.78 (2H, s, OCH$_2$), 2.03 (3H, brs, adamantyl), 1.82 (6H, s, adamantyl), 1.71 (6H, s, adamantyl).

EXAMPLE 114

2-[2-(4-fluoro-phenoxy)-acetylamino]-isonicotinamide

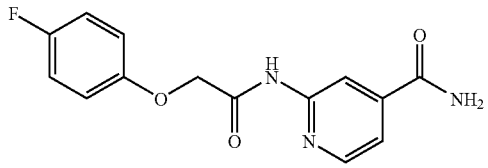 [SMILES: NC(=O)c1ccnc(NC(=O)COc2ccc(F)cc2)c1]

To solution of (4-fluoro-phenoxy)-acetic acid (100 mg, 0.43 mmol), 2-amino nicotinamide (89.39 mg, 0.65 mmol) and DMAP (106 mg, 0.86 mmol) in DMF 5 ml was added PyBOP (452 mg, 0.86 mmol), and stirred room temperature. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The residue was purified by PLC (EtoAC:Hexaane:MeOH=3:6:1-2:4:1) to afford 2-[2-(4-fluoro-phenoxy)-acetylamino]-isonicotinamide as a colorless solid (0.08 g, 59% yield).

$^1$H NMR (DMSO-d$_6$, 300 MHz) 10.67 (1H, s, CONH), 8.44 (1H, d, J=5.1 Hz, CONH$_2$), 8.41 (1H, s, CONH$_2$), 8.20 (1H, brs, pyridine), 7.68 (1H, brs, pyridine), 7.49 (1H, d, J=1.5 &5.1 Hz: pyridine), 7.16-7.11 (2H, m, aromatic), 7.01-6.97 (2H, m, aromatic), 4.80 (2H, s, OCH$_2$).

EXAMPLE 115

2-[2-(2,4-dichloro-phenoxy)acetylamino]-isonicotinamide

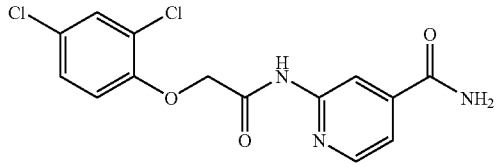 [SMILES: NC(=O)c1ccnc(NC(=O)COc2ccc(Cl)cc2Cl)c1]

To solution of (2,4-dichloro-phenoxy)-acetic acid (51 mg, 0.23 mmol), 2-amino isonicotinamide (47.66 mg, 0.34 mmol) and DMAP (56.6 mg, 0.46 mmol) in DMF 4 ml was added PyBOP (236 mg, 0.46 mmol), and stirred room temperature. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The residue was purified by PLC (EtoAC:Hexane:MeOH=3:6:1-2:4:1) to afford 2-[2-(2,4-dichloro-phenoxy)-acetylamino]-isonicotinamide as a colorless solid (0.06 g, 77% yield).

$^1$H NMR (DMSO-d$_6$, 300 MHz) 10.70 (1H, s, CONH), 8.45-8.41 (2H, m, CONH$_2$), 8.19 (1H, brs, pyridine), 7.67 (1H, brs, pyridine), 7.61 (1H, d, J=24 Hz, pyridine), 7.50 (1H, d, J=5.1 Hz, aromatic), 7.37 (1H, dd, J=2.85&8.85 Hz, aromatic), 7.11 (1H, d, J=8.4 Hz, aromatic), 4.97 (2H, s, OCH$_2$).

EXAMPLE 116

2-[2-(2,4,5-trichloro-phenoxy)-acetylamino]-isonicotinamide

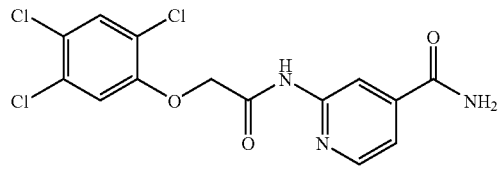 [SMILES: NC(=O)c1ccnc(NC(=O)COc2cc(Cl)c(Cl)cc2Cl)c1]

To solution of (2,4,5-trichloro-phenoxyacetic acid (100 mg, 0.39 mmol), 2-amino isonicotinamide (107 mg, 0.78 mmol) and DMAP (96.22 mg, 0.78 mmol) in DMF 12 ml was added PyBOP (409.7 mg, 0.78 mmol), and stirred room temperature. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The residue was purified by PLC (EtoAC:Hexane:MeOH=3:6:1-2:4:1) to afford 2-[2-(2,4,5-trichloro-phenoxy)-acetylamino]-isonicotinamide as a colorless solid (0.06 g, 41% yield).

$^1$H NMR (DMSO-d$_6$, 300 MHz) 10.72 (1H, s, CONH), 8.45 (1H, d, J=4.8 Hz, CONH$_2$), 8.40 (1H, s, CONH$_2$), 8.20 (1H, brs, pyridine), 7.85 (1H, s, pyridine), 7.68 (1H, brs, pyridine), 7.51-7.48 (2H, m, aromatic), 5.04 (2H, s, OCH$_2$).

EXAMPLE 117

2-[2-(4-bromo-phenoxy)-acetylamino]-isonicotinamide

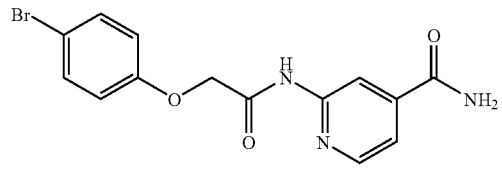 [SMILES: NC(=O)c1ccnc(NC(=O)COc2ccc(Br)cc2)c1]

To solution of (4-bromo-phenoxy)-acetic acid (100 mg, 0.43 mmol), 2-amino isonicotinamide (89.39 mg, 0.65 mmol) and DMAP (106 mg, 0.86 mmol) in DMF 5 ml was added PyBOP (452 mg, 0.86 mmol), and stirred room temperature. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The residue was purified by PLC (EtoAC:Hexane:MeOH=3:6:1~2:4:1) to afford 2-[2-(4-bromo-phenoxy)-acetylamino]-isonicotinamide as a colorless solid (0.083 g, 55% yield).

$^1$H NMR (DMSO-d$_6$, 300 MHz) 10.72 (1H, s, CONH), 8.44 (1H, d, J=3.0 Hz, CONH$_2$), 8.40 (1H, s, CONH$_2$), 8.19

(1H, brs, pyridine), 7.67 (1H, brs, pyridine), 7.50-7.44 (3H, m, pyridine, aromatic), 6.97-6.92 (2H, m, aromatic), 4.83 (2H, s, OCH$_2$).

EXAMPLE 118

2-[2-(4-bromo-2-chloro-phenoxy)-acetylamino]-isonicotinamide

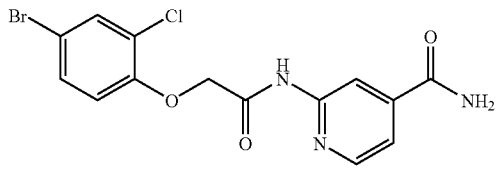

To solution of (4-bromo-2-chloro-phenoxy)-acetic acid (100 mg, 0.37 mmol), 2-amino isonicotinamide (77.89 mg, 0.56 mmol) and DMAP (92.58 mg, 0.75 mmol) in DMF 5 ml was added PyBOP (394.3 mg, 0.75 mmol), and stirred room temperature. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The residue was purified by PLC (EtoAC:Hexane:MeOH=3:6:1~2:4:1) to afford 2-[2-(4-bromo-phenoxy)-acetylamino]-isonicotinamide as a colorless solid (0.076 g, 52% yield).

$^1$H NMR (DMSO-d$_6$, 300 MHz) 10.71 (1H, s, CONH), 8.43 (2H, m, CONH$_2$), 8.19 (1H, s, pyridine), 7.69 (2H, m, pyridine), 7.49 (2H, m, aromatic), 7.06 (1H, d, J=9 Hz, aromatic), 4.97 (2H, s, OCH$_2$).

EXAMPLE 119

2-[2-(4-tert-butyl-phenoxy)-acetylamino]-isonicotinamide

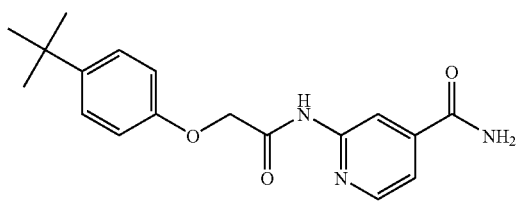 [SMILES: CC(C)(C)c1ccc(OCC(=O)Nc2cc(C(N)=O)ccn2)cc1]

A solution of 4-tert-butylphenoxy acetic acid (60.1 mg, 0.29 mmol), 2-amino isonicotinamide (60.3 mg, 0.44 mmol), DIPEA (0.1 ml, 0.58 mmol) and PyBOP (301.8 mg, 0.58 mmol) in DMF 4.0 mL was stirred, then partitioned between ethyl acetate and water. The organic phase was washed with brine, dried over anhydrous MgSO$_4$, and concentrated. The residue was purified by Prep-TLC (n-Hexane:EtoAc:MeOH=6:3:1) to give 2-[2-(4-tert-butyl-phenoxy)-acetylamino]-isonicotinamide as a white solid (53.6 mg, 56.5% yield).

$^1$H-NMR (DMSO-d$_6$, 300 Hz) 10.64 (1H, s, NH), 8.42-8.46 (2H, m, aromatic-H), 8.20 (1H, s, NH$_2$), 7.68 (1H, s, NH$_2$), 7.49-7.51 (1H, m, aromatic-H), 7.28-7.32 (2H, m, aromatic-H), 6.86-6.91 (2H, m, aromatic-H), 4.78 (2H, s, CH$_2$), 1.24 (9H, s, CH$_3$).

EXAMPLE 120

2-(2-p-tolyloxy-acetylamino)isonicotinamide

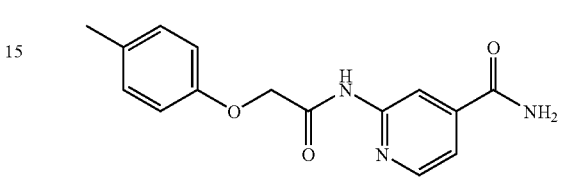

A solution of 4 p-tolyloxy-acetic acid (60.1 mg, 0.36 mmol), 2-amino-isonicotinamide (74.1 mg, 0.54 mmol), DIPEA (0.12 ml, 0.72 mmol) and PyBOP (374.4 mg, 0.72 mmol) in DMF 5.0 mL was stirred, then partitioned between ethyl acetate and water. The organic phase was washed with brine, dried over anhydrous MgSO$_4$, and concentrated. The residue was purified by Prep-TLC(CH$_2$Cl$_2$:MeOH=10:1) to give 2-(2-p-tolyloxy-acetylamino)-isonicotinamide as a white solid (68.5 mg, 66.8% yield).

$^1$H-NMR (DMSO-d$_6$, 300 Hz) 10.61 (1H, s, NH), 8.42-8.45 (2H, m, aromatic-H), 8.20 (1H, s, NH$_2$), 7.68 (1H, s, NH$_2$), 7.49-7.51 (1H, m, aromatic-H), 7.10 (2H, d, J=8.7 Hz, aromatic-H), 6.85-6.88 (2H, m, aromatic-H), 4.76 (2H, s, CH$_2$), 2.23 (3H, s, CH$_3$).

EXAMPLE 121

2-(2-phenoxy-acetylamino)-isonicotinamide

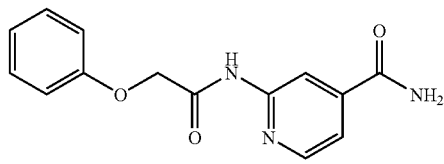 [SMILES: NC(=O)c1ccnc(NC(=O)COc2ccccc2)c1]

To solution of (phenoxy-acetic acid (100 mg, 0.65 mmol), 2-amino isonicotinamide (180 mg, 1.31 mmol) and DMAP (160 mg, 1.31 mmol) in DMF 5 ml was added PyBOP (684 mg, 1.31 mmol), and stirred room temperature. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The residue was purified by PLC (EtOAc:n-Hexanes:MeOH=1:2:1~1:2:2) to afford 242-phenoxy-acetylamino)-isonicotinamide as a colorless solid (0.105 g, 58.9% yield).

$^1$H NMR (DMSO-d$_6$, 300 MHz) 10.65 (1H, s, CONH), 8.45-8.42 (2H, m, CONH$_2$), 8.19 (1H, s, pyridine-H), 7.67

(1H, s, pyridine-H), 7.49 (1H, dd, J=1.5&5.1 Hz, pyridine-H), 7.33-7.28 (2H, m, aromatic), 6.98-6.94 (3H, m, aromatic), 4.81 (2H, s, OCH$_2$).

EXAMPLE 122

2-[2-(4-nitro-phenoxy)-acetylamino]-isonicotinamide

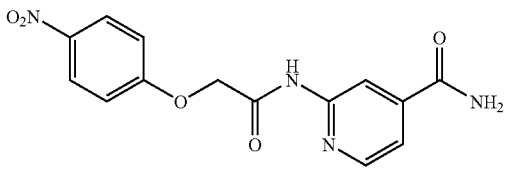 [SMILES: NC(=O)c1ccnc(NC(=O)COc2ccc([N+](=O)[O-])cc2)c1]

To solution of (4-nitro-phenoxy)-acetic acid (50 mg, 0.25 mmol), 2-amino isonicotinamide (52 mg, 0.37 mmol) and DMAP (62 mg, 0.5 mmol) in DMF 6 ml was added PyBOP (684 mg, 1.31 mmol), and stirred room temperature. Reaction mixture was poured onto ice cold water, diluted by methanol/MC mixture (10%). The organic phase was separated, sequentially washed with aqueous sodium bicarbonate, brine and water, dried over anhydrous MgSO$_4$, and concentrated. The residue was purified by PLC (EtOAc:n-Hexane:MeOH=1:2:1~1:2:2) to afford 2-[2-(4-nitro-phenoxy)-acetylamino]-isonicotinamide as a colorless solid (0.04 g, 50% yield).

$^1$HNMR (DMSO-d$_6$, 300 MHz) 10.87 (1H, s, CONH), 8.46 (1H, d, J=5.4 Hz, CONH$_2$), 8.24-8.19 (3H, m, CONH$_2$, pyridine-H), 7.67 (1H, s, pyridine), 7.50 (1H, J=5.7 Hz, pyridine), 7.19 (2H, d, J=9.0 Hz, aromatic), 5.02 (2H, s, OCH$_2$).

EXAMPLE 123

2-(2,4-dichloro-phenoxymethyl)-benzoxazole-5-carboxylic acid methyl ester

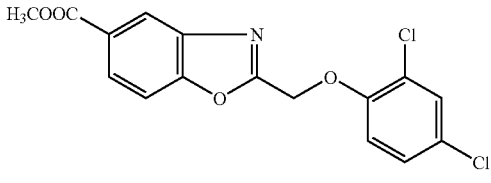

A mixture of 3-amino-4-hydroxy-benzoic acid methyl ester (105.7 mg, 0.63 mmol) and 2,4-dichlorophenoxyacetic acid (100 mg, 0.45 mmol) in PPSE (1.5 mL) was heated at 160° C. for 4 h. At the end of the reaction period, the mixture was taken to 3 mL dichloromethane and neutralized with 4.5 mL 1 N NaOH solution. The organic layer was separated and the aqueous solution extracted with 3×3 mL portions of dichloromethane. The combined extracts were dried over anhydrous MgSO$_4$, filtered and the solvent was removed with rotary evaporator under reduced pressure. The residue was purified by flash chromatography (EtOAc:hexanes=1:1) to afford 2-(2,4-dichlorophenoxymethyl)-benzoxazole-5-carboxylic acid methyl ester as a colorless powder (0.115 g, 52% yield).

$^1$H NMR (CDCl$_3$, 300 MHz) 8.45 (1H, d, J=1.2 Hz, aromatic), 8.14 (1H, dd, J=1.5, 9.0 Hz, aromatic), 7.60 (1H, d, J=8.4 Hz, aromatic), 7.40 (1H, d, J=2.7 Hz aromatic), 7.19 (1H, dd, J=2.4, 8.4 aromatic), 7.07 (1H, d, J=9.3 Hz, aromatic), 5.39 (2H, s, OCH$_2$), 3.96 (3H, s, OCH$_3$).

EXAMPLE 124

2-(4-adamantan-1-yl-phenoxymethyl)-benzoxazole-5-carboxylic acid methyl ester

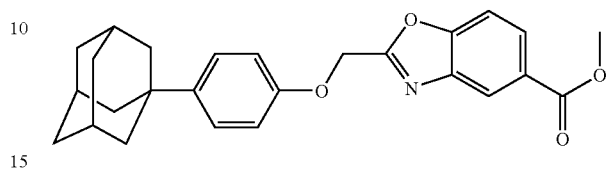

A mixture of (4-adamantan-1-yl-phenoxymethyl)-acetic acid (200.0 mg, 0.70 mmol) and 3-amino-4-hydroxy-benzoic acid methyl ester (164.3 mg, 0.98 mmol) in PPSE (3 mL) was heated at 140° C. for 2 h. At the end of the reaction period, the mixture was taken to dichloromethane and neutralized with 1 N NaOH solution. The organic layer was separated and the aqueous solution extracted with dichloromethane. The combined extracts were dried over anhydrous MgSO$_4$, filtered and the solvent was removed with rotary evaporator under reduced pressure. The residue was purified by flash chromatography (n-Hexane:EtoAc:MeOH=6:3:1) to afford 2-(4-adamantan-1-yl-phenoxymethyl)-benzoxazole-5-carboxylic acid methyl ester as a white solid (187.3 mg, 64.1% yield).

$^1$H-NMR (CDCl$_3$, 300 Hz) 8.45 (1H, m, aromatic-H), 8.11-8.14 (1H, m, aromatic-H), 7.59 (1H, d, J=9.3 Hz, aromatic-H), 7.28-7.33 (2H, m, aromatic-H), 6.99-7.03 (2H, m, aromatic-H), 5.32 (2H, s, CH$_2$), 3.96 (3H, s, CH$_3$), 2.08 (3H, m, adamantly-H), 1.87 (6H, m, adamantly-H), 1.76 (6H, m, adamantly-H).

EXAMPLE 125

2-(4-adamantan-1-yl-phenoxymethyl)-benzoxazole-6-carboxylic acid methyl ester

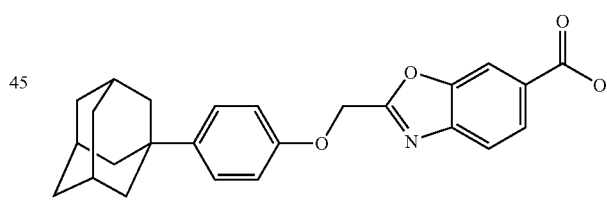

A mixture of (4-adamantan-1-yl-phenoxymethyl)acetic acid (200.0 mg, 0.70 mmol) and 4-amino-3-hydroxy-benzoic acid methyl ester (164.3 mg, 0.98 mmol) in PPSE (3 mL) was heated at 140° C. for 2 h. At the end of the reaction period, the mixture was taken to dichloromethane and neutralized with 1 N NaOH solution. The organic layer was separated and the aqueous solution extracted with dichloromethane. The combined extracts were dried over anhydrous MgSO$_4$, filtered and the solvent was removed with rotary evaporator under reduced pressure. The residue was purified by flash chromatography (n-Hexane:EtoAc:MeOH=6:3:1) to afford 2-(4-adamantan-1-yl-phenoxymethyl)-benzoxazole-6-carboxylic acid methyl ester as a white solid (184.0 mg, 63.0% yield).

$^1$H-NMR (CDCl$_3$, 300 Hz) 8.25 (1H, s, aromatic-H), 8.08-8.11 (1H, m, aromatic-H), 7.79 (1H, d, J=8.4 Hz, aromatic-H), 7.30 (2H, d, J=9.3 Hz, aromatic-H), 7.01 (2H, d, J=9.3 Hz, aromatic-H), 5.33 (2H, s, CH$_2$), 3.96 (3 Hz s, CH$_3$), 2.08 (3H, m, adamantly-H), 1.87 (6H, m, adamantly-H), 1.75 (6H, m, adamantly-H).

EXAMPLE 126

2-(4-adamantan-1-yl-phenoxymethyl)-1H-benzoimidazole-5-carboxylic acid methyl ester

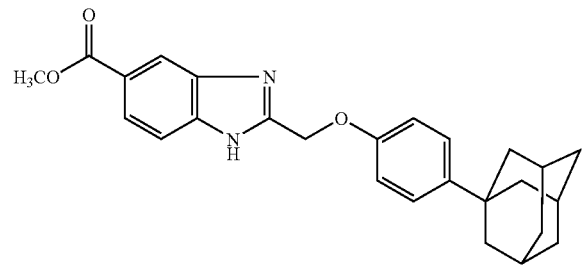 [SMILES: COC(=O)c1ccc2[nH]c(COc3ccc(C45CC6CC(CC(C6)C4)C5)cc3)nc2c1]

A mixture of (4-adamantan-1-yl-phenoxymethyl)-acetic acid (200.0 mg, 0.70 mmol) and 4-amino-3-hydroxy-benzoic acid methyl ester (164.3 mg, 0.98 mmol) in PPSE (2.4 mL) was heated at 140° C. for 4 h. At the end of the reaction period, the mixture was taken to ethyl acetate and neutralized with aqueous sodium bicarbonate. The organic layer was separated and the aqueous solution extracted with ethyl acetate. The combined extracts were dried over anhydrous MgSO$_4$, filtered and the solvent was removed with rotary evaporator under reduced pressure. The residue was purified by flash chromatography (EtOAc:Hexane=1:9~4:6 to afford 2-(4-adamantan-1-yl-phenoxymethyl)-1H-benzoimidazole-5-carboxylic acid methyl ester as a colorless powder (0.282 g, 90% yield).

$^1$HNMR (CDCl$_3$, 300 MHz) 8.35 (1H, s, aromatic), 7.98 (1H, dd, J=1.8&8.7 Hz, aromatic), 7.59 (1H, d, J=8.4 Hz, aromatic), 7.19 (2H, m, aromatic), 6.84 (2H, m, aromatic), 5.34 (2H, s, OCH$_2$), 3.91 (3H, s, OCH$_3$), 2.04 (3H, s, adamantyl), 1.81-1.66 (12H, m, adamantyl), NH not detected.

EXAMPLE 127

2-(2,4-dichloro-phenoxymethyl)-benzoxazole-6-carboxylic acid methyl ester

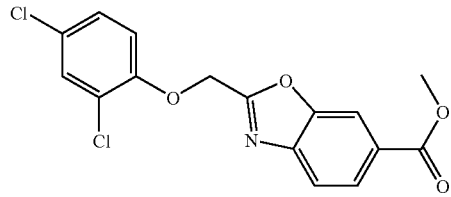 [SMILES: COC(=O)c1ccc2nc(COc3ccc(Cl)cc3Cl)oc2c1]

A mixture of 4-amino-3-hydroxy-benzoic acid methyl ester (210.7 mg, 1.26 mmol) and 2,4-dichlorophenoxy acetic acid (200.0 mg, 0.90 mmol) in PPSE (3 mL) was heated at 140° C. for 2 h. At the end of the reaction period, the mixture was taken to dichloromethane and neutralized with 1 N NaOH solution. The organic layer was separated and the aqueous solution extracted with dichloromethane. The combined extracts were dried over anhydrous MgSO$_4$, filtered and the solvent was removed with rotary evaporator under reduced pressure. The residue was purified by flash chromatography (n-Hexanes:EtoAC:MeOH=6:3:1) to afford 2-(2,4-dichloro-phenoxymethyl)-benzoxazole-6 carboxylic acid methyl ester as a colorless powder (216.7 mg, 68.6% yield).

$^1$H-NMR (CDCl$_3$, 300 Hz) 8.26 (1H, s, aromatic-H), 8.07-8.12 (1H, m, aromatic-H), 7.79 (1H, d, J=8.4 Hz, aromatic-H), 7.40 (1H, d, J=2.7 Hz, aromatic-H), 7.17-7.21 (1H, m, aromatic-H), 7.06 (1H, d, J=9.3 Hz, aromatic-H), 5.40 (2H, s, CH$_2$), 3.96 (3H, s, CH$_3$).

EXAMPLE 128

2-(2,4-dichloro-phenoxymethyl)-1H-benzoimidazole-5-carboxylic acid methyl ester

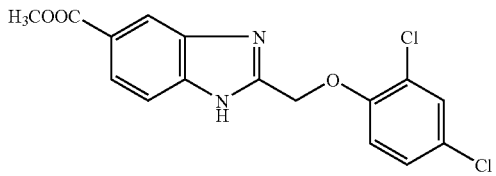

A mixture of 3,4-diamino-benzoic acid methyl ester (105.24 mg, 0.63 mmol) and 2,4-dichlorophenoxy acetic acid (100 mg, 0.45 mmol) in PPSE (1.5 mL) was heated at 160° C. for 4 h. At the end of the reaction period, the mixture was taken to 3 mL dichloromethane and neutralized with 4.5 mL 1 N NaOH solution. The organic layer was separated and the aqueous solution extracted with 3×3 mL portions of dichloromethane. The combined extracts were dried over anhydrous MgSO$_4$, filtered and the solvent was removed with rotary evaporator under reduced pressure. The residue was purified by flash chromatography (EtOAc:Hexanes=1:1) to afford 2-(2,4-dichloro-phenoxymethyl)-1H-benzoimidazole-5-carboxylic acid methyl ester as a colorless powder (0.121 g, 52% yield).

$^1$HNMR (CDCl$_3$, 300 MHz) 8.35 (1H, s, aromatic), 8.01 (1H, dd, J=1.2&8.4H aromatic), 7.64 (1H, brs, NH), 7.39 (1H, d, J=2.4 Hz, aromatic), 7.19 (1H, dd, J=2.4&8.4 Hz, aromatic), 6.97 (1H, d, J=8.4H, aromatic), 5.43 (2H, s, OCH$_2$), 3.94 (3H, s, OCH$_3$).

EXAMPLE 129

2-(2,4-tert-butyl-phenoxymethyl)-benzoxazole-6-carboxylic acid methyl ester

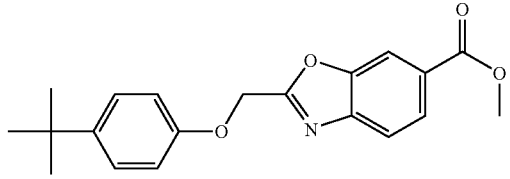 [SMILES: COC(=O)c1ccc2nc(COc3ccc(C(C)(C)C)cc3)oc2c1]

A mixture of (4-tert-butyl-phenoxy)-acetic acid (150.0 mg. 0.72 mmol) and 4-amino-3-hydroxy-benzoic acid methyl ester (168.9 mg, 1.01 mmol) in PPSE (1.5 mL) was heated at 140' for 3 h. At the end of the reaction period, the mixture was taken to dichloromethane and neutralized with 1 N NaOH solution. The organic layer was separated and the aqueous solution extracted with dichloromethane. The combined extracts were dried over anhydrous MgSO$_4$, filtered and the solvent was removed with rotary evaporator under reduced pressure. The residue was purified by flash chromatography (n-Hexane:EtoAc:MeOH=6:3:1) to afford 2-(2,4-tert-butyl-phenoxymethyl)-benzoxazole-6-carboxylic acid methyl ester as a colorless powder (156.2 mg, 64.0% yield).

$^1$H-NMR (CDCl$_3$, 300 Hz) 8.25 (1H, s, aromatic-H), 8.08-8.11 (1H, m, aromatic-H), 7.79 (1H, d, J=8.4 Hz, aromatic- H), 7.31-7.36 (2H, m, aromatic-H), 6.97-7.02 (2H, m, aromatic-H), 5.33 (2H, s, CH$_2$), 3.96 (3H, s, CH$_3$), 1.29 (9H, s, CH$_3$).

EXAMPLE 130

2-(2,4-tert-butyl-phenoxymethyl)-1H-benzoimidazole-5-carboxylic acid methyl ester

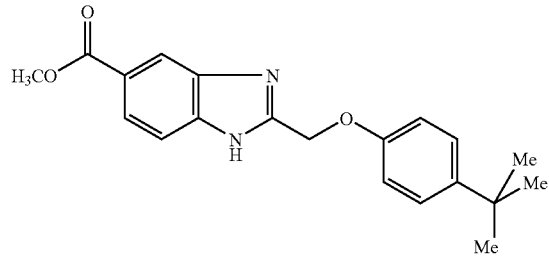 [SMILES: COC(=O)c1ccc2[nH]c(COc3ccc(C(C)(C)C)cc3)nc2c1]

A mixture of (4-tert-butyl-phenoxy)acetic acid (300 mg, 1.4 mmol), 3,4-diaminobenzoic acid methyl ester (300 mg, 1.4 mmol) in PPSE (4.8 mL) was heated at 160° C. for 4 h. At the end of the reaction period, the mixture was taken to ethyl acetate and neutralized with aqueous sodium bicarbonate. The organic layer was separated and the aqueous solution extracted with ethyl acetate. The combined extracts were dried over anhydrous MgSO$_4$, filtered and the solvent was removed with rotary evaporator under reduced pressure. The residue was purified by flash chromatography (EtOAc:Hexane=1:9~4:6) to afford 2-2,4-tert-butyl-phenoxymethyl)-1H-benzoimidazole-5-carboxylic acid methyl ester as a colorless powder (547 mg, 80% yield).

$^1$HNMR (CDCl$_3$, 300 MHz) 8.39 (1H, s, aromatic), 8.03 (1H, d, J=8.1 Hz, aromatic), 7.66 (1H, d, J=7.8 Hz, aromatic), 7.27 (2H, d, J=8.4 Hz, aromatic), 6.88 (2H, d, J=8.7 Hz, aromatic), 5.43 (2H, s, OCH$_2$), 3.95 (3H, s, OCH$_3$), 1.27 (9H, s, t-butyl), NH not detected.

EXAMPLE 131

2-(4-nitro-phenoxymethyl)-1H-benzoimidazole-5-carboxylic acid methyl ester

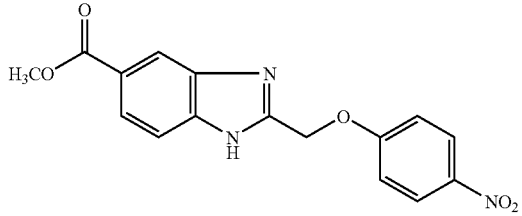 [SMILES: COC(=O)c1ccc2[nH]c(COc3ccc([N+](=O)[O-])cc3)nc2c1]

A mixture of (4-nitro-butyl-phenoxy)-acetic acid (50 mg, 0.25 mmol) and 3,4-diaminobenzoic acid methyl ester (59 mg, 0.35 mmol) in PPSE was heated at 160° C. for 4 h. At the end of the reaction period, the mixture was taken to ethyl acetate and neutralized with aqueous sodium bicarbonate. The organic layer was separated and the aqueous solution extracted with ethyl acetate. The combined extracts were dried over anhydrous MgSO$_4$, filtered and the solvent was removed with rotary evaporator under reduced pressure. The residue was purified by flash chromatography (MeOH: MC=0.5:9.5) to afford 2-(4-nitro-phenoxymethyl)-1H-benzoimidazole-5-carboxylic acid methyl ester as a colorless powder (66.4 mg, 80% yield).

$^1$H NMR (DMSO-d$_6$, 300 MHz) 13.13 (1H, brs, NH), 8.27-8.19 (3H, m, aromatic), 7.85 (1H, dd, J=1.5&8.4 Hz, aromatic), 7.65 (1H, d, J=8.4 Hz, aromatic), 7.34-7.29 (2H, m, aromatic), 6.88 (2H, d, J=8.7 Hz, aromatic), 5.55 (2H, s, OCH$_2$), 3.86 (3H, s, OCH$_3$).

EXAMPLE 132

2-(2,4-dichloro-phenoxymethyl benzoxazole-5-sulfonic acid amide

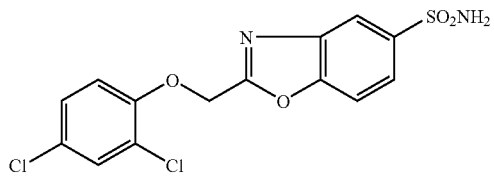 [SMILES: NS(=O)(=O)c1ccc2oc(COc3ccc(Cl)cc3Cl)nc2c1]

A mixture of ((2,4-dichloro-phenoxy)-acetic acid (66.3 mg, 0.3 mmol) and 4-amino-3-hydroxy-benzoic acid methyl ester (79 mg, 0.42 mmol) in PPSE 1 mL was heated at 120° C. for 2 h. At the end of the reaction period, the mixture was taken to dichloromethane and neutralized with aqueous sodium bicarbonate. The organic layer was separated and the aqueous solution extracted with dichloromethane. The combined extracts were dried over anhydrous MgSO$_4$, filtered and the solvent was removed with rotary evaporator under reduced pressure. The residue was purified by flash chromatography (CH$_2$Cl$_2$:MeOH=30:1) to afford 2-(2,4-dichloro-phenoxymethyl)-benzoxazole-5-sulfonic acid amide as a white solid (12 mg, 11% yield).

$^1$H-NMR (CD$^3$OD, 300 Hz) 8.26 (1H, d, J=1.8 Hz, aromatic), 8.00 (1H, dd; J=8.7&1.8 Hz, aromatic), 7.81 (1H, d, J=8.4 Hz, aromatic), 7.45 (1H, d, J=2.4 Hz, aromatic), 7.25 (2H, m, aromatic), 5.50 (2H, s, OCH$_2$).

EXAMPLE 133

2-(2,4-dichloro-phenoxymethyl)-benzoxazole-5-carboxylic acid

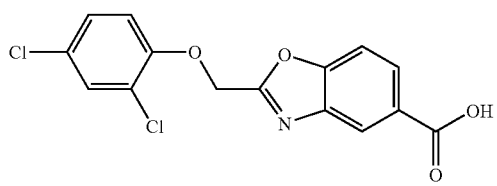 [SMILES: O=C(O)c1ccc2oc(COc3ccc(Cl)cc3Cl)nc2c1]

To a solution of 2-(2,4-dichloro-phenoxymethyl)-benzooxazole-5-carboxylic acid methyl ester (60.0 mg, 0.17 mmol) in dimethyl sulfide (5 ml) and dichloromethane (5 ml) was added aluminum bromide (725.5 Mg, 2.72 mmol). The reaction mixture was stirred at room temperature for 2.5 h, after which water and 10% HCl were added. After stirring at room temperature for 1 h, the mixture was partitioned between ethyl acetate and water. The organic phase was washed with brine, dried (MgSO$_4$ anh), and concentrated. The residue was purified by silica gel flash column chromatography (CH$_2$Cl$_2$:MeOH=4:1) to give 2-(2,4-dichloro-phenoxymethyl)-benzoxazole-5-carboxylic acid as a white solid (42.0 mg, 72.9% yield).

$^1$H-NMR (CDCl$_3$+CD$_3$OD, 300 Hz) 8.25 (1H, s, aromatic-H), 8.07-8.10 (1H, m, aromatic-H), 7.74 (1H, d, J=8.7 Hz, aromatic-H), 7.38 (1H, d, J=2.4 Hz, aromatic-H), 7.18-7.22 (1H, m, aromatic-H), 7.12 (1H, d, J=8.4 Hz, aromatic-H), 5.42 (2H, s, CH$_2$).

EXAMPLE 134

2-(4-adamantan-1-yl-phenoxymethyl)-benzoxazole-5-carboxylic acid

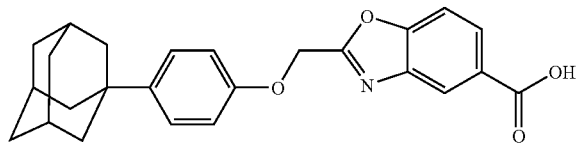 [SMILES: O=C(O)c1ccc2oc(COc3ccc(C45CC6CC(CC(C6)C4)C5)cc3)nc2c1]

To a solution of 2-(4-adamantan-1-yl-phenoxymethyl)-benzoxazole-5-carboxylic acid methyl ester (100 mg, 0.24 mmol) in dimethyl sulfide (5 ml) and dichloromethane (5 ml) was added aluminum bromide (1.02 g, 3.84 mmol). The reaction mixture was stirred at room temperature for 2.5 h, after which water and 10% HCl were added. After stirring at room temperature for 1 h, the mixture was partitioned between ethyl acetate and water. The organic phase was washed with brine, dried (MgSO$_4$ anh), and concentrated. The residue was purified by silica gel flash column chromatography (CH$_2$Cl$_2$:MeOH=4:1) to give 2-(4-adamantan-1-yl-phenoxymethyl)-benzoxazole-5-carboxylic acid as a white solid (63.8 mg, 66.0% yield).

$^1$H-NMR (CD$_3$OD, 300 Hz) 8.40 (1H, m, aromatic-H), 8.08-8.11 (1H, m, aromatic-H), 7.58 (1H, d, J=8.4 Hz, aromatic-H), 7.37 (1H, s, aromatic-H), 7.23-7.29 (2H, m, aromatic-H), 6.93-6.98 (2H, m, aromatic-H), 5.29 (2H, s, CH$_2$), 2.03 (3H, m, adamantly-H), 1.83 (6H, m, adamantly-H), 1.71 (6H, m, adamantly-H).

EXAMPLE 135

2-(4-adamantan-1-yl-phenoxymethyl)-benzoxazole-6-carboxylic acid

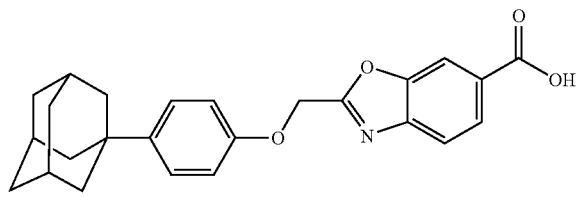 [SMILES: O=C(O)c1ccc2nc(COc3ccc(C45CC6CC(CC(C6)C4)C5)cc3)oc2c1]

To a solution of 2-(4-adamantan-1-yl-phenoxymethyl)-benzoxazole-6-carboxylic acid methyl ester (110 mg, 0.26 mmol) in dimethyl sulfide (10 ml) and dichloromethane (10 ml) was added aluminum bromide (1.13 g, 4.22 mmol). The reaction mixture was stirred at room temperature for 2.5 h, after which water and 10% HCl were added. After stirring at room temperature for 1 h, the mixture was partitioned between ethyl acetate and water. The organic phase was washed with brine, dried (MgSO$_4$ anh), and concentrated. The residue was purified by silica gel flash column chromatography (CH$_2$Cl$_2$:MeOH=4:1) to give 2-(4-adamantan-1-yl-phenoxymethyl)-benzoxazole-6-carboxylic acid as a white solid (81.6 mg, 76.8% yield).

$^1$H-NMR (DMSO-d$_6$, 300 Hz) 8.25 (1H, s, aromatic-H), 8.02 (1H, d, J=7.8 Hz, aromatic-H), 7.82 (1H, d, J=8.7 Hz, aromatic-H), 7.28 (2H, d, J=8.7 Hz, aromatic-H), 7.01 (2H, d, J=8.4 Hz aromatic-H), 5.46 (2H, s, CH$_2$), 2.02 (3H, m, adamantly-H), 1.81 (6H, m, adamantly-H), 1.70 (6H, m, adamantly-H).

EXAMPLE 136

2-(4-adamantan-1-yl-phenoxymethyl)-1H-benzoimidazole-5 carboxylic acid

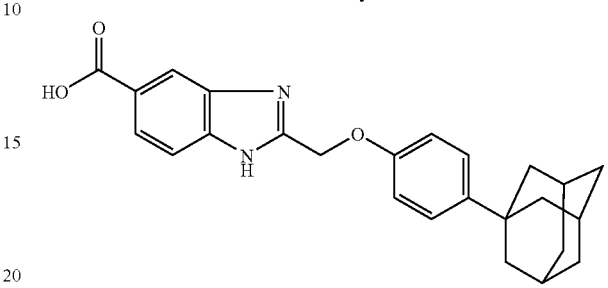

A mixture of 2-(4-adamantan-1-yl-phenoxymethyl)-1H-benzoimidazole-5-carboxylic acid methyl ester (200 mg, 0.48 mmol), acetic acid (130 mL) and concd HCl (100 mL) was heated under reflux for 3 h. At the end of the reaction period, the mix was cooled to 10° C., neutralized with aqueous sodium bicarbonate solution, filtered, washed with ethyl acetate (10 mL), water (50 mL) and dried to afford 2 (4-adamantan-1-yl-phenoxymethyl)-1H-benzoimidazole-5-carboxylic acid as a colorless powder (0.162 g, 84% yield).

$^1$H NMR (CDCl$_3$, 300 MHz) 8.27 (1H, s, aromatic), 8.0 (1H, d, J=84 Hz), 7.8 (1H, d, J=8.7 Hz), 7.31 (2H, d, J=8.4 Hz), 7.06 (2H, d, J=9 Hz), 5.5 (2H, s, OCH$_2$), 2.03 (3H, s, adamantyl), 1.81 (6H, d, J=3.3 Hz, adamantyl), 1.71 (6H, m, adamantyl), COOH and NH not detected.

EXAMPLE 137

2-(2,4-dichloro-phenoxymethyl)-benzoxazole-6-carboxylic acid

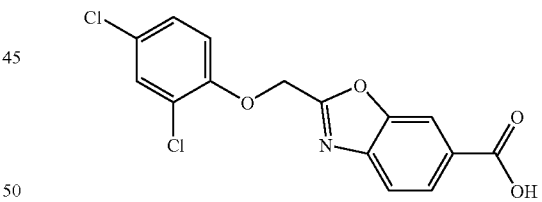

To a solution of 2-(2,4-dichloro-phenoxymethyl)-benzoxazole-6-carboxylic acid methyl ester (100 mg, 0.29 mmol) in dimethyl sulfide (8 ml) and dichloromethane (58 ml) was added aluminum bromide (1.24 g, 4.64 mmol). The reaction mixture was stirred at room temperature for 2.5 h, after which water and 10% HCl were added. After stirring at room temperature for 1 h, the mixture was partitioned between ethyl acetate and water. The organic phase was washed with brine, dried (MgSO$_4$ anh), and concentrated. The residue was purified by silica gel flash column chromatography (CH$_2$Cl$_2$:MeOH=4:1) to give 2-2,4-dichloro-phenoxymethyl)-benzoxazole-6-carboxylic acid as a white solid (59.15 mg mg, 61.2% yield).

$^1$H-NMR (DMSO-d$_6$, 300 Hz) 13.22 (1H, s, COOH), 8.28 (1H, s, aromatic-H), 8.00-8.03 (1H, m, aromatic-H), 7.88

(1H, d, J=8.4 Hz, aromatic-H), 7.64-7.65 (1H, m, aromatic-H), 7.34-7.43 (2H, m, aromatic-H), 5.66 (2H, s, CH$_2$).

EXAMPLE 138

2-(2,4-dichloro-phenoxymethyl)-1H-benzoimidazole-5-carboxylic acid

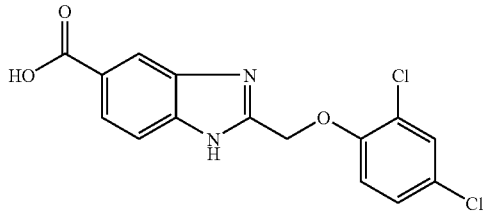 [SMILES: O=C(O)c1ccc2[nH]c(COc3ccc(Cl)cc3Cl)nc2c1]

A mixture of 2-(2,4-dichlorophenoxymethyl)-1H-benzoimidazole-5-carboxylic acid methyl ester (110 mg, 0.31 mmol), acetic acid (60 mL) and concd HCl (60 mL) was heated under reflux for 3 h. At the end of the reaction period, the mixture was cooled to 10° C., neutralized with aqueous sodium bicarbonate solution, filtered, washed with ethyl acetate (10 mL), water (50 mL) and dried to afford 2-2,4-chloro-phenoxymethyl)-1H-benzoimidazole-5-carboxylic acid as a colorless powder (0.099 g, 94.28% yield).

$^1$H NMR (CDCl$_3$, 300 MHz) 13.16 (2H, brs, COOH, NH), 8.27 (1H, s, aromatic), 7.99 (1H, d, J=9.0 Hz, aromatic), 7.79 (1H, d, J=8.7 Hz, aromatic), 7.65 (1H, d, J=1.8 Hz, aromatic), 7.41 (2H, m, aromatic), 5.64 (2H, s, OCH$_2$).

EXAMPLE 139

2-(4-tert-butyl-phenoxymethyl)-benzoxazole-6-carboxylic acid

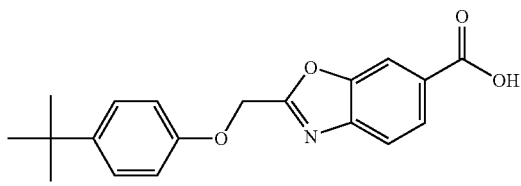 [SMILES: CC(C)(C)c1ccc(OCc2nc3ccc(C(=O)O)cc3o2)cc1]

To a solution of 2-(4-tert-butyl-phenoxymethyl)-benzoxazole-6-carboxylic acid methyl ester (67.8 mg, 0.20 mmol) in dimethyl sulfide (3 ml) and dichloromethane (3 ml) was added aluminum bromide (533.4 g, 2.0 mmol). The reaction mixture was stirred at room temperature for 2.5 h, after which water and 10% HCl were added. After stirring at room temperature for 1 h, the mixture was partitioned between ethyl acetate and water. The organic phase was washed with brine, dried (MgSO$_4$ anh), and concentrated. The residue was purified by silica gel flash column chromatography (n-Hexane:EtoAc:MeOH=6:3:1) to give 2-(4-tert-butyl-phenoxymethyl)-benzoxazole-6-carboxylic acid as a white solid (50.5 mg, 77.7% yield).

$^1$H-NMR (DMSO-d$_6$, 300 Hz) 8.27 (1H, s, aromatic-H), 8.01 (1H, d, J=8.4 Hz aromatic-H), 7.86 (1H, d, J=8.71 k; aromatic-H), 7.31-7.34 (2H, m, aromatic-H), 6.99-7.02 (2H, m, aromatic-H), 5.47 (2H, s, CH$_2$), 1.24 (9H, s, CH$_3$).

EXAMPLE 140

2-(4-tert-butyl-phenoxymethyl)-1H-benzoimidazole-5-carboxylic acid

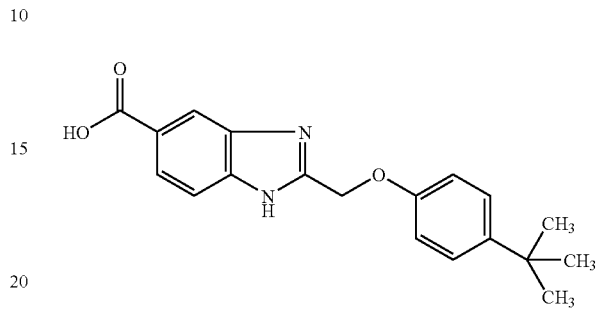

A mixture of 2-(4-tert-butyl-phenoxymethyl)-1H-benzoimidazole-5-carboxylic acid methyl ester (150 mg, 0.44 mmol), acetic acid (30 mL) and concd HCl (39 mL) was heated under reflux for 3 h. At the end of the reaction period, the mixture was cooled to 10° C., neutralize with aqueous sodium bicarbonate solution, filtered, washed with ethyl acetate (10 mL), water (50 mL) and dried to afford 2-(4-tert-butyl-phenoxymethyl)-1H-benzoimidazole-5-carboxylic acid as a colorless powder (0.13 g, 90% yield).

$^1$H NMR (DMSO-d$_6$, 300 MHz) 8.24 (1H, s, aromatic), 8.02 (1H, d, J=8.4H aromatic), 7.82 (1H, d, J=8.4 Hz, aromatic), 7.35 (2H, d, J=8.4 Hz, aromatic), 7.05 (2H, d, J=9.3 Hz, aromatic), 5.57 (2H, s, OCH$_2$), 1.25 (9H, s, C(CH$_3$)$_3$), COOH and NH not detected.

EXAMPLE 141

2-(4-nitro-phenoxymethyl)1H-benzoimidazole-5-carboxylic acid

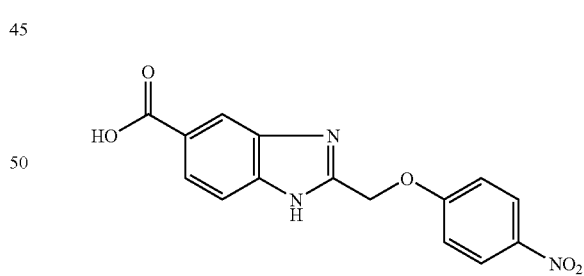

A mixture of 2-(4-nitro-phenoxymethyl)-1H-benzoimidazole-5-carboxylic acid methyl ester (90 mg, 0.27 mmol), acetic acid (15 mL) and concd HCl (20 mL) was heated under reflux for 3 h. At the end of the reaction period, the mixture was cooled to 10° C., neutralize with aqueous sodium bicarbonate solution, filtered, washed with ethyl acetate (10 mL), water (50 mL) and dried to afford 2-(4-nitro-phenoxymethyl)-1H-benzoimidazole-5-carboxylic acid as a colorless powder (0.078 g, 90% yield).

$^1$H NMR (DMSO-d$_6$, 300 MHz) 8.29-8.25 (3H, m, aromatic), 8.02-7.99 (1H, m, aromatic), 7.83-7.81 (1H, m, aromatic), 7.37 (2H, d, J=9.0 Hz, aromatic), 7.65 (1H, d, J=1.8 Hz, aromatic), 7.41 (2H, m, aromatic), 5.77 (2H, s, OCH₂), COOH and NH not detected.

EXAMPLE 142

2-(4-adamantan-1-yl-phenoxymethyl)-benzoxazole-5-carboxylic acid amide

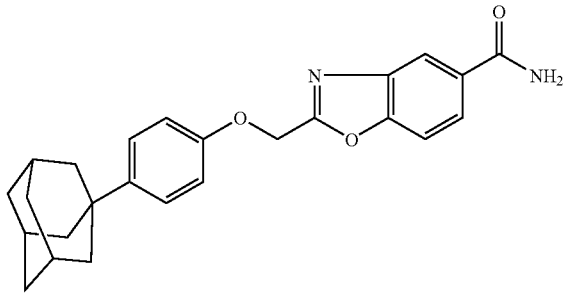 [SMILES: NC(=O)c1ccc2oc(COc3ccc(C45CC6CC(CC(C6)C4)C5)cc3)nc2c1]

To solution of 2-(4-adamantan-1-yl-phenoxymethyl)-benzoxazole-5-carboxylic acid (72.1 mg, 0.18 mmol), ammonium chloride (19.1 mg, 0.36 mmol) in DMF 4.0 mL was added HBTU (136.53 mg, 0.36 mmol) and DIPEA (0.063 ml, 0.36 mmol). After stirring at room temperature, the mixture was partitioned between ethyl acetate and brine. The organic phase was dried (MgSO₄ anh), and concentrated. The residue was purified by silica gel column chromatography (CH₂Cl₂:MeOH=15:1) to give 2-(4-adamantan-1-yl-phenoxymethyl)-benzoxazole-5-carboxylic acid amide as a yellow solid (2.7 mg, 4% yield).

¹H-NMR (DMSO-d₆, 300 Hz) 10.54 (1H, s, NH), 8.81 (1H, s, aromatic), 8.65 (1H, s, aromatic), 8.53 (1H, s, aromatic), 8.44 (1H, s, aromatic), 8.02-8.12 (4H, m, aromatic), 7.84 (1H, m, aromatic), 7.62-7.76 (5H, m, aromatic), 7.41-7.49 (3H, m, aromatic), 7.26 (1H, m, aromatic).

EXAMPLE 143

2-(4-adamantan-1-yl-phenoxymethyl)-benzoxazole-5-carboxylic acid dimethylamide

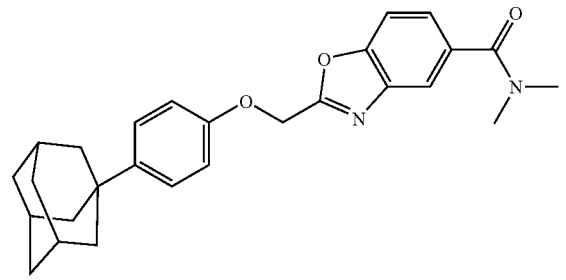 [SMILES: CN(C)C(=O)c1ccc2oc(COc3ccc(C45CC6CC(CC(C6)C4)C5)cc3)nc2c1]

To solution of 2-(4-adamantan-1-yl-phenoxymethyl)-benzoxazole-5-carboxylic acid (60.4 mg, 0.15 mmol), dimethyl amine (0.030 ml, in 2M THF) in DMF 5.0 mL was added HBTU (113.8 mg, 0.30 mmol) and DIPEA (0.052 ml, 0.30 mmol). After sting at room temperature, the mixture was partitioned between ethyl acetate and brine. The organic phase was dried (MgSO₄ anh), and concentrated. The residue was purified by silica gel column chromatography (n-Hexane:EtOAc:MeOH=15:3:1) to give 2-(4-adamantan-1-yl-phenoxymethyl)-benzoxazole-5-carboxylic acid dimethylamide as a white solid (37.9 mg, 59% yield).

¹H-NMR (CD₃OD, 300 Hz) 7.79 (1H, d, J=1.2 Hz, aromatic), 7.71 (1H, d, J=8.4 Hz, aromatic), 7.49 (1H, dd, J=8.4&1.2 Hz, aromatic), 7.28 (2H, m, aromatic), 6.98 (2H, m, aromatic), 5.36 (2H, s, OCH₂CO), 3.12 (3H, s, CH₃), 3.00 (3H, s, CH₃), 2.05 (3H, m, adamantyl), 1.88-1.89 (6H, m, adamantyl), 1.74-1.83 (6H, m, adamantyl)

EXAMPLE 144

2-(4-adamantan-1-yl-phenoxymethyl)-benzoxazole-5-carboxylic acid (furan-2-ylmethyl)amide

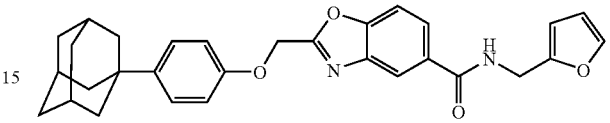

To solution of 2-(4-adamantan-1-yl-phenoxymethyl)-benzoxazole-5-carboxylic acid (30.1 mg, 0.08 mmol), furfuryl amine (11.0 mg, 0.12 mmol, 0.01 ml), EDC (21.7 mg, 0.12 mmol) and HOBt (15.4 mg, 0.12 mmol) in DMF 3.0 mL was added DIPEA (14.2 mg, 0.12 mmol, 0.02 ml). After string at room temperature, the mixture was partitioned between ethyl acetate and brine. The organic phase was dried (MgSO₄ anh), and concentrated. The residue was purified by silica gel column chromatography (n-Hexane:EtOAc:MeOH=6:3:1) to give 2-(4-adamantan-1-yl-phenoxymethyl)-benzoxazole-5-carboxylic acid dimethylamide as a white solid (32.9 mg, 90.9% yield).

¹H-NMR (CDCl₃, 300 Hz) 8.15 (1H, m, aromatic-H), 7.86-7.89 (1H, m, aromatic-H), 7.59 (1H, d, J=8.7 Hz, aromatic-H), 7.39 (1H, m, aromatic-H), 7.28-7.31 (2H, m, aromatic-H), 6.99-7.01 (2H, m, aromatic-H), 6.42 (1H, s, NH), 6.32-6.37 (2H, m, aromatic-H), 5.31 (2H, s, CH₂), 4.67 (2H, d, J=5.7 Hz, CH₂), 2.08 (3H, m, adamantly-H), 1.87 (6H, m, adamantly-H), 1.76 (6H, m, adamantly-H).

EXAMPLE 145

2-(4-adamantan-1-yl-phenoxymethyl)-benzoxazole-5-carboxylic acid (2-dimethylamino-ethyl)-amide

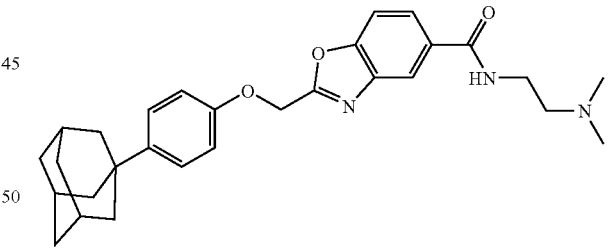

To solution of 2-(4-adamantan-1-yl-phenoxymethyl)-benzoxazole-5-carboxylic acid (57.7 mg, 0.14 mmol) and 3-morpholine-4-yl-propylamine (0.031 ml, 0.29 mmol) in DMF 4.0 mL was added HBTU (109.98 mg, 0.29 mmol) and DIPEA (0.051 ml, 0.29 mmol). After stilling at room temperature, the mixture was partitioned between ethyl acetate and brine. The organic phase was dried (MgSO₄ anh), and concentrate. The residue was purified by silica gel column chromatography (CH₂Cl₂:MeOH=10:1) to give 2-(4-adamantan-1-yl-phenoxymethyl)-benzoxazole-5-carboxylic acid (2-dimethylamino-ethyl)-amide as a white solid (38.2 mg, 58% yield).

¹H-NMR (CD₃OD, 300 Hz) 8.21 (1H, d, J=1.8 Hz, aromatic), 7.94 (1H, dd, J=8.7&1.8 Hz, aromatic), 7.69 (1H, d, J=8.4 Hz, aromatic), 7.27 (2H, m, aromatic), 6.97 (2H, m, aromatic), 5.35 (2H, s, OCH$_2$CO), 3.60 (2H, t, J=6.6 Hz, aliphatic), 2.79 (2H, t, J=6.6 Hz, aliphatic), 2.48 (6H, s, N(CH$_3$)), 2.04 (3H, m, adamantyl), 1.83-1.90 (6H, m, adamantly), 1.73-1.78 (6H, m, adamantly).

EXAMPLE 146

2-(4-adamantan-1-yl-phenoxymethyl)-benzoxazole-5-carboxylic acid (2-piperidine-1-yl-ethyl)-amide

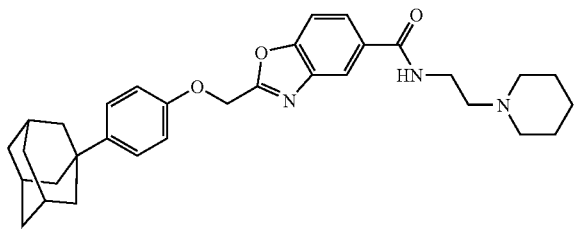 [SMILES: O=C(NCCN1CCCCC1)c1ccc2oc(COc3ccc(C45CC6CC(CC(C6)C4)C5)cc3)nc2c1]

To solution of 2-(4-adamantan-1-yl-phenoxymethyl)-benzoxazole-5-carboxylic acid (70.2 mg, 0.17 mmol) and 2-piperidine-1-yl-ethylamine (0.049 ml, 0.35 mmol) in DMF 5.0 mL was added HBTU (132.7 mg, 0.35 mmol) and DIPEA (0.061 ml, 0.35 mmol). After stirring at room temperature, the mixture was partitioned between ethyl acetate and brine. The organic phase was dried (MgSO$_4$ anh), and concentrated. The residue was purified by silica gel column chromatography (CH$_2$Cl$_2$:MeOH=20:1) to give 2-(4-adamantan-1-yl-phenoxymethyl)-benzoxazole-5-carboxylic acid (2-piperidine-1-yl-ethyl)-amide as a white foam (18.9 mg, 22% yield).

$^1$H-NMR (CD$_3$OD, 300 Hz) 8.22 (1H, d, J=1.2 Hz, aromatic), 7.96 (1H, dd, J=8.7 & 1.8, aromatic), 7.71 (1H, d, J=8.4 Hz, aromatic), 7.27 (2H, m, aromatic), 6.97 (2H, m, aromatic), 5.36 (2H, s, OCH$_2$CO), 3.74 (2H, t, J=6.0 Hz, aliphatic), 3.03-3.19 (6H, m, aliphatic), 2.04 (3H, m, adamantyl), 1.73-1.88 (16H, m, adamantly, aliphatic), 1.64 (2H, m, aliphatic)

EXAMPLE 147

2-(4-adamantan-1-yl-phenoxymethyl)-benzoxazole-5-carboxylic acid (3-morpholine-4-yl-propyl)amide

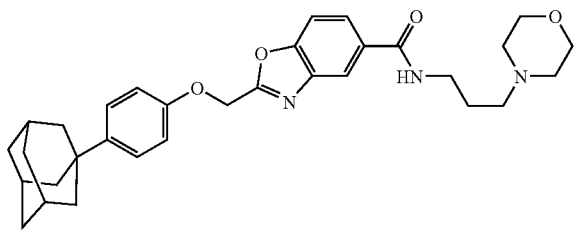 [SMILES: O=C(NCCCN1CCOCC1)c1ccc2oc(COc3ccc(C45CC6CC(CC(C6)C4)C5)cc3)nc2c1]

To solution of 2-(4-adamantan-1-yl-phenoxymethyl)-benzoxazole-5-carboxylic acid (73.9 mg, 0.18 mmol) and 3-morpholine-4-yl-propylamine (0.053 ml, 0.37 mmol) in DMF 4.0 mL was added HATU (54.8 mg, 0.37 mmol) and DIPEA (0.064 ml, 0.37 mmol). After stirring at room temperature, the mixture was partitioned between ethyl acetate and brine. The organic phase was dried (MgSO$_4$ anh), and concentrated. The residue was purified by silica gel column chromatography (CH$_2$Cl$_2$:MeOH=10:1) to give 2-(4-adamantan-1-yl-phenoxymethyl)-benzoxazole-5-carboxylic acid (3-morpholine-4-yl-propylamide as a white foam (11.9 mg, 13% yield).

$^1$H-NMR (CD$_3$OD, 300 Hz) 8.18 (1H, d, J=1.8 Hz aromatic), 7.91 (1H, dd, J=9.0 & 1.2 Hz, aromatic), 7.69 (1H, d, J=8.4 Hz, aromatic), 7.27 (2H, m, aromatic), 6.97 (2H, m, aromatic), 5.35 (2H, s, OCH$_2$CO), 3.69 (4H, m, aliphatic), 3.45 (2H, t, J=6.9H aliphatic), 2.47-2.52 (6H, m, aliphatic), 2.04 (3H, m, adamantyl), 1.82-1.88 (8H, m, adamantly, aliphatic), 1.73-1.78 (6H, m, adamantyl)

EXAMPLE 148

2-(2,4-dichloro-phenoxymethyl)-benzoxazole-5-carboxylic acid (furan-2-ylmethyl)-amide

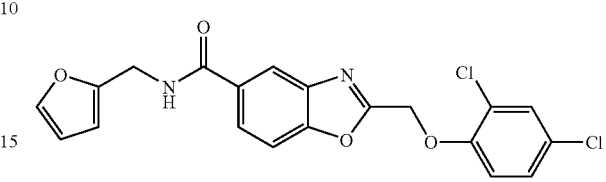

furfuryl amine (28.2 mg, 0.29 mmol, 0.03 ml) was dissolved in dry toluene (3 ml) and treated with trimethylaluminium (2.0 M in hexane) (0.64 ml. 1.28 mmol) with stirring under argon. After 0.25 h, a solution of the 2-2,4-Dichloro-phenoxymethyl)-benzooxazole-5-carboxylic acid methyl ester (100.2 mg, 0.29 mmol) in toluene (9 ml) was added. The mixture was then stirred at 80° C. for 1 h, the reaction mixture was allowed to cool and was treated with dilute HCl, until no more effervescence took place. The reaction mixture was then partitioned between ethyl acetate and water. The organic phase was washed with brine, dried (MgSO$_4$ anh), and concentrated. The residue was purified by Prep-TLC (CH$_2$Cl$_2$:MeOH=15:1) to give 2-(2,4-dichloro-phenoxymethyl)-benzoxazole-5-carboxylic acid (furan-2-ylmethyl)-amide as a white solid (86.6 mg, 71.8% yield).

$^1$H-NMR (DMSO-d$_6$, 300 Hz) 9.09 (1H, t, J=5.4 Hz, NH), 8.30 (1H, s, aromatic-H), 7.98-8.02 (1H, m, aromatic-H), 7.86 (1H, d, J=8.7 Hz, aromatic-H), 7.63 (1H, d, J=2.4 Hz, aromatic-H), 7.58 (1H, s, aromatic-H), 7.35-7.43 (2H, m, aromatic-H), 6.40-6.41 (1H, m, aromatic-H), 6.30-6.31 (1H, m, aromatic-H), 5.63 (2H, s, CH$_2$), 4.49 (2H, d, J=5.7 Hz, CH$_2$).

EXAMPLE 149

2-(4-adamantan-1-yl-phenoxymethyl)-benzoxazole-6-carboxylic acid (furan-2-ylmethyl)-amide

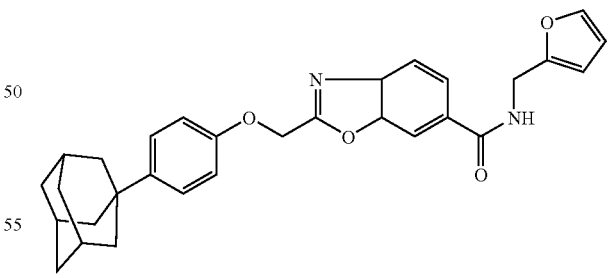

To solution of 2-(4-adamantan-1-yl-phenoxymethyl)-benzoxazole-6-carboxylic acid (30.1 mg, 0.08 mmol), furfuryl amine (11.0 mg, 0.12 mmol, 0.01 ml), EDC (21.7 mg, 0.12 mmol) and HOBt (15.4 mg, 0.12 mmol) in DMF 3.0 mL was added DIPEA (14.2 mg, 0.12 mmol, 0.02 ml). After stirring at room temperature, the mixture was partitioned between ethyl acetate and brine. The organic phase was dried (MgSO$_4$ anh), and concentrated. The residue was purified by silica gel column chromatography (n-Hexane:EtOAc:MeOH=6:3:1) to give 2-adamantan-1-yl-phenoxymethyl)-benzoxazole-6-carboxylic acid (furan-2-ylmethyl)-amide as a white solid (6.3 mg, 17.4% yield).

$^1$H-NMR (CDCl$_3$+CD$_3$OD, 300 Hz) 8.25 (1H, d, J=8.7 Hz, aromatic-H), 7.60 (1H, s, aromatic-H), 7.28-7.35 (4H, m, aromatic-H), 6.92-6.97 (2H, m, aromatic-H), 6.24-6.31 (2H, m, aromatic-H), 4.61 (2H, s, CH$_2$), 4.51 (2H, s, CH$_2$), 2.05 (3H, m, adamantly-1H), 1.86 (6H, m, adamantly-H), 1.75 (6H, m, adamantly-H).

EXAMPLE 150

2-(2,4-dichloro-phenoxymethyl benzoxazole-6-carboxylic acid (furan-2-ylmethyl)amide

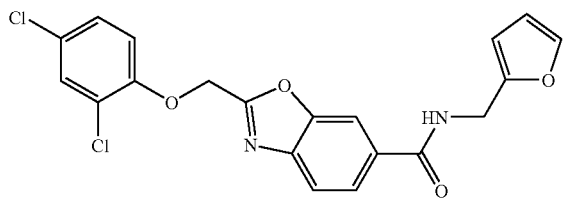 [SMILES: O=C(NCc1ccco1)c1ccc2nc(COc3ccc(Cl)cc3Cl)oc2c1]

To solution of 2-(4-adamantan-1-yl-phenoxymethyl)-benzoxazole-6-carboxylic acid (30.0 mg, 0.09 mmol), furfuryl amine (13.0 mg, 0.14 mmol, 0.013 ml), EDC (25.7 mg, 0.14 mmol) and HOBt (18.24 mg, 0.14 mmol) in DMF 3.0 mL was added DIPEA (16.8 mg, 0.14 mmol, 0.02 ml). After stirring at room temperature, the mixture was partitioned between ethyl acetate and 10% HCl. The organic phase was washed with brine, dried (MgSO$_4$ anh), and concentrated. The residue was purified by silica gel column chromatography (n-Hexane: EtOAc:MeOH=6:3:1) to give 2-(2,4-dichloro-phenoxymethyl)-benzoxazole-6-carboxylic acid (furan-2-ylmethyl)-amide as a white solid (14.7 mg, 37.9% yield).

$^1$H-NMR (DMSO-d$_6$, 300 Hz) 9.10 (1H, t J=6.0 Hz, NH), 8.26 (1H, s, aromatic-H), 7.94-7.97 (1H, m, aromatic-H), 7.86 (1H, d, J=8.7 Hz, aromatic-H), 7.64 (1H, d, J=2.4 Hz, aromatic-H), 7.59 (1H, s, aromatic-H), 7.34-7.43 (2H, m, aromatic-H), 6.40-6.41 (1H, m, aromatic-H), 6.30-6.31 (1H, m, aromatic-H), 5.65 (2H, s, CH$_2$), 4.50 (2H, d, J=5.7 Hz, CH$_2$).

EXAMPLE 151

2-(4-adamantan-1-yl-phenoxymethyl)-3H-benzoimidazole-5-carboxylic acid amide

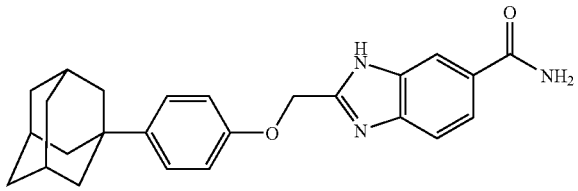 [SMILES: NC(=O)c1ccc2nc(COc3ccc(C45CC6CC(CC(C6)C4)C5)cc3)[nH]c2c1]

To solution of 2-(4-adamantan-1-yl-phenoxymethyl)-3H-benzoimidazole-5-carboxylic acid (44-0.8 mg, 0.11 mmol), ammonium chloride (11.8 mg, 0.22 mmol), EDC (32.6 mg, 0.17 mmol) and HOBt (23.0 mg, 0.17 mmol) in DMF 3.0 mL was added DIPEA (0.03 ml 0.17 mmol). After stirring at room temperature, the mixture was partitioned between ethyl acetate and 10% HCl. The organic phase was washed with brine, dried (MgSO$_4$ anh), and concentrated. The residue was purified by silica gel column chromatography (CH$_2$Cl$_2$: MeOH=6:1) to give 2-(4-adamantan-1-yl phenoxymethyl)-3H benzoimidazole-5-carboxylic acid amide as a white solid (16.8 mg, 37.5% yield).

$^1$HNMR (CDCl$_3$, 300 Hz) 8.13 (1H, s, aromatic-H), 7.80 (1H, d, J=8.7H aromatic-H), 7.62 (1H, d, J=8.1 Hz, aromatic-H), 7.26 (2H, d, J=8.7 Hz, aromatic-H), 6.95 (2H, d, J=8.4 Hz, aromatic-H), 5.32 (2H, s, CH$_2$), 2.03 (3H, m, adamantly-H), 1.83 (6H, m, adamantly-H), 1.72 (6H, m, adamantly-H).

EXAMPLE 152

2-(4-adamantan-1-yl-phenoxymethyl)-3H-benzoimidazole-5-carboxylic acid dimethylamide

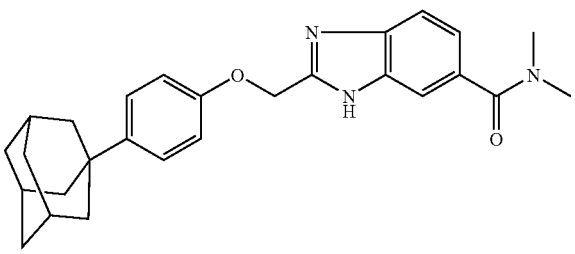 [SMILES: CN(C)C(=O)c1ccc2nc(COc3ccc(C45CC6CC(CC(C6)C4)C5)cc3)[nH]c2c1]

To solution of 2-(4-adamantan-1-yl-phenoxymethyl)-1H-benzoimidazole-5-carboxylic acid (44.8 mg, 0.11 mmol), dimethyl amine (0.4 mg, 0.23 mmol), EDC (44.1 mg, 0.23 mmol) and HOBt (31.3 mg, 0.23 mmol) in DMF 4.0 mL was added DIPEA (28.8 mg, 0.23 mmol, 0.04 ml). After stirring at room temperature, the mixture was partitioned between ethyl acetate and 10% HCl. The organic phase was washed with brine, dried (MgSO$_4$ anh), and concentrated. The residue was purified by Prep-TLC (n-Hexane:EtoAc:MeOH=6:3:1) to give 2-(4-adamantan-1-yl-phenoxymethyl)-3H-benzoimidazole-5-carboxylic acid dimethylamide as a yellow solid (27.8 mg, 54.0% yield)

$^1$H-NMR (CDCl$_3$, 300 Hz) 7.71 (1H, s, aromatic-H), 7.57 (1H, d, J=8.7 Hz, aromatic-H), 7.19-7.28 (3H, m, aromatic-H), 6.87 (2H, d, J=8.7 Hz, aromatic-H), 5.33 (2H, s, CH$_2$), 3.11 (3H, s, CH$_3$), 2.97 (3H, s, CH$_3$), 2.06 (3H, m, adamantly-H), 1.83 (6H, m, adamantly-H), 1.68-1.79 (6H, m, adamantly-H).

EXAMPLE 153

2-(4-adamantan-1-yl-phenoxymethyl)-1H-benzoimidazole-5-carboxylic acid (furan-2-ylmethyl)-amide

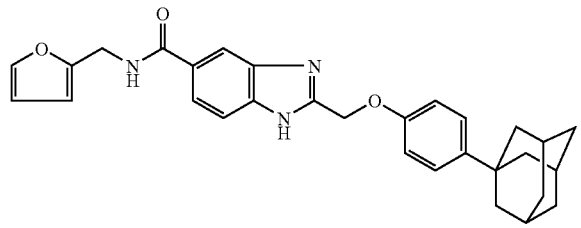 [SMILES: O=C(NCc1ccco1)c1ccc2[nH]c(COc3ccc(C45CC6CC(CC(C6)C4)C5)cc3)nc2c1]

To a solution of 2-(4-adamantan-1-yl-phenoxymethyl)-1H-benzoimidazole-5-carboxylic acid (50 mg, 0.124 mmol), furfuryl amine (18 mg, 0.186 mmol) and DMAP (22.78 mg, 0.186 mmol) in DMF (1 mL) was added PyBOP (97 mg, 0.186 mmol) at room temperature. The mixture was stirred for 16 h at room temperature and then poured into water (150 mL). The resulting solid was extracted with a mixture of methanol:MC (10%), washed with brine, aqueous sodium bicarbonate and water, dried over anhydrous MgSO$_4$, filtered and concentrated under reduced pressure. The resulted crude product was purified by PLC (methanol: MC=0.5:9.5) to afford 2-(4-adamantan-1-yl-phenoxymethyl)-1H-benzoimidazole-5-carboxylic acid (furan-2-ylmethyl)-amide as a colorless solid (43.2 mg, 72% yield).

$^1$H NMR (CDCl$_3$, 300 MHz) 8.08 (1H, s, CONH), 7.59 (1H, d, J=8.4 Hz, furan), 7.46 (1H, d, J=8.7 Hz, furan), 7.29 (1H, s, aromatic), 7.15 (2H, d, J=8.4 Hz, aromatic), 7.07 (1H, m, furan), 6.79 (2H, d, J=8.4 Hz, aromatic), 6.24 (2H, d, J=12.3 Hz, aromatic), 5.21 (2H, s, OCH$_2$), 4.59 (2H, d, J=4.8 Hz, furan-CH$_2$NH), 2.02 (3H, s, adamantyl), 1.76-1.65 (12H, m, adamantyl), benzoimidazole NH not detected.

EXAMPLE 154

2-(4-adamantan-1-yl-phenoxymethyl)-1H-benzoimidazole-5-carboxylic acid (2-dimethylamino-ethyl)-amide

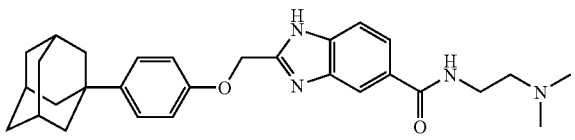 [SMILES: CN(C)CCNC(=O)c1ccc2[nH]c(COc3ccc(C45CC6CC(CC(C6)C4)C5)cc3)nc2c1]

To solution of 2-(4-adamantan-1-yl-phenoxymethyl)-1H-benzoimidazole-5-carboxylic acid (70.0 mg, 0.18 mmol), N,N-diethylethylenediamine (23.8 mg, 0.27 mmol, 0.03 ml) and HBTU (136.5 mg, 0.36 mmol) in DMF 4.0 mL was added DIPEA (46.5 mg, 0.36 mmol, 0.06 ml). After stirring at room temperature, the mixture was partitioned between ethyl acetate and brine. The organic phase was dried (MgSO$_4$ anh), and concentrated. The residue was purified by Prep-TLC (CH$_2$Cl$_2$:MeOH=10:1) to give 2-(4-adamantan-1-yl-phenoxymethyl)-1H-benzoimidazole-5-carboxylic acid (2-dimethylamino-ethyl)-amide as a yellow solid (21.9 mg, 25.8% yield).

$^1$H-NMR (CDCl$_3$+CD$_3$OD, 300 Hz) 8.39 (1H, s, aromatic-H), 8.03 (1H, d, J=8.7 Hz, aromatic-H), 7.72-7.74 (1H, m, aromatic-H), 7.29 (2H, d, J=−9.0 Hz, aromatic-H), 6.97 (2H, d, J=−9.3 Hz, aromatic-H), 5.45 (2H, s, CH$_2$), 3.79 (2H, m, CH$_2$), 3.37 (2H, m, CH$_2$), 2.93 (6H, m, CH$_3$), 2.04 (3H, m, adamantly-H), 1.83 (6H, m, adamantly-H), 1.66-1.77 (6H, m, adamantly-H).

EXAMPLE 155

2-(4-adamantan-1-yl-phenoxymethyl)-1H-benzoimidazole-5-carboxylic acid (3-imidazole-1-yl-propyl) amide

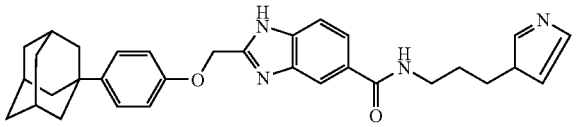 [SMILES: O=C(NCCCC1C=CN=C1)c1ccc2[nH]c(COc3ccc(C45CC6CC(CC(C6)C4)C5)cc3)nc2c1]

To solution of 2-(4-adamantan-1-yl-phenoxymethyl)-1H-benzoimidazole-5-carboxylic acid (70.0 mg, 0.18 mmol), 3-imidazole-1-yl-propylamine (33.8 mg, 0.27 mmol, 0.03 ml) and HBTU (136.5 mg, 0.36 mmol) in DMF 4.0 mL was added DIPEA (46.5 mg, 0.36 mmol, 0.06 ml). After stirring at room temperature, the mixture was partitioned between ethyl acetate and brine. The organic phase was dried (MgSO$_4$ anh), and concentrated. The residue was purified by Prep-TLC (CH$_2$Cl$_2$:MeOH=10:1) to give 2-(4-adamantan-1-yl-phenoxymethyl)-1H-benzoimidazole-5-carboxylic acid (2-dimethylamino-ethyl)-amide as a yellow solid (30.9 mg, 33.7% yield).

$^1$H-NMR (CDCl$_3$+CD$_3$OD, 300 Hz) 8.28 (1H, s, NH), 8.03-8.10 (2H, m, aromatic-H), 7.70-7.73 (1H, m, aromatic-H), 7.56 (1H, d, J=8.7H aromatic-H), 7.23-7.26 (4H, m, aromatic-H), 7.11 (1H, s, NH), 6.92-6.96 (2H, m, aromatic-H), 5.27 (2H, s, CH$_2$), 4.16 (2H, m, CH$_2$), 3.42 (2H, m, CH$_2$), 2.14 (2H, m, CH$_2$), 2.02 (3H, m, adamantly-H), 1.81 (6H, m, adamantly-H), 1.65-1.75 (6H, m, adamantly-H).

EXAMPLE 156

2-(2,4-dichloro-phenoxymethyl)-1H-benzoimidazole-5-carboxylic acid hydrazide

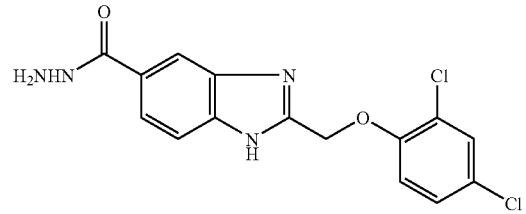

2-(2,4-dichloro-phenoxymethyl)-1H-benzoimidazole-5-carboxylic acid methyl ester (20 mg, 0.057 mmol) and hydrazine hydrate 0.2 ml was heated to reflux until reaction completion, then put cool water, diluted with ethyl acetate. The organic phase was separated, washed with brine and water, dried over anhydrous MgSO$_4$. The resultant crude was filtered and concentrated under reduced pressure to afford 2-(2,4-dichloro-phenoxymethyl)-1H-benzoimidazole-5-carboxylic acid hydrazide as a solid (3 mg, 15% yield).

$^1$H NMR (DMSO-d$_6$, 300 MHz) 12.9 (1H, brs, benzoimidazole NH), 9.73 (1H, s, CONH), 8.14-7.99 (1H, m, aromatic), 7.73-7.52 (3H, m, aromatic), 7.42-7.34 (2H, m, aromatic), 5.44 (2H, s, OCH$_2$), 4.47 (2H, brs, NH$_2$).

EXAMPLE 157

2-(2,4-dichloro-phenoxymethyl)-3H-benzoimidazole-5-carboxylic acid (furan-2-ylmethyl)-amide

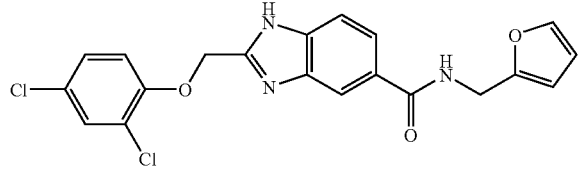 [SMILES: O=C(NCc1ccco1)c1ccc2[nH]c(COc3ccc(Cl)cc3Cl)nc2c1]

To solution of 2-(2,4-dichloro-phenoxymethyl)-3H-benzoimidazole-5-carboxylic acid (22.2 mg, 0.07 mmol), furfuryl amine (10.7 mg, 0.11 mmol, 0.01 ml), EDC (21.1 mg, 0.11 mmol) and HOBt (14.9 mg, 0.11 mmol) in DMF 3.0 mL was added DIPEA (14.2 mg, 0.11 mmol, 0.02 ml). After stirring at room temperature, the mixture was partitioned between ethyl acetate and 10% HCl. The organic phase was washed with brine, dried (MgSO$_4$ anh), and concentrated. The residue was purified by Prep-TLC (n-Hexane:EtoAc:MeOH=6:3:1) to give 2-2,4-dichloro-phenoxymethyl)-3H-benzoimidazole-5-carboxylic acid (furan-2-ylmethyl)-amide as a white solid (14.7 mg, yield: 37.92%).

$^1$H-NMR (DMSO-d$_6$, 300 Hz) 8.12 (1H, s, NH), 8.01 (1H, s, aromatic-H), 7.70 (1H, d, J=8.1 Hz, aromatic-H), 7.62 (1H, d, J=8.4 Hz, aromatic-H), 7.37-7.40 (2H, m, aromatic-H), 7.16-7.20 (1H, m, aromatic-H), 7.02 (1H, d, J=9.3 Hz, aromatic-H), 6.57 (1H, m, NH), 6.30-6.35 (2H, m, aromatic-H), 5.42 (2H, s, $CH_2$), 4.67 (2H, d, J=4.8 Hz, CH)

Formulations comprising the compound are prepared as follows.

FORMULATION EXAMPLE 1

Powder Formulation

| | |
|---|---|
| Cpd. Of Chemical Formula 1A or 1B | 2 g |
| Lactose | 1 g |

These components were mixed and filled in an airtight sac to prepare a powder agent.

FORMULATION EXAMPLE 2

Tablet Formulation

| | |
|---|---|
| Cpd. Of Chemical Formula 1A or 1B | 100 mg |
| Corn Starch | 100 mg |
| Lactose | 100 mg |
| Mg Stearate | 2 mg |

These components were mixed and subjected to a conventional tabletting process to produce a tablet.

FORMULATION EXAMPLE 3

Capsule Formulation

| | |
|---|---|
| Cpd. Of Chemical Formula 1A or 1B | 100 mg |
| Corn Starch | 100 mg |
| Lactose | 100 mg |
| Mg Stearate | 2 mg |

These components were mixed and loaded into a gelatin capsule according to a conventional method to prepare a capsule dosage form.

EXPERIMENTAL EXAMPLE 1

Assay for Inhibition of HIF-Mediated Transcriptional Activity (HRE Reporter Assay)

Six tandem repeats of HRE (hypoxia Responsive Element 5'-ACGTG-3'), which is present in a human VEGF gene, was inserted into the multi-cloning region of a pGL3-basic vector (Promega) containing a luciferase gene as a reporter gene to produce a recombinant pGL3-HRE-luciferase vector which was then used to assay the compounds prepared in the above Examples for inhibition activity against HIF-mediated transcriptional activity.

<1-1> Assay of HIF Activation Level

The hepatocellular carcinoma cell line HepG2 or Hep3B, both available from ATCC (American Type Culture Collection), and the gastric carcinoma cell line AGS, available from ATCC, were grown at 70% confluency in culture dishes and co-transfected with an internal control vector (pRL-CMV, Promega) and the recombinant pGL3-HRE-luciferase vector using Lipofectamine Plus Reagent (Invitrogen). HepG2 and AGS cells were treated with the compound of Chemical Formula 1A while Hep3B and AGS cells were treated with the compound of Chemical Formula 1B. The compound of Chemical Formula 1A was used in a concentration of 10 μm for HepG2 or AGS cells. The compound of Chemical Formula 1B was used in a concentration of 30 μM for Hep3B and in a concentration of 10 μM for AGS cells. After culture for 48 hours, the compounds of Examples were applied to respective cells which were then incubated for 16 hrs in hypoxia (1% $O_2$, 94% $N_2$, and 5% $CO_2$). The compounds prepared in Examples above were assayed for inhibition activity against HIF-1 by measuring the activity of the luciferase, induced in hypoxia, using a Dual-luciferase reporter assay system (Promoga). In this regard, the luciferase activity was measured for 10 sec using a Microlumat Plus luminometer (EG&G Berthold). In the meanwhile, the renilla luciferase activity from the control vector PRL-CMV (Promega) was measured to normalize the data obtained.

The results are given in Table 1.

On the basis of the renilla luciferase activity, the HIF activity % remaining after treatment with the compounds was corrected.

<1-2> Assay of $IC_{50}$

The hepatocellular carcinoma cell line Hep3B, available from ATCC (American Type Culture Collection), and the gastric carcinoma cell line AGS, available from ATCC, were seeded in a density of $5 \times 10^4$ cell/well and were incubated for 48 hrs at 37° C., 5% $CO_2$ in culture dishes and cotransfected with an internal control vector (pRL-CMV, Promega) and the recombinant pGL3-HRE-luciferase vector using Lipofectamine Plus Reagent (Invitrogen). Compounds of Formula 1 dissolved in DMSO were placed in the incubated cell lines and were treated in various concentrations from 0.01 to 100 μM for 16 hrs and after then the number of survival cell lines at each concentration of compound was shown by a graph and a concentration of $IC_{50}$ at which 50% cells of the compounds were survived was assayed. The results are given in Table 1. Also, with respect to the compounds prepared in Experimental Examples 86, 87, 98, 102-107, 112 and 113, a concentration of $IC_{50}$ was assayed in the same manner as stated with cell line SK-Hep-1, available from ATCC (American Type Culture Collection), and the result was given in Table 2.

TABLE 2

| | SK-Hep-1 IC50 (μM) |
|---|---|
| Example 86 | 1.03 |
| Example 87 | >30 |
| Example 98 | 2.0 |
| Example 102 | >30 |
| Example 103 | 1.9 |
| Example 104 | 2.5 |
| Example 105 | >30 |
| Example 106 | 3.4 |
| Example 107 | <1 |
| Example 112 | 11.9 |
| Example 113 | 0.59 |
| YC-1 | >30 |

As a control compound, YC-1, commercially available from AG Scientific Inc. San Diego, Calif., was used in the same manner as above, and the results are shown in Table 1.

As apparent from data of Table 1 and Table 2 above, the compounds of the present invention, in particular the compounds prepared in Experimental Examples 18, 23, 44, 48, 113 or 126, were found to show excellent inhibition activity against the transcription mediated by HIF-1, which is induced in hypoxia. Therefore, the compounds of the present invention are useful as active ingredients for cancer therapy because they can inhibit the expression of the genes implicated in the malignant transformation of cancer, thereby suppressing the growth and metastasis of cancer.

Experimental Example 2

Assay for Inhibition of Accumulation of HIF-1α in Hypoxia

The compounds identified to show excellent inhibition of HIF-mediated transcription activity in Experimental Example 1 were assayed for HIF-1α accumulation inhibition in the gastric carcinoma cell line AGS and the hepatocellular carcinoma cell line Hep3B or HepG2. In its regard, the compounds prepared in Examples 18 and 126 were used to measure the inhibition of HIF-1α accumulation in the hepatocellular carcinoma cell line HepG2 as follows.

<2-1> Assay of HIF-1α Accumulation Inhibition at Each Concentration

HIF-1α accumulation inhibition of the compounds prepared in Experimental Examples 18, 23, 44, 48, 113 or 126 was assayed in the hepatocellular carcinoma cell line Hep3B as follows.

The inhibitory effect of the compound prepared in Example 18, 23, 44, 48, 113 or 126 on HIF-1α protein production induced in hypoxia was assayed using a Western blotting method. The hepatocellular carcinoma cell line HepG2 (American Type Culture Collection) was grown to 70% confluency in culture dishes and treated with various concentrations of the compounds of Examples 18, 23, 44, 48, 113 or 126 in DMSO. DMSO alone was used as a control (expressed as 'DMSO' in FIG. 1). The hepatocellular carcinoma cell line was then incubated for 12 hrs in hypoxia (1% $O_2$, 94% $N_2$, and 5% $CO_2$, expressed as '1% $O_2$' in FIG. 1), followed by preparing a nuclear extract with an NE-PER reagent (Pierce). Approximately 30 µg of protein was obtained from each of the nuclear extracts using SDS-PAGE (sodium dodecyl sulfate-polyacrylamide gel electrophoresis), and was then transferred onto a polyvinylidene fluoride (PVDF) membrane. Quantitative analysis for HIF-1α protein was conducted using an anti-HIF-1α antibody (R&D System) and a secondary antibody labeled with horseradish peroxidase (HRP). In order to confirm the existence of the same quantity of the nuclear extracts on respective PVDF membranes, they were deprived of the HIF-1α antibody using a buffer containing 2-mercaptoethanol and quantitatively measured for HIF-1β topoisomerase-1 using HIF-1β or anti-topoisomerase-1 antibody (expressed as 'TOPO-1' in FIG. 1) (Santa Cruz).

The results are given in FIG. 1.

As seen in FIG. 1, the compounds prepared in the present invention were found to inhibit the production of HIF-1α protein in a dose-dependent manner in hypoxia with no influence on the production of topoisomerase-1 (TOPO-1) or HIF-1β. The inhibition of these compounds against HIF-1-mediated transcriptional activity in hypoxia is attributed to the suppression of the HIF-1α expression induced upon hypoxia HIF-1α, as a constituent of HIF-1, plays an important role in the expression of target genes of HIF-1. Therefore, the compounds of the present invention are useful as active ingredients for cancer therapy because they can inhibit the expression of the HIF-1α protein responsible for the growth and metastasis of cancer in a dose-dependent manner.

<2-2> Assay of HIF-1α Accumulation Inhibition at Each Time

Figure 2:
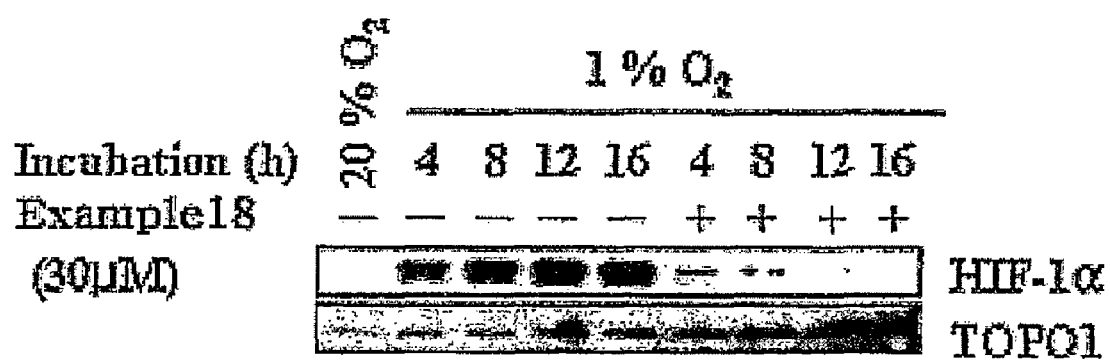
FIG. 2 shows the inhibition activity of the compounds of the invention against 1a accumulation in hypoxia at each time.

While One of the hepatocellular carcinoma cell lines Hep3B, available from AITC (American Type Culture Collection), was incubated in hypoxia for 4, 8, 12 and 16 hrs, the amounts of HIF-1α and topoisomerase-1 (TOPO-1) were assayed and the result was given in FIG. 2.

As shown in FIG. 2, in case the compounds prepared in the present invention were not added, the amount of HIF-1α increased as time went on but in case the compounds were added, the amount of HIF-1α, decreased rapidly and then it was not detected after 12 hrs. The amount of topoisomerase-1 (TOPO-1) was nearly regular regardless of addition of the compounds.

Accordingly, the compounds prepared in the present invention inhibits the accumulation of HIF-1α playing a pivotal role in the growth and metastasis of cancer depending on time, thereby inhibiting the growth and metastasis of cancer, so it can be used as an effective ingredient for anticancer agent.

Experimental Example 3

Effect on Expression of EPO or VEGF, Target Genes of HIF-1, in Hypoxia

The inhibitory effect of the compounds of the present invention on HIF-1 activity was confirmed by assaying the compounds prepared in Examples for inhibition activity on the expression of EPO or VEGF, a representative target gene of HIF-1 through an analysis of RT-PCR (reverse transcriptase polymerase chain reaction). VEGF, a target gene of HIF-1, encodes an angiogenesis factor playing a pivotal role in the growth and metastasis of cancer and EPO is a hematosis hormone gene, and both genes have been known for being deeply related to the development and the aggravation of cancer. The compounds of the present invention were measured for inhibition of VEGF expression in AGS, Hep3B and HepG2 cells. In this regard, the hepatocellular carcinoma cell line Hep3B was treated with compounds prepared in Examples 18 and 126 as follows.

After being grown to 70% confluency in culture dishes, HepG2 cells (American Type Culture Collection) were treated with various concentrations (0 µm, 1 µm 3 µM and 10 µm) of compounds prepared in Examples 18, 44, 113 or 126 and incubated for 12 hrs in hypoxia (1% $O_2$, 94%, $N_2$, and 5% $CO_2$, expressed as '1% $O_2$' in FIG. 2). Total RNA was isolated using an RNA Mini kit (Qiagen). From the total RNA (2 µg) thus obtained, cDNA was synthesized using an RT-PCR kit (Invitrogen), and was used to amplify EPO or VEGF by PCR in the presence of EPO or VEGF-specific primers. EPO or VEGF expression was quantitatively analyzed by running the PCR products on agarose gel. As an internal control, GAPDH was simultaneously amplified so as to analyze the selective inhibition of each compound for VEGF. Base sequences of primers used for the amplification of EPO, VEGF and GAPDH used in the present invention were as follows.

```
EPO;    5'-CACTTTCCGCAAACTCTTCCG-3'   (sense),
        (SEQ ID NO: 1)
        5'-GTCACAGCTTGCCACCTAAG-3'    (antisense).
        (SEQ ID NO: 2)
```

```
VEGF;   5'-GCTCTACCTCCACCATGCCAA-3'   (sense),
        (SEQ ID NO: 3)
        5'-TGGAAGATGTCCACCAGGGTC-3'   (antisense).
        (SEQ ID NO: 4)

GAPDH;  5'-ACCACAGTCCATGCCATCAC-3'    (sense),
        (SEQ ID NO: 5)
        5'-TCCACCACCCTGTTGCTGTA-3'    (antisense).
        (SEQ ID NO: 6)
```

Figure 3:
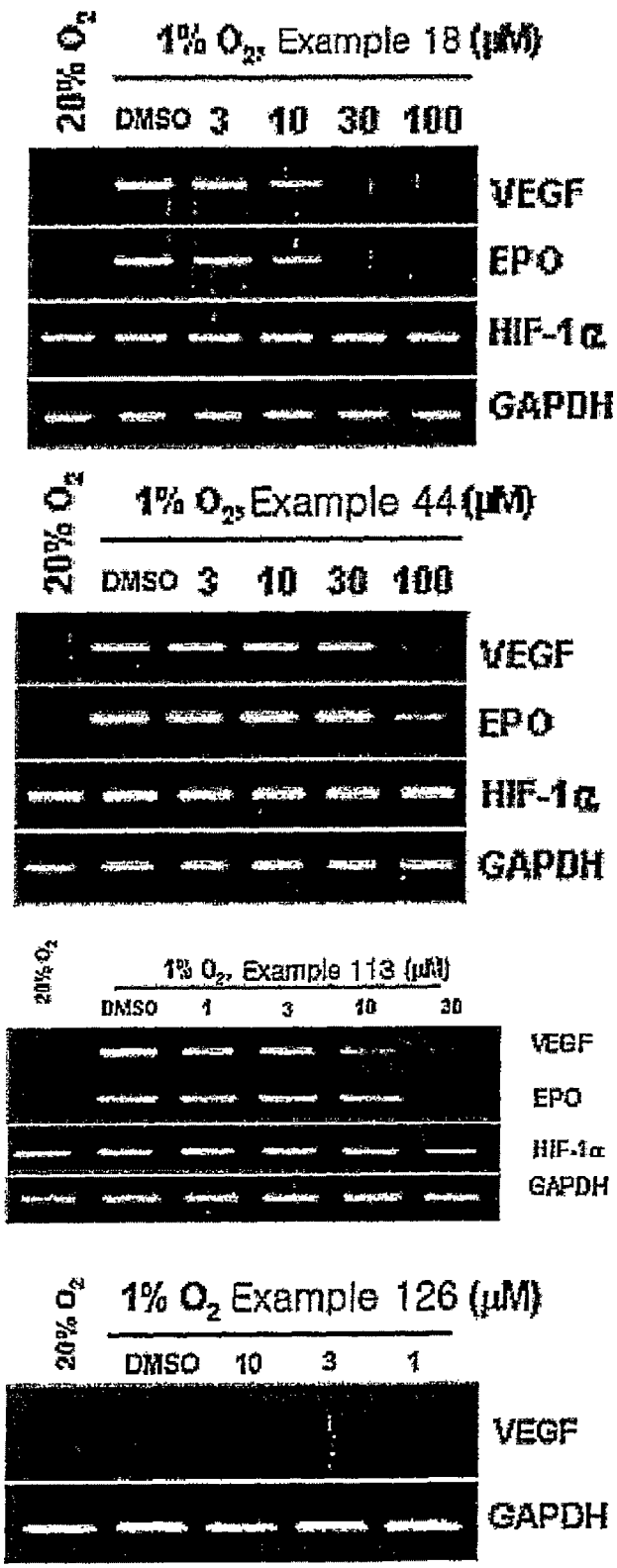
FIG. 3 shows the inhibition activity of the compounds of the invention against VEGF expression in hypoxia.

The results are given in FIG. 3.

As seen in FIG. 3, it was observed that the compounds of Examples 18, 44, 113 and 126 of the invention were found to inhibit the expression of EPO or VEGF dose-dependently in hypoxia, regardless of the effects on the expression of the HIF-1a and GAPDH in Hep3B cell.

Accordingly, the compounds of the present invention were found to selectively inhibit the expression of EPO or VEGF, a target gene of HIF-1. Therefore, the compounds of the present invention are useful as active ingredients for cancer therapy because they can selectively inhibit the expression of VEGF, an angiogenesis factor playing an important role in the malignant transformation of cancer, or the expression of EPO a hematosis hormone gene, a thereby suppressing the growth and metastasis of cancer.

Having the selective inhibition of the expression of the HIF-1 target VEGF, the compounds of the present invention can be used as an active ingredient for the treatment of diabetic retinopathy or arthritis, which is aggravated upon HIF-1-mediated VEGF expression in hypoxia Experimental Example 4

Assay for In Vivo Anticancer Activity in Mouse

The compounds prepared in Examples 18, 95 or 126 were measured for in vivo anticancer activity in mice.

Female nude mice 5-6 weeks old (Crj:BALB/c nu/nu, Charles River) were bred in germ-free breeding rooms maintained at constant temperature and humidity. The nude mice were anesthetized before incision of the chest skin. The metastatic breast carcinoma cell line MDA-MB-435, obtained from DR D. R. Welch, Univ. Alabama, was implanted at a count of $10^6$ cells/mouse into the mammary gland fat pad, and the incisions were then closed with surgical clips. The nude mice were divided into test groups and a control group, each consisting of 6 mice. When the transplanted breast cancer had grown to a size of about 50 mm$^3$ as measured using a caliper, the compounds prepared in Example 18, 95 or 126 were administered at various concentrations. In more detail, the compounds were dissolved at concentrations of 20 mg/kg and 50 mg/kg in a solvent containing 94.5% of physiological saline, 0.5% of DMSO and 5% of Tween 20 (hereinafter referred to as 'Solvent A'), the concentration of the compounds prepared in Experimental Examples 18, 95 or 126 was adjusted at 20 mg/kg or 50 mg/kg and adminstered once to the experimental groups at a dose of 100 µl a day per individual. For the control group, Solution A alone was used at a dose of 100 µl once a day. Thereafter, tumor volumes and body weights were measured once a week. Tumor volumes were calculated according to the following Mathematic Formula 1.

Tumor Volume (mm$^3$)=(Length of Long Axis,mm)× (Length of Short Axis,mm)$^2$×0.5      <Mathematic Formula 1>

Figure 4:
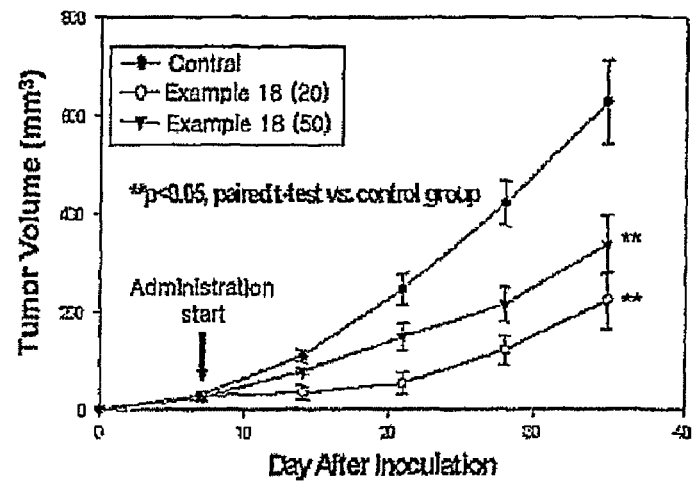
FIG. 4 and FIG. 5 show the in vivo anticancer activity of the compounds of the invention in nude mice.
Figure 4:
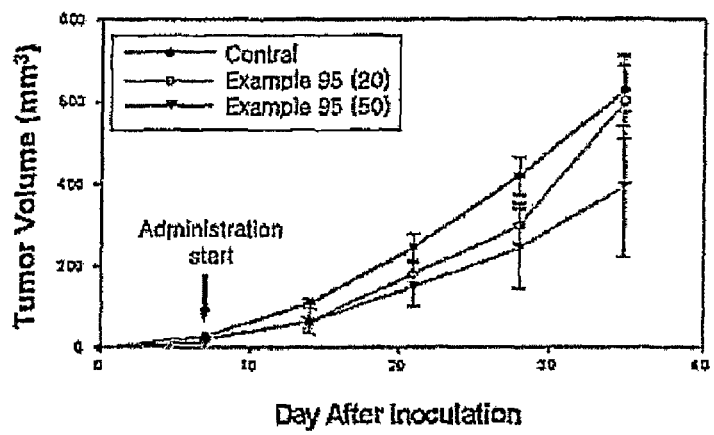
Figure 4:
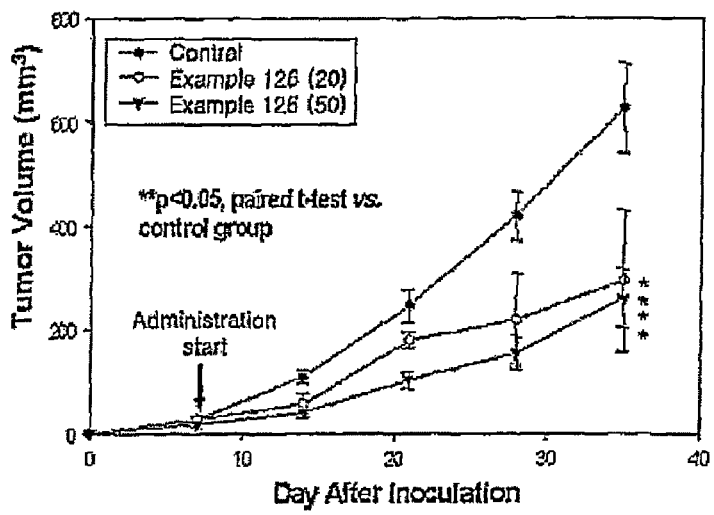

The results are given in FIG. 4. Also, the cancer cell was extracted from the mouse 35 days later and was represented in FIG. 5.

When used at a concentration of 50 mg/kg, as seen in FIG. 3, the compounds prepared in Examples 18 and 126 were observed to further inhibit the growth of the cancer cells by 64.6% and 58.6%, respectively, compared to the control. In the test groups administered with a concentration of 20 mg/kg of the compounds of Examples 18 and 126, the growth of the cancer cells was inhibited by a further 46.5% and 53%, respectively, compared to the control. In the test groups administered with a concentration of 20 mg/kg of the compound of Example 95, the growth of the cancer cells was inhibited by 4.3%, in the test groups administered with a concentration of 50 mg/kg, the growth of the cancer cells was inhibited by 36.5%, compared to the control.

Figure 5:
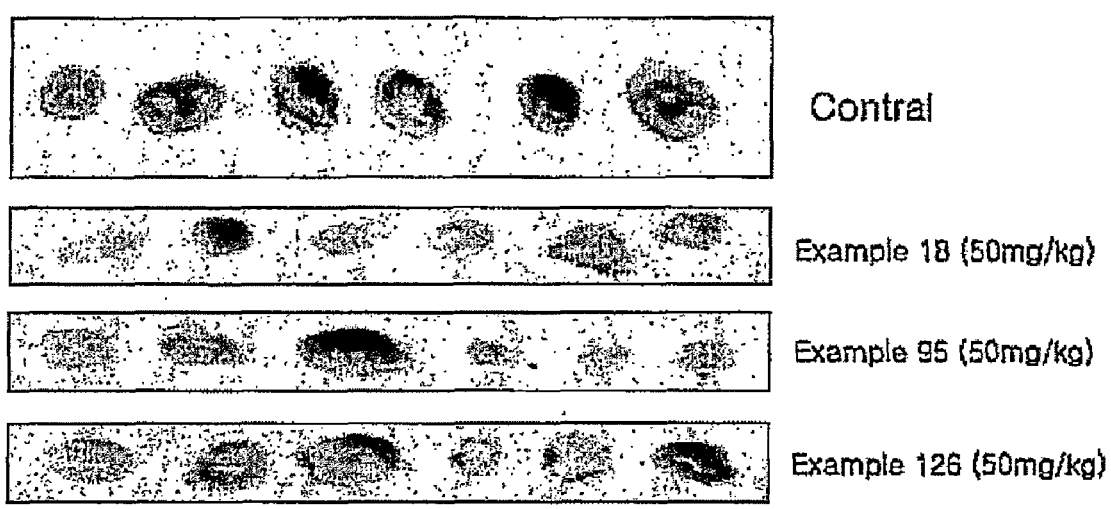

Also, as shown in FIG. 5, the extracted cancer cells of the test groups became smaller, compared to that of the control. No dead were observed in six mice of each group which were administered with the concentration of 50 mg/kg of the compounds prepared in Examples 18, 95 or 126. Also, the mice of the test groups did not appear different from those of the control in terms of body weight and feed intake. Therefore, the compounds of the present invention were very effective active ingredients for anticancer agents, thanks to the in vivo anticancer activity and the lack of general cellular toxicity thereof, as demonstrated by experiments on mice.

Experimental Example 5

Cytotoxicity Assay

An acute cytotoxicity assay was conducted with five-week-old SPF C57BL/6 mice (Samtako BioKorea) as follows.

The compounds prepared in Examples 18 and 126 were suspended in a solvent comprising 94.5% of physiological saline, 0.5% of DMSO and 5% of Tween 80, and 0.5 mL of each of the suspensions was orally administered once into five mice at a dose of 300 mg/kg. The mice were observed for death, clinical syndromes, and body weight and then autopsied for the observation of abdominal and thoracic organs with the naked eye.

No noteworthy clinical syndromes were found, no mice died, and no changes due to toxicity were observed with respect to body weight or during the autopsy. Consequently, the compounds prepared in Examples 18 and 126 are safe with a minimal lethal dose of at least 300 mg/kg for oral administration, as demonstrated by the observation of no toxicity up to a dose of 300 mg/kg.

[Industrial Applicability]

As described in the foregoing, the compounds in accordance with the present invention have anticancer activity not through general cytotoxicity, but through selective inhibition of HIF-1 activity. Thus, the compounds of the present invention can be effectively used to suppress the growth and metastasis of cancer because they inhibit the HIF-1-mediated expression of the genes implicated in the malignant transformation of cancer. Particularly, the anticancer activity of compounds of the present invention is not attributed to general cytotoxicity, but to dose-dependent inhibition of the accumulation of HIF-1α protein.

Having inhibition activity against HIF-1, therefore, the compounds of the present invention can be effectively used in the treatment of various cancerous diseases, including liver cancer, stomach cancer, breast cancer, colon cancer, bone cancer, pancreatic cancer, head or neck cancer, uterine cancer, ovarian cancer, rectal cancer, esophageal cancer, small intestine cancer, periproctic cancer, oviduct cancer, endometrial cancer, cervical cancer, vulva cancer, vaginal cancer, Hodgkin's disease, prostate cancer, bladder cancer, kidney cancer, ureter cancer, renal cell carcinoma, renal pelvis cancer, and CNS tumors.

Thanks to selective inhibition of the expression of the HIF-1 target gene VEGF, the compounds of the present invention can be also used as active ingredients of therapeutics for diabetic retinopathy or arthritis, which is aggravated upon HIF-1-mediated VEGF expression.

[Sequence List Pretext]
SEQ ID NO: 1 is a sense primer of an EPO gene,
SEQ ID NO: 2 is a antisense primer of an EPO gene,
SEQ ID NO: 3 is a sense primer of a VEGF gene,
SEQ ID NO: 4 is an antisense primer of a VEGF gene,
SEQ ID NO: 5 is a sense primer of a GAPDH gene,
SEQ ID NO: 6 is an antisense primer of a GAPDH gene.

The invention claimed is:

1. A compound, represented by the following Chemical Formula 1A,

<Chemical Formula 1A>

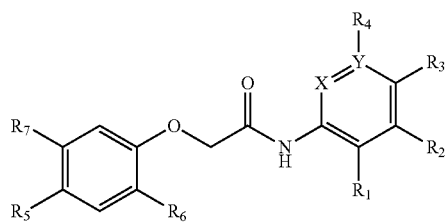

wherein,

X and Y are each C or N, provided that when X is C, Y is C or N and when Y is N, X is C or N;

$R_1$ is selected from the group consisting of H, OH and COORa, wherein Ra is H or $C_1$~$C_2$ alkyl;

$R_2$ is selected from the group consisting of H, OH, CN, $CF_3$, $C_1$~$C_2$ alkyl, COORa, $CH_2$COORa, CONRbRc, $SO_2NH_2$, $SO_2CH_3$, $SO_2CH_2OH$, $O(C=O)NH_2$, $OSO_2NH_2$, tetrazole, $C_1$~$C_3$ alkyl-substituted tetrazole, and $C_1$~$C_3$ alkyl-substituted benzoyl, wherein Ra is H or $C_1$~$C_2$ alkyl; and Rb and Rc are independently selected from the group consisting of:

$C_3$~$C_5$ heteroaryl containing N, O and/or S;

$C_1$~$C_5$ alkyl substituted with a $C_3$~$C_5$ heteroaryl or heterocyclic group containing N, O and/or S;

$C_1$~$C_3$ alkyl substituted with OH and/or phenyl;

phenyl substituted with halogen and/or trihalomethyl;

naphthyl;

H; and $C_1$~$C_3$ alkyl, $R_3$ is selected from the a group consisting of H, COORa and $SO_2NH_2$, wherein Ra is H or $C_1$~$C_2$ alkyl;

$R_4$ is selected from the group consisting of H, COORa and CONRbRc, wherein

Ra is H or $C_1$~$C_2$ alkyl; and

Rb and Rc are independently selected from the group consisting of:

$C_1$~$C_3$ alkyl substituted with a $C_3$~$C_5$ heteroaryl or heterocyclic group containing N, O and/or S;

$C_1$~$C_5$ alkyl substituted with an amino group or a $C_1$~$C_2$ alkyl-substituted amino group; H; and $C_1$~$C_2$ alkyl;

$R_5$ is adamantly and $R_6$, and $R_7$ are independently selected from the group consisting of H and halogen.

2. A compound selected from the group consisting of:

2-(4-adamantan-1-yl-phenoxy)-N-(3-methanesulfonyl-phenyl)-acetamide;

3-[2-(4-adamantan-1-yl-phenoxy)-acetylamino]-benzoic acid methyl ester;

3-[2-(4-adamantan-1-yl-phenoxy)-acetylamino]-benzoic acid ethyl ester;

3-[2-(4-adamantan-1-yl-phenoxy)-acetylamino]-phenyl-acetic acid methyl ester;

4-[2-(4-adamantan-1-yl-phenoxy)-acetylamino]-benzoic acid methyl ester;

2-[2-(4-adamantan-1-yl-phenoxy)-acetylamino]-benzoic acid methyl ester;

5-[2-(4-adamantan-1-yl-phenoxy)-acetylamino]-isophthalic acid dimethyl ester;

3-[2-(4-adamantan-1-yl-phenoxy)-acetylamino]-4-hydroxy-benzoic acid methyl ester;

4-[2-(4-adamantan-1-yl-phenoxy)-acetylamino]-sophthalic acid dimethylester;

3-[2-(4-adamantan-1-yl-phenoxy)-acetylamino]-benzamide;

2-(4-adamant-1-yl-phenoxy)-N-(3-sulphamoyl-phenyl)-acetamide;

2-(4-adamantan-1-yl-phenoxy)-N-(4-sulphamoyl-phenyl)-acetamide;

2-(4-adamantan-1-yl-phenoxy)-N-(3-cyano-phenyl)-acetamide;

2-(4-adamantan-1-yl-phenoxy)-N-(3-trifluoromethylphenyl)acetamide;

2-(4-adamantan-1-yl-phenoxy)-N-(3-hydroxy-phenyl)-acetamide;

2-(4-adamantan-1-yl-phenoxy)-N-(3-benzoyl-phenyl)-acetamide;

2-[2-(4-adamantan-1-yl-phenoxy)-acetylamino]-benzoic acid;

3-[2-(4-adamantan-1-yl-phenoxy)-acetylamino]-benzoic acid;

3-[2-(4-adamantan-1-yl-phenoxy)-acetylamino]-phenyl-acetic acid;

4-[2-(4-adamantan-1-yl-phenoxy)-acetylamino]-benzoic acid;

3-[2-(4-adamantan-1-yl-phenoxy)-acetylamino]-4-hydroxy-benzoic acid;

5-[2-(4-adamantan-1-yl-phenoxy)-acetylamino]-isophthalic acid;

2-(4-adamantan-1-yl-phenoxy)-N-[3-(1H-tetrazol-5-yl)phenyl]-acetamide;

3-[2-(4-adamantan-1-yl-phenoxy)-acetylamino]-4-hydroxy-benzamide;

3-[2-(4-adamantan-1-yl-phenoxy)-acetylamino]-4-hydroxy-N, N-dimethyl-benzamide;

3-[2-(4-adamantan-1-yl-phenoxy)-acetylamino]-N-furan-2-ylmethyl-4-hydroxy-benzamide;

3-[2-(4-adamantan-1-yl-phenoxy)-acetylamino]-N-(2-dimethylamino-ethyl)-4-hydroxy-benzamide;

3-[2-(4-adamantan-1-yl-phenoxy)-acetylamino]-4-hydroxy-N-(3-morpholin-4-yl-propyl)-benzamide;

3-[2-(4-adamantan-1-yl-phenoxy)-acetylamino]-N-(4-chloro-phenyl)-benzamide;

3-[2-(4-adamantan-1-yl-phenoxy)-acetylamino]-N-(3-trifluoromethyl-phenyl)-benzamide;

3-[2-(4-adamantan-1-yl-phenoxy)-acetylamino]-N-naphthalen-2-yl-benzamide;
3-[2-(4-adamantan-1-yl-phenoxy)-acetylamino-N-furan-2-ylmethyl-benzamide;
3-[2-(4-adamantan-1-yl-phenoxy)-acetylamino]-N-(2-pyridin-4-yl-ethyl)-benzamide;
2-[2-(4-adamantan-1-yl-phenoxy)-acetylamino]-isonicotinic acid methyl ester;
5-[2-(4-adamantan-1-yl-phenoxy)-acetylamino]-nicotinic acid methyl ester;
2-(4-adamantan-1-yl-phenoxy)-N-(4-methyl-pyridin-2-yl)-acetamide;
5-[2-(4-adamantan-1-yl-phenoxy)-acetylamino]-nicotinic acid;
2-[2-(4-adamantan-1-yl-phenoxy)-acetylamino]-isonicotinic acid
5-[2-(4-adamantan-1-yl-phenoxy)-acetylamino]-N-furan-2-ylmethyl-nicotinamide;
5-[2-(4-adamantan-1-yl-phenoxy)-acetylamino]-N-(2-pyridin-4-yl-ethyl)nicotinamide;
5-[2-(4-adamantan-1-yl-phenoxy)-acetylamino]-N-(3-imidazol-1-yl-propyl)-nicotinamide;
2-[2-(4-adamantan-1-yl-phenoxy)-acetylamino]-N-(4-chloro-phenyl)-isonicotinamide;
2-[2-(4-adamantan-1-yl-phenoxy)-acetylamino]-N-furan-2-ylmethyl-isonicotinamide;
2-[2-(4-adamantan-1-yl-phenoxy)-acetylamino]-N-(2-pyridin-4-yl-ethyl)-isonicotinamide;
2-[2-(4-adamantan-1-yl-phenoxy)-acetylamino]-N-(3-imidazol-1-yl- propyl)-isonicotinamide;
5-[2-(4-adamantan-1-yl-phenoxy)-acetylamino]-nicotinamide; and
2-[2-(4-adamantan-1-yl-phenoxy)-acetylamino]-isonicotinamide.

3. The compound according to claim 1, wherein the compound is 3-[2-(4-adamantan-1-yl-phenoxy)-acetylamino]-4-hydroxy-benzoic acid methyl ester.

4. A method for preparing a compound represented by Chemical Formula 1A of claim 1 according to the following Reaction Scheme 3, in which a compound (1Ad) is converted into a compound (1Ae) in the presence of lithium iodide in an organic solvent, wherein the solvent is pyridine, $CH_2Cl_2$ or DMF.

<Reaction Scheme 3>

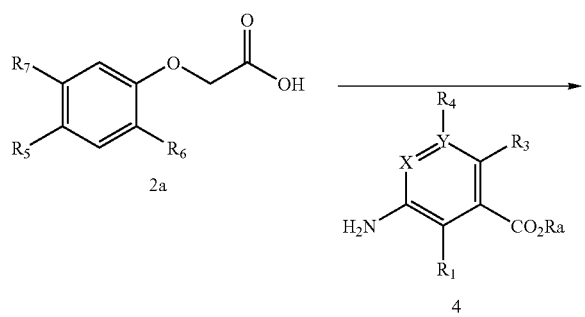

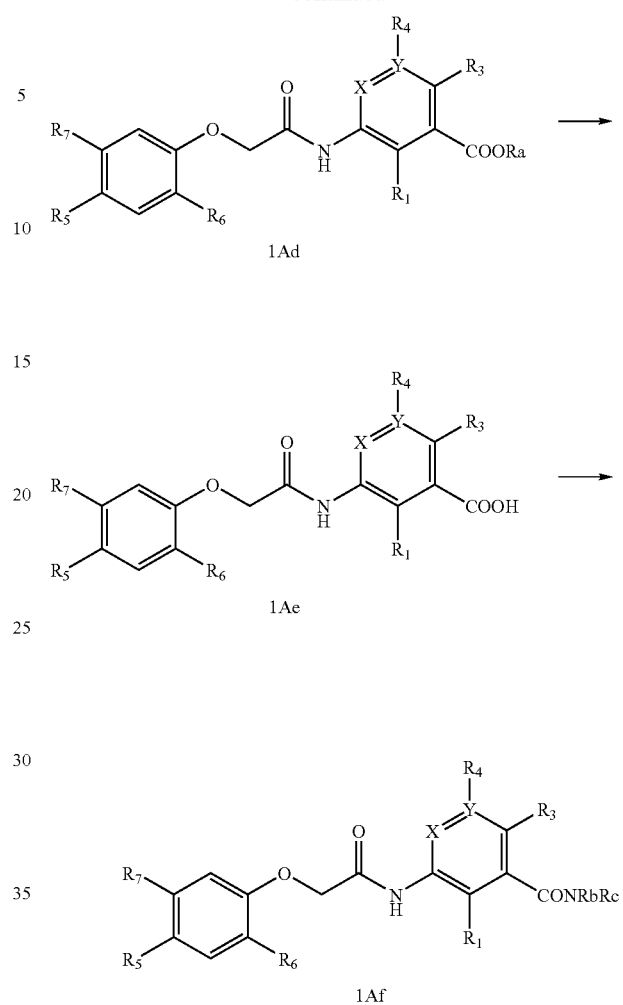

(wherein $R_1$, $R_3$~$R_7$, X, Y, Ra, Rb and Rc are each as defined in Chemical Formula 1A of claim 1).

5. An HIF-1 inhibitor, comprising the compound of claim 1 as an active ingredient.

6. A pharmaceutical composition for the treatment of breast cancer, comprising the compound of claim 1 as an active ingredient.

7. A method for treating breast cancer in a subject comprising administering a pharmaceutically effective amount of the compound of claim 1 to the subject in need thereof.

8. A method for treating breast cancer in a subject comprising administering a pharmaceutically effective amount of the compound of claim 2 to the subject in need thereof.

* * * * *

```
                          SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: EPO sense primer

<400> SEQUENCE: 1
cactttccgc aaactcttcc g                                      21

<210> SEQ ID NO 2
<211> LENGTH: 20
<212> TYPE: DNA
<213> ORGANISM: Artificial Sequence
<220> FEATURE:
<223> OTHER INFORMATION: EPO antisense primer

<400> SEQUENCE: 2
gtcacagctt gccacctaag                                        20

<210> SEQ ID NO 3
<211> LENGTH: 21
<212> TYPE: DNA
<213> ORGANISM: Artificial Sequence
<220> FEATURE:
<223> OTHER INFORMATION: VEGF sense primer

<400> SEQUENCE: 3
gctctacctc caccatgcca a                                      21

<210> SEQ ID NO 4
<211> LENGTH: 21
<212> TYPE: DNA
<213> ORGANISM: Artificial Sequence
<220> FEATURE:
<223> OTHER INFORMATION: VEGF antisense primer

<400> SEQUENCE: 4
tggaagatgt ccaccagggt c                                      21

<210> SEQ ID NO 5
<211> LENGTH: 20
<212> TYPE: DNA
<213> ORGANISM: Artificial Sequence
<220> FEATURE:
<223> OTHER INFORMATION: GAPDH sense primer

<400> SEQUENCE: 5
accacagtcc atgccatcac                                        20

<210> SEQ ID NO 6
<211> LENGTH: 20
<212> TYPE: DNA
<213> ORGANISM: Artificial Sequence
```

```
<220> FEATURE:
<223> OTHER INFORMATION: GAPDH antisense primer

<400> SEQUENCE: 6
tccaccaccc tgttgctgta                                              20
```